United States Patent
Sukhatme et al.

(10) Patent No.: US 9,931,313 B2
(45) Date of Patent: *Apr. 3, 2018

(54) METHODS OF TREATING PROLIFERATIVE DISORDERS WITH MALATE OR DERIVATIVES THEREOF

(71) Applicant: Beth Israel Deaconess Medical Center, Inc., Boston, MA (US)

(72) Inventors: Vikas P. Sukhatme, Newton, MA (US); Jian-Guo Ren, West Roxbury, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 234 days.

This patent is subject to a terminal disclaimer.

(21) Appl. No.: 14/390,155

(22) PCT Filed: Apr. 4, 2013

(86) PCT No.: PCT/US2013/035277
§ 371 (c)(1),
(2) Date: Apr. 20, 2015

(87) PCT Pub. No.: WO2013/152193
PCT Pub. Date: Oct. 10, 2013

(65) Prior Publication Data
US 2015/0056215 A1 Feb. 26, 2015

Related U.S. Application Data

(60) Provisional application No. 61/620,235, filed on Apr. 4, 2012.

(51) Int. Cl.
| | | |
|---|---|---|
| A61K 31/225 | (2006.01) | |
| A61K 33/24 | (2006.01) | |
| A61K 45/06 | (2006.01) | |
| C12N 15/113 | (2010.01) | |
| G01N 33/50 | (2006.01) | |

(52) U.S. Cl.
CPC ........... *A61K 31/225* (2013.01); *A61K 33/24* (2013.01); *A61K 45/06* (2013.01); *C12N 15/1137* (2013.01); *G01N 33/5008* (2013.01); *C12N 2310/14* (2013.01); *C12N 2320/31* (2013.01); *G01N 2500/04* (2013.01); *G01N 2800/7023* (2013.01)

(58) Field of Classification Search
CPC ...... A61K 31/225; A61K 33/24; A61K 45/06; C12N 15/1137; C12N 2310/14; C12N 2320/31; G01N 2500/04; G01N 2800/7023; G01N 33/5008
See application file for complete search history.

(56) References Cited

U.S. PATENT DOCUMENTS

| 5,182,267 A * | 1/1993 | Ogawa | A61K 31/135 514/34 |
|---|---|---|---|
| 6,969,738 B2 | 11/2005 | Lassila et al. | |
| 2004/0152759 A1* | 8/2004 | Abrams | A61K 31/404 514/414 |
| 2007/0105887 A1* | 5/2007 | Moore | A61K 31/404 514/291 |
| 2008/0193448 A1* | 8/2008 | Baum | A61K 31/404 424/133.1 |
| 2013/0209488 A1 | 8/2013 | Sukhatme et al. | |

FOREIGN PATENT DOCUMENTS

WO    WO-2012/019154 A2    2/2012

OTHER PUBLICATIONS

Feron, Radiotherapy and Oncology, 92, pp. 329-333, 2009.*
Pelicano et al. 2006, Oncogene, 25, pp. 4633-4646.*
Ren et al., "Knockdown of Malic Enzyme 2 Suppresses Lung Tumor Growth, Induces Differentiation and Impacts PI3K/AKT Signaling," Scientific Reports, 4:5414 (2014).
DeBerardinis et al., "The biology of cancer: metabolic reprogramming fuels cell growth and proliferation," Cell Metab. 7(1):11-20 (2008).
Fantin et al., "Attenuation of LDH-A expression uncovers a link between glycolysis, mitochondrial physiology, and tumor maintenance," Cancer Cell. 9(6):425-34 (2006).
International Search Report and Written Opinion for PCT/US13/35277, dated Jan. 17, 2014 (16 pages).
Pastorino et al., "Hexokinase II: the integration of energy metabolism and control of apoptosis," Curr Med Chem. 10(16):1535-51 (2003).
Porporato et al., "Anticancer targets in the glycolytic metabolism of tumors: a comprehensive review," Front Pharmacol. 2(49) (2011) (18 pages).
Ren et al., "Induction of erythroid differentiation in human erythroleukemia cells by depletion of malic enzyme 2," PLoS One. 5(9):e12520 (2010) (12 pages).

* cited by examiner

*Primary Examiner* — Sarah Pihonak
(74) *Attorney, Agent, or Firm* — Fish & Richardson P.C.

(57) ABSTRACT

The present invention relates to methods, compositions, and diagnostic tests for treating and diagnosing proliferative disorders, such as cancel-, that result in dysregulation of malic enzyme 2. In particular, the methods and compositions include monotherapy with malate, or a derivative thereof, as well as combination therapy, such as malate, or a derivative thereof, combined with another therapeutic agent, such as a malic enzyme 2 inhibitor, an antineoplastic agent, a glycolysis inhibitor, an antiangiogenic agent, an immunomodulatory agent, an antibody, or a cytokine.

12 Claims, 19 Drawing Sheets

E. CM-H₂DCFDA

F. NADPH/NADP

METHODS OF TREATING PROLIFERATIVE DISORDERS WITH MALATE OR DERIVATIVES THEREOF

CROSS-REFERENCE TO RELATED APPLICATIONS

This application is a U.S. National Phase of International Application No. PCT/US2013/035277, filed Apr. 4, 2013, which claims benefit of U.S. Provisional Application No. 61/620,235, filed Apr. 4, 2012, which is hereby incorporated by reference in its entirety.

BACKGROUND OF THE INVENTION

The present invention relates to methods, compositions, and diagnostic tests for treating and diagnosing proliferative disorder and other related diseases that result in dysregulation of malic enzyme 2.

The progression and differentiation of tumor cells generally rely on increasing metabolism and altering normal physiological conditions. Thus far, the role of various enzymes in this metabolic process is yet unknown, and very little is known about the connection between metabolic activity, enzyme expression, and tumorigenesis. Malic enzyme 2 (ME2) is a mitochondrial enzyme that catalyzes the conversion of malate to pyruvate and $CO_2$ and uses NAD as a cofactor. Though ME2 is highly conserved over different species, the precise role of ME2 is not well-defined. Thus, many targets useful for cancer therapy (e.g., metabolic targets) and compositions for such targets have not yet been identified.

New therapeutic approaches and diagnostic methods are needed to treat or prevent cancer and related proliferative diseases.

SUMMARY OF THE INVENTION

We found that exogenous addition of malate, or a derivative thereof, mimics knockdown of malic enzyme 2 (ME2) for in vitro and in vivo systems. ME2 is expressed in various cancer cells, such as erythroleukemia cells (K562), breast cancer cells (MCF-7), melanoma cells (WM983-B), and lung cancer cells (A549 and H1650); and knockdown of ME2 expression using an RNAi agent diminished proliferation of tumor cells and increased apoptosis in vitro. Surprisingly, we have found that malate, or a derivative thereof, also diminishes proliferation and increases apoptosis in tumor cells from an A549 non-small cell lung cancer (NSCLC) cell line.

We have also discovered that malate, or a derivative thereof, sensitizes tumor cells, thereby allowing for targeting of tumor cells and for synergistically inhibiting tumor growth. Thus, combination therapies are contemplated, such as a combination of malate, or a derivative thereof, with another agent (e.g., an ME2 inhibitor, an antineoplastic agent, and/or a glycolysis inhibitor, or any described herein).

ME2 is likely a useful target in various tissues. Furthermore, we have observed increased expression of ME2 protein in different types of tumor tissues, including bladder, breast, esophagus, liver, lung, ovary, prostate, and skin. ME2 is also expressed in other tissues, including the brain (in neurons) and in the heart (in myocytes). Thus, malate, or derivatives thereof, could be useful to treat cancers or diseases in these tissues.

Accordingly, the invention features methods and compositions for treating a proliferative disorder and other diseases that result from increased activation of ME2, where such methods and compositions include malate, or a derivative thereof.

In some embodiments, the methods and compositions of the invention include malate, or a derivative thereof, and one or more ME2 inhibitors, which can be identified by any useful method (e.g., chemical screening). These compounds include those that inhibit the enzymatic activity of ME2 (e.g., either directly or indirectly, such as by inhibiting fumarate, an activator of ME2) or those that decrease ME2 gene and/or protein expression. Compounds can be identified by any useful process, such as by screening a diverse library of compounds based on the ability of compounds to increase malate (or a derivative thereof), decrease NADH or NADPH formation, increase $NAD^+$/NADH ratio, increase $NADP^+$/NADPH ratio, increase ROS activity, decrease ATP levels, inhibit phospho-ERK1/2, activate phospho-AKT, increase GATA-1 expression, decrease vimentin expression, increase apoptosis, decrease cellular proliferation, decrease pyrimidine metabolism, decrease inosine levels, decrease uridine levels, and/or increase orotate levels in an assay (e.g., an in vitro cell assay or an in vivo assay).

In some embodiments, the methods and compositions of the invention include malate, or a derivative thereof, and one or more antineoplastic agents (e.g., as described herein).

In some embodiments, the methods and compositions of the invention include malate, or a derivative thereof, and one or more glycolysis inhibitors (e.g., any described herein).

In some embodiments, the methods and compositions of the invention include malate, or a derivative thereof, and one or more antiangiogenic agents (e.g., any described herein).

In some embodiments, the methods and compositions of the invention include malate, or a derivative thereof, and one or more immunomodulatory agents (e.g., any described herein).

In some embodiments, the methods and compositions of the invention include malate, or a derivative thereof, and one or more antibodies (e.g., any described herein).

In some embodiments, the methods and compositions of the invention include malate, or a derivative thereof, and one or more cytokines (e.g., any described herein).

In one aspect, the invention features a method of treating (e.g., prophylactically) a subject having a proliferative disorder, the method includes administering to the subject (e.g., a human subject) a sufficient amount of a composition that increases the level of malate, or a derivative thereof, thereby treating the disorder (e.g., cancer, such as a non-solid or a solid cancer). In some embodiments, the increase in level of malate, or a derivative thereof, is an increase of at least 2-fold (e.g., from about 2-fold to about 150-fold, e.g., from 5-fold to 150-fold, from 5-fold to 100-fold, from 10-fold to 150-fold, from 10-fold to 100-fold, from 50-fold to 150-fold, from 50-fold to 100-fold, from 75-fold to 150-fold, or from 75-fold to 100-fold) or an increase of at least 5% (e.g., at least about 10%, 25%, 50%, 75%, 100%, 150%, 200%, 300%, 500%, 750%, or more, or from about 5% to 10%, 5% to 25%, 5% to 50%, 5% to 75%, 5% to 100%, 5% to 150%, 5% to 200%, 5% to 300%, 5% to 500%, 5% to 750%, 5% to 1000%, 10% to 25%, 10% to 50%, 10% to 75%, 10% to 100%, 10% to 150%, 10% to 200%, 10% to 300%, 10% to 500%, 10% to 750%, 10% to 1000%, 25% to 50%, 25% to 75%, 25% to 100%, 25% to 150%, 25% to 200%, 25% to 300%, 25% to 500%, 25% to 750%, 25% to 1000%, 50% to 75%, 50% to 100%, 50% to 150%, 50% to 200%, 50% to 300%, 50% to 500%, 50% to 750%, and 50% to 1000%), as compared to a control or a normal reference sample. In some embodiments, the level of malate, or a derivative thereof, is an extracellular level or an intercellular level.

In another aspect, the invention features a method of treating (e.g., prophylactically) a subject having a proliferative disorder, the method includes administering to the subject (e.g., a human subject) a sufficient amount of a composition comprising malate, or a derivative thereof, thereby treating the disorder (e.g., cancer, such as a non-solid or a solid cancer).

In any of the embodiments described herein, the composition includes malate, or a derivative thereof (e.g., selected from the group of malate, dimethyl malate, monomethyl hydrogen malate, diethyl malate, monoethyl hydrogen malate, and diisopropyl malate, or pharmaceutically acceptable salts thereof, or any described herein).

In any of the embodiments described herein, the malate, or the derivative thereof, has Formula (I):

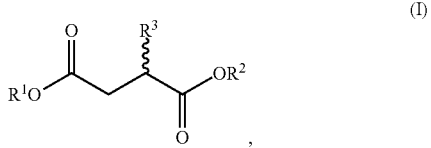

or a pharmaceutically acceptable salt or isomer (e.g., a D-isomer, an L-isomer, or a DL-isomer) thereof, where each $R^1$ and $R^2$ is, independently, H, optionally substituted $C_{1-30}$ alkyl (e.g., $C_{1-10}$ or $C_{1-6}$ alkyl), optionally substituted $C_{2-30}$ alkenyl (e.g., $C_{2-10}$ or $C_{2-6}$ alkenyl), optionally substituted $C_{2-30}$ alkynyl (e.g., $C_{2-10}$ or $C_{2-6}$ alkynyl), or optionally substituted $C_{1-30}$ haloalkyl (e.g., $C_{1-10}$ or $C_{1-6}$ haloalkyl); and $R^3$ is hydroxy, optionally substituted $C_{1-30}$ alkoxy (e.g., $C_{1-10}$ or $C_{1-6}$ alkoxy), optionally substituted $C_{1-30}$ haloalkoxy (e.g., $C_{1-10}$ or $C_{1-6}$ haloalkoxy), optionally substituted $C_{1-30}$ alkyl (e.g., $C_{1-10}$ or $C_{1-6}$ alkyl), optionally substituted $C_{2-30}$ alkenyl(e.g., $C_{2-10}$ or $C_{2-6}$ alkenyl), optionally substituted $C_{2-30}$ alkynyl (e.g., $C_{2-10}$ or $C_{2-6}$ alkynyl), optionally substituted $C_{1-30}$ haloalkyl (e.g., $C_{1-10}$ or $C_{1-6}$ haloalkyl), thiol, or optionally substituted $C_{1-30}$ thioalkoxy (e.g., $C_{1-10}$ or $C_{1-6}$ thioalkoxy).

In some embodiments, each $R^1$ and $R^2$ is, independently, optionally substituted $C_{1-6}$ alkyl (e.g., unsubstituted $C_{1-6}$ alkyl, e.g., methyl, ethyl, n-propyl, isopropyl, n-butyl, sec-butyl, iso-butyl, or tert-butyl). In particular embodiments, $R^1$ and $R^2$ are the same. In other embodiments, $R^1$ and $R^2$ are different.

In some embodiments, $R^3$ is hydroxy, optionally substituted $C_{1-30}$ alkoxy (e.g., $C_{1-10}$ or $C_{1-6}$ alkoxy), optionally substituted $C_{1-30}$ haloalkoxy (e.g., $C_{1-10}$ or $C_{1-6}$ haloalkoxy), optionally substituted $C_{1-30}$ alkyl (e.g., $C_{1-10}$ or $C_{1-6}$ alkyl), or optionally substituted $C_{1-30}$ haloalkyl (e.g., $C_{1-10}$ or $C_{1-6}$ haloalkyl).

In some embodiments, $R^3$ does not include a sulfur atom.

In some embodiments, each $R^1$ and $R^2$ is, independently, H, optionally substituted $C_{1-30}$ alkyl (e.g., $C_{1-10}$ or $C_{1-6}$ alkyl), or optionally substituted $C_{1-30}$ haloalkyl (e.g., $C_{1-10}$ or $C_{1-6}$ haloalkyl); and $R^3$ is hydroxy, optionally substituted $C_{1-30}$ alkoxy (e.g., $C_{1-10}$ or $C_{1-6}$ alkoxy), optionally substituted $C_{1-30}$ haloalkoxy (e.g., $C_{1-10}$ or $C_{1-6}$ haloalkoxy), optionally substituted $C_{1-30}$ alkyl (e.g., $C_{1-10}$ or $C_{1-6}$ alkyl), or substituted $C_{1-30}$ haloalkyl (e.g., $C_{1-10}$ or $C_{1-6}$ haloalkyl).

In some embodiments, the composition is administered parenterally (e.g., by intravenous, intramuscular, or subcutaneous injection).

In any of the embodiments described herein, the method further includes administering to the subject a malic enzyme 2 inhibitor (e.g., any described herein). In some embodiments, the malate, or the derivative thereof, and the malic enzyme 2 inhibitor are together in an amount sufficient to treat the proliferative disorder. In particular embodiments, the malate, or the derivative thereof, and the malic enzyme 2 inhibitor act synergistically.

In any of the embodiments described herein, the method further includes administering to the subject an antineoplastic agent (e.g., any described herein). In some embodiments, the malate, or the derivative thereof, and the antineoplastic agent are together in an amount sufficient to treat the proliferative disorder. In particular embodiments, the malate, or the derivative thereof, and the antineoplastic agent act synergistically.

In any of the embodiments described herein, the method further includes administering to the subject a glycolysis inhibitor (e.g., any described herein). In some embodiments, the malate, or the derivative thereof, and the glycolysis inhibitor are together in an amount sufficient to treat the proliferative disorder. In particular embodiments, the malate, or the derivative thereof, and the glycolysis inhibitor act synergistically.

In any of the embodiments described herein, the method further includes administering to the subject a therapeutic agent (such as an antiangiogenic agent, an immunomodulatory agent, an antibody, or a cytokine, e.g., any described herein). In some embodiments, the malate, or the derivative thereof, and the therapeutic agent are together in an amount sufficient to treat the proliferative disorder. In particular embodiments, the malate, or the derivative thereof, and the therapeutic agent act synergistically.

The invention also features a composition including malate, or a derivative thereof, in combination with one or more therapeutic agent (e.g., a malic enzyme 2 inhibitor, an antineoplastic agent, a glycolysis inhibitor, an antiangiogenic agent, an immunomodulatory agent, an antibody, or a cytokine, e.g., any described herein). In particular embodiments, malate, or a derivative thereof, and the therapeutic agent act synergistically. In some embodiments, including malate, or a derivative thereof, in combination with one or more therapeutic agents are together present in an amount sufficient to treat a proliferative disorder (e.g., cancer).

In some embodiments, the composition includes malate, or a derivative thereof, in combination with a malic enzyme 2 inhibitor. In particular embodiments, malate, or a derivative thereof, and the malic enzyme 2 inhibitor act synergistically.

In other embodiments, the composition includes malate, or a derivative thereof, in combination with an antineoplastic agent. In particular embodiments, malate, or a derivative thereof, and the antineoplastic agent act synergistically.

In other embodiments, the composition includes malate, or a derivative thereof, in combination with a glycolysis inhibitor. In particular embodiments, malate, or a derivative thereof, and the glycolysis inhibitor act synergistically.

In some embodiments, the composition includes malate, or a derivative thereof, in combination with a malic enzyme 2 inhibitor, an antineoplastic agent, and/or a glycolysis inhibitor are together present in an amount sufficient to treat a proliferative disorder (e.g., cancer). In particular embodiments, malate, or a derivative thereof, the malic enzyme 2 inhibitor, the antineoplastic agent, and the glycolysis inhibitor act synergistically.

The invention also features a composition including two or more of malate, or a derivative thereof, e.g., any described herein. In particular embodiments, the two or more of malate, or a derivative thereof, act synergistically.

In another aspect, the invention features a kit including a composition including malate, or a derivative thereof (e.g., any described herein); and one or more of a malic enzyme 2 inhibitor, an antineoplastic agent, and a glycolysis inhibitor (e.g., any described herein).

In another aspect, the invention features a method for diagnosing a subject as having, or having a predisposition to, a disease having an increased activation of malic enzyme 2 (e.g., a proliferative disorder, such as cancer or any described herein), the method including: determining the level of malate, or a derivative thereof, in a sample from the subject (e.g., a human subject); comparing the level of malate, or a derivative thereof, with a normal reference sample; diagnosing the subject, where the presence of a decreased level of malate, or a derivative thereof, as compared to the normal reference sample (e.g., a decreased level of at least 2-fold, e.g., from about 2-fold to about 150-fold, e.g., from 5-fold to 150-fold, from 5-fold to 100-fold, from 10-fold to 150-fold, from 10-fold to 100-fold, from 50-fold to 150-fold, from 50-fold to 100-fold, from 75-fold to 150-fold, or from 75-fold to 100-fold, or a decreased level of 5%, 10%, 25%, 50%, 75%, 100%, 150%, 200%, 300%, 500%, 750%, or more, as compared to a control or a normal reference sample), results in diagnosing the subject as having, or having a predisposition to, the disease; and optionally administering to the subject a sufficient amount of a composition including malate, or a derivative thereof. In some embodiments, the method comprises administering the composition including malate, or a derivative thereof.

In yet another aspect, the invention features a method for identifying a malate derivative for treating a proliferative disorder, the method including: contacting a cell or a malic enzyme in solution with a candidate compound; determining the level of malate, or a derivative thereof, in the cell or in the solution, and comparing the level of malate, or a derivative thereof, with a normal reference sample, where the presence of an increased level of malate, or a derivative thereof, in the cell or in the solution, as compared to the normal reference sample (e.g., an increased level of malate, or a derivative thereof, of at least 2-fold, e.g., from about 2-fold to about 150-fold, e.g., from 5-fold to 150-fold, from 5-fold to 100-fold, from 10-fold to 150-fold, from 10-fold to 100-fold, from 50-fold to 150-fold, from 50-fold to 100-fold, from 75-fold to 150-fold, or from 75-fold to 100-fold, or an increase of at least 5%, e.g., at least about 10%, 25%, 50%, 75%, 100%, 150%, 200%, 300%, 500%, 750%, or more, or from about 5% to 10%, 5% to 25%, 5% to 50%, 5% to 75%, 5% to 100%, 5% to 150%, 5% to 200%, 5% to 300%, 5% to 500%, 5% to 750%, 5% to 1000%, 10% to 25%, 10% to 50%, 10% to 75%, 10% to 100%, 10% to 150%, 10% to 200%, 10% to 300%, 10% to 500%, 10% to 750%, 10% to 1000%, 25% to 50%, 25% to 75%, 25% to 100%, 25% to 150%, 25% to 200%, 25% to 300%, 25% to 500%, 25% to 750%, 25% to 1000%, 50% to 75%, 50% to 100%, 50% to 150%, 50% to 200%, 50% to 300%, 50% to 500%, 50% to 750%, and 50% to 1000%, as compared to a control or a normal reference sample), results in identifying the candidate compound as the malate derivative.

For any of the methods or compositions described herein, the malic enzyme 2 inhibitor is an RNAi agent (e.g., an siRNA agent, an shRNA agent, a DsiRNA agent, and a miRNA agent, e.g., any of these agents that inhibits ME2 gene expression), S-oxalylglutathione or a derivative thereof, a lanthanide (e.g., lutetium, lanthanum, cerium, erbium, terbium, ytterbium, and holmium, as well as complexes thereof, such as lanthanide-labeled polyaminophosphonates, lanthanide-labeled antibodies, and lanthanide-labeled peptides), a steroid (e.g., pregnenolone), an anti-ME2 antibody (e.g., HPA008247 or HPA008880), a PI3K inhibitor (e.g., wortmannin, demethoxyviridin, LY294002, quercetin, myricetin, staurosporine, GDC-0941, NVP-BEZ235, ZSTK474, PX-866, XL-765, SF1126, BGT226, GDC-0941, and XL-147, e.g., wortmannin, e.g., LY294002), an RTK inhibitor (e.g., an EGFR inhibitor, an Her2 inhibitor, a PDGFR inhibitor, or an IGFR inhibitor, e.g., erlotinib, gefitinib, vandetanib, afatinib, axitinib, cediranib, cetuximab, lapatinib, lestaurtinib, neratinib, panitumumab, pazopanib, regorafenib, semaxanib, sorafenib, sunitinib, toceranib, trastuzumab, MK-0646, BIIB022, and AVE1642, e.g., erlotinib, e.g., gefitinib), a PDK1 inhibitor (e.g., OSU-03012 and celecoxib), an AKT inhibitor (e.g., A-443654, GSK690693, VQD-002 (triciribine), and perifosine), or an mTOR inhibitor (e.g., an mTOR1 inhibitor or an mTOR2 inhibitor, e.g., rapamycin (sirolimus) and modified rapamycins (rapalogs), such as CCI-779 (temsirolimus), and RAD001 (everolimus)), and dual inhibitors of any of these proteins (e.g., a dual PI3K/mTOR inhibitor, such as NVP-BEZ235 and PI-103, or a dual AKT/PDK1 inhibitor, such as 6H-indeno[1,2-e]tetrazolo[1,5-b][1,2,4]triazin-6-one, 10H-indeno[2,1-e]tetrazolo[1,5-b][1,2,4]triazin-10-one, and PHT-427). Additional ME2 inhibitors can be identified by any useful method (e.g., as described herein).

In particular embodiments, the RNAi agent includes a nucleic acid sequence substantially identical (e.g., at least 50%, 60%, 70%, 75%, 80%, 85%, 90%, 95%, 96%, 97%, 98%, 99%, or 100% identical) to the sequence of any one of SEQ ID NOs:7-42. In some embodiments, the RNAi agent includes a nucleic acid sequence of any one of SEQ ID NOs: 7-42.

For any of the methods or compositions described herein, the antineoplastic agent is one or more of a chemotherapeutic agent (e.g., arsenic trioxide, cisplatin, carboplatin, chlorambucil, melphalan, nedaplatin, oxaliplatin, triplatin tetranitrate, satraplatin, imatinib, nilotinib, dasatinib, and radicicol, e.g., cisplatin), an immunomodulatory agent (e.g., methotrexate, leflunomide, cyclophosphamide, cyclosporine A, minocycline, azathioprine, an antibiotic (e.g., tacrolimus), methylprednisolone, a corticosteroid, a steroid, mycophenolate mofetil, rapamycin, mizoribine, deoxyspergualin, brequinar, a T cell receptor modulator, and a cytokine receptor modulator, e.g., methotrexate), an antiangiogenic agent (e.g., alitretinoin, beloranib, bevacizumab, cetuximab, endostatin (e.g., recombinant forms thereof), erlotinib, etrathiomolybdate, everolimus, imiquimod, interferon alfa (e.g., recombinant forms thereof), itraconazole, lenalidomide, pazopanib, sorafenib, sunitinib, suramin, temsirolimus, thalidomide, tivozanib, vandetanib, and vatalanib), a mitotic inhibitor (e.g., paclitaxel, vinorelbine, docetaxel, abazitaxel, ixabepilone, larotaxel, ortataxel, tesetaxel, vinblastine, vincristine, vinflunine, and vindesine, e.g., paclitaxel), a nucleoside analog (e.g., gemcitabine, azacitidine, capecitabine, carmofur, cladribine, clofarabine, cytarabine, decitabine, floxuridine, fludarabine, fluorouracil, mercaptopurine, pentostatin, tegafur, and thioguanine, e.g., gemcitabine), a DNA intercalating agent (e.g., doxorubicin, actinomycin, bleomycin, mitomycin, and plicamycin, e.g., doxorubicin), a topoisomerase analog (e.g., irinotecan, aclarubicin, amrubicin, belotecan, camptothecin, daunorubicin, epirubicin, etoposide, idarubicin, mitoxantrone, pirarubicin, pixantrone, rubitecan, teniposide, topotecan, valrubicin, and zorubicin, e.g., irinotecan), an antibody (e.g., monoclonal antibodies, such as alemtuzumab, bevacizumab, brentuximab vedotin, catumaxomab, cetuximab, denosumab, edrecolomab, ertumaxomab, gemtuzumab ozogamicin, ibritumomab, ibritumomab tiuxetan, ipilimumab, ofatumumab, panitumumab, rituximab, tositumomab, trastuzumab, as well as radiolabeled forms thereof, or any described herein), a cytokine (e.g., recombinant interferon alpha, interferon beta, interferon gamma, interleukin 2, interleukin 11, granulocyte colony-stimulating factor (G-CSF) and pegylated forms thereof, granulocyte macrophage colony-stimulating factor (GM-CSF), and methionyl human stem cell factor (SCF), as well as any described herein), a folate antimetabolite (e.g., pemetrexed, aminopterin, methotrexate, pralatrexate, and raltitrexed, e.g., pemetrexed), or other targeting agents (e.g., agents that target particular enzymes or proteins involved in cancer or agents that target particular organs or types of cancers), and combinations thereof.

For any of the methods or compositions described herein, the glycolysis inhibitor is a hexokinase inhibitor (e.g., a hexokinase 2 (HK2) inhibitor (e.g., 2-deoxyglucose, halogenated derivatives of 2-deoxyglucose (e.g., 2-fluorodeoxyglucose), 5-thioglucose, 3-bromopyruvate (3-BrPA), 3-bromo-2-oxopropionate-1-propylester (3-BrOP), lonidamine, imatinib, meclofenoxate, O,O-diethyl O-3,5,6-trichloro-2-pyridyl phosphate, 7,8-dihydro-7,8-dihydroxybenzo(a)pyrene 9,10-oxide, antisense RNA, N-terminal oligopeptide of hexokinase II (e.g., MIASHLLAYFFTELN-amide (hexokinase II VDAC binding domain peptide; HXK2VBD, SEQ ID NO:1) and RQIKIWFQNRRMKWK-KMIASHLLAYFFTELN-amide (SEQ ID NO:2)), antifungal derivatives (e.g., clotrimazole and bifonazole), and D-mannoheptulose); a lactate dehydrogenase inhibitor (e.g., a lactate dehydrogenase A (LDH-A) inhibitor or a lactate dehydrogenase 5 (LDH-5) inhibitor (e.g., oxamate, gossypol, 3-hydroxyisoxazole-4-carboxylic acid (HICA), 4-hydroxy-1,2,5-thiadiazole-3-carboxylic acid (HTCA), 3-dihydroxy-6-methyl-7-(phenylmethyl)-4-propylnaphthalene-1-carboxylic acid (FX11), 7,8-dihydro-7,8-dihydroxybenzo(a)pyrene 9,10-oxide, cyclosporine, lindane, antisense RNA (e.g., shRNA, nt 204-232 (L1, gattaca gttgttgggg ttggtgctgt tg (SEQ ID NO:3)), nt 737-765 (L2, tgtg gagtggtgtg aatgt-tgccg gcgtc (SEQ ID NO:4)), and nt 1161-1188 (L3, tcact-gtcca ggctgcagca gggcttct (SEQ ID NO:5)) of NCBI Reference Sequence: NM_010699)), 1-hydroxy-5-phenyl-1H-indole-2-carboxylic acid, 1-hydroxy-6-phenyl-1H-indole-2-carboxylic acid, and 1-hydroxy-6-phenyl-4-trifluoromethyl-1H-indole-2-carboxylic acid); a phosphofructokinase 2 or phosphofructo-2-kinase/fructose-2,6-bisphosphatase (PFK2/PFKFB3) inhibitor (e.g., 3-(3-pyridinyl)-1-(4-pyridinyl)-2-propen-1-one); a pyruvate kinase M2 (PKM2) inhibitor (e.g., 4R,7S,10R,13S,16R)-7-(4-aminobutyl)-N-[(3R)-1-amino-3-hydroxy-1-oxobutan-2-yl]-16-[[(2R)-2-amino-3-phenylpropanoyl]amino]-13-[(4-hydroxyphenyl)methyl]-10-(1H-indol-3-ylmethyl)-6,9,12,15-tetraoxo-1,2-dithia-5,8,11,14-tetrazacycloheptadecane-4-carboxamide (TLN-232/CAP-232), shikonin, and alkannin); a transketolase inhibitor (e.g., a transketolase-like enzyme 1 (TKTL1) inhibitor (e.g., oxythiamine and furazolidone)); a pyruvate dehydrogenase (PDH) inhibitor (e.g., oxythiamine); a pyruvate dehydrogenase kinase (PDK) inhibitor (e.g., dichloroacetate); a glucose-6-phosphate dehydrogenase (G6PG) inhibitor (e.g., 6-aminonicotinamide, imatinib, 2,2'-azobis(2-amidinopropane), 2,5-dihydroxybenzoic acid, aluminum phosphide, arjunolic acid, benzo(a)pyrene, benzoyl peroxide, calphostin C, cycloartenol, dactinomycin, dexamethasone, diethylnitrosamine, endosulfan, fenvalerate, ferric nitrilotriacetate, ferrous sulfate, glyoxylic acid, furantoin, phenobarbitol, quercetin, isotretinoin, and streptozocin); a GLUT inhibitor (e.g., fluorodeoxyglucose, including radiolabelled forms ([18F]-fluorodeoxyglucose), 2-deoxyglucose, phloretin, and silybin/silibinin); a proton transport inhibitor, such as a carbonic anhydrase-9 (CA9) inhibitor, a membrane-bound V-ATPase inhibitor, and a sodium-proton exchanger 1 (NHE1) inhibitor (e.g., paclitaxel, acetazolamide, cariporide, indisulam, girentuximab, esomeprazole, amiloride and derivatives thereof (5-(N-ethyl-Nisopropyl)amiloride (EIPA)); a monocarboxylate transporter (MCT) inhibitor, such as MCT1, MCT2, MCT3, or MCT4 inhibitors (e.g., α-cyano-4-hydroxycinnamate (CHC), AZD3965, or AR-C117977); a hypoxia-inducible factor 1 alpha (HIF-1 alpha) inhibitor (e.g., BAY87-2243, acriflavine, PX-478, tirapazamine, and an antisense oligonucleotide targeting HIF-1α (EZN-2968, 5'-TGGcaagcatccTGTa-3', where upper case indicates LNA residues and lower case indicates DNA residues (SEQ ID NO: 6))); a c-Myc inhibitor (e.g., (5E)-5-[(4-ethylphenyl)methylidene]-2-sulfanylidene-1,3-thiazolidin-4-one (10058-F4) and quarfloxin/CX-3453); an AMP-activated protein kinase (AMPK) inhibitor (e.g., metformin); a glutamine inhibitor (e.g., phenylacetate); an asparagine inhibitor (e.g., asparaginase and pegasparaginase); an arginine inhibitor (e.g., arginine deaminase); a fatty acid synthase (FASN) inhibitor (e.g., orlistat, GSK837149A, and C75); and an ATP-citrate lyase (ACLY) inhibitor (e.g., 2-[(3S,5R)-5-[6-(2,4-dichlorophenyl)hexyl]-3-hydroxy-2-oxooxolan-3-yl]acetic acid (SB-204990), quercetin, and rutin).

In any of the embodiments described herein, the proliferative disorder is cancer, benign prostatic hyperplasia, psoriasis, Reiter's syndrome, pityriasis rubra pilaris, an abnormal keratinization disorder, scleroderma, a lymphoproliferative disorder, chronic rheumatoid arthritis, arteriosclerosis, atherosclerosis, restenosis, and diabetic retinopathy.

In any of the embodiments described herein, the cancer is selected from the group consisting of leukemia (e.g., chronic myeloid leukemia, acute myeloid leukemia, acute lymphoblastic leukemia, and chronic lymphocytic leukemia), brain cancer (e.g., ependymoma, glioma, medulloblastoma, meningioma, teratoid rhabdoid tumor, and teratoma), bladder cancer (e.g., adenocarcinoma, sarcoma, small cell carcinoma, squamous cell carcinoma, and transitional cell carcinoma), breast cancer (e.g., breast ductal carcinoma), cervical cancer, colorectal cancer, endometrial cancer, esophageal cancer (e.g., adenocarcinoma and squamous cell carcinoma), head and neck cancer, liver cancer (e.g., hepatocellular carcinoma, cholangiocarcinoma, and hemangioendothelioma), lung cancer (e.g., non-small cell lung cancer, small-cell lung cancer, carcinoid, sarcoma, squamous cell cancer, adenocarcinoma, adenosquamous cell cancer, spindle cell carcinoma, and large cell carcinoma), lymphoma (e.g., malignant lymphoma), ovarian cancer (e.g., ovarian epithelial carcinoma and teratoma), pancreatic cancer, prostate cancer (e.g., adenocarcinoma and prostatic intraepithelial neoplasia), renal cancer, skin cancer (e.g., basal cell carcinoma, squamous cell carcinoma, and malignant melanoma), stomach cancer, testis cancer, thyroid cancer, and urothelial cancer. In particular embodiments, the cancer has one or more mutations, such as non-small cell lung cancer having a T790M or a L747S mutation in EGFR kinase, a somatic activating mutation in the tyrosine-kinase pocket of EGFR (e.g., a deletion in exon 19 or a substitution in exon 21, e.g., L858R), a deletion in the p14ARF locus, a mutation in the tumor suppressor gene LKB1 (e.g., exon 2-3del, exon 4del, exon 6del, D176Y, D194Y, D277Y, P281L, R426W, S69X, Q159X), a mutation in the oncogene KRAS, or a mutation present in tyrosine kinase inhibitor-resistant cell line H1975; and brain cancer, breast cancer, colorectal cancer, lung cancer, or stomach cancer having a E542K, E545K, H1047R, P539R, or H1047L mutation in the PIK3CA gene (encoding a p110α of class IA of PI3K) (e.g., lung cancer having a H1047R mutation in PIK3CA).

The invention also features methods, compositions, and diagnostic tests for diagnosing cancer and other diseases that result from increased activation of ME2. The diagnostic methods and tests could aid in identifying patients who are at risk of developing cancer related to ME2 activity. The methods described herein can be used to identify patients who are at risk by determining the activity of ME2 (e.g., by using any of the methods described herein). The methods described herein can be used to identify patients with increased ME2 activity and to treat these patients by using any of the methods or compositions described herein.

In particular embodiments, a diagnostic test or method is used to predict the risk of a patient in developing cancer (e.g., leukemia). A diagnostic test or method can include a screen for the activity of ME2 by any useful detection method (e.g., fluorescence, radiation, or spectrophotometry). A diagnostic test can further include probes and primers to detect the expression of the ME2 gene. In certain embodiments, the diagnostic test includes the use of the activity of ME2 in a diagnostic platform, which can be optionally automated. Further, the diagnostic tests disclosed herein can be used to determine an optimal treatment plan for a patient. For example, the presence of increased activity of ME2 includes a treatment plan of administering an ME2 inhibitor.

Other features and advantages of the invention will be apparent from the following description and the claims.

Definitions

As used herein, the term "about" means ±10% of the recited value.

By "amount sufficient" of an agent is meant the amount of the agent sufficient to effect beneficial or desired results, such as clinical results, and, as such, an amount sufficient depends upon the context in which it is applied. For example, in the context of administering a composition that increases the level of malate, or a derivative thereof, the amount sufficient of the formulation is an amount sufficient to achieve an increase in levels of malate, or a derivative thereof (e.g., an extracellular and/or an intracellular level), and/or to achieve a reduction in the expression level of the ME2 gene or protein, as compared to the response obtained without administration of the composition.

By "decreases the level of malate, or a derivative thereof," is meant a decrease in at least one of malate, a derivative of malate, or a metabolite of any of these. For example, when the derivative is dimethyl malate, then the metabolite can be malate, monomethylhydrogen malate, or any other fragment of the metabolite (e.g., as determined by mass spectrometry). The decrease may be a decrease of at least 5%, 10%, 25%, 50%, 75%, 100%, 150%, 200%, 300%, 500%, 750%, 1000%, 2500%, 5000%, 10,000%, 50,000%, or 100,000%, as compared to a relevant control (e.g., a level of malate, or a derivative thereof, in a normal cell, in normal tissue, in a cell or tissue from a normal subject, or in a cell or tissue previously obtained from the same subject prior to treatment with a composition, where the level can be an extracellular or an intracellular level).

By "derivative" of malate is meant a compound having a core structure of malate and one or more additional modifications that allow for an increase in the level of malate, or a derivative thereof, as defined herein. Exemplary, non-limiting chemical modifications include replacement of one atom for another atom having the same or similar size, steric, hydrophobic, hydrophilic, and/or electrostatic properties; addition of one or more linkers between functional groups in the core structure of malate, such as an alkylene, polyethylene glycol, nucleic acid, amino acid, or peptide; and replacement of one functional group with another functional group, such as a replacement between any one of alkyl, alkoxy, amino, aminoalkyl, thioalkoxy, thio, haloalkyl, alkenyl, alkenyl, cycloalkyl, and heterocyclyl. Additional derivatives include, e.g., compounds of Formula (I), as described herein, as well as structural analogs, homologs, and isomers of malate, a derivative thereof, or compounds of Formula (I).

By "Dicer-substrate RNA" or "DsiRNA" is meant a class of 25-35 (e.g., 25-27, such as 27) nucleotide double-stranded molecules that are capable of gene silencing. Due to its longer length compared to other RNAi agents, DsiRNA are likely substrates of Dicer.

By "double-stranded molecule" is meant a double-stranded RNA:RNA or RNA:DNA molecule that can be used to silence a gene product through RNA interference.

By "expression" is meant the detection of a gene or polypeptide by methods known in the art. For example, DNA expression is often detected by Southern blotting or polymerase chain reaction (PCR), and RNA expression is often detected by Northern blotting, RT-PCR, gene array technology, or RNAse protection assays. Methods to measure protein expression level generally include, but are not limited to, Western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microscopy, fluorescence activated cell sorting (FACS), and flow cytometry, as well as assays based on a property of the protein including, but not limited to, enzymatic activity or interaction with other protein partners.

By "hybridize" is meant to pair to form a double-stranded molecule between sufficiently complementary polynucleotides, as defined herein, or portions thereof, under various conditions of stringency. (See, e.g., Wahl et al., *Methods Enzymol.* 152:399 (1987); Kimmel, *Methods Enzymol.* 152: 507 (1987)). For example, high stringency salt concentration will ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide or at least about 50% formamide. High stringency temperature conditions will ordinarily include temperatures of at least about 30° C., 37° C., or 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In an alternative embodiment, hybridization will occur at 50° C. or 70° C. in 400 mM NaCl, 40 mM PIPES, and 1 mM EDTA, at pH 6.4, after hybridization for 12-16 hours, followed by washing. Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. Useful variations on these conditions will be readily apparent to those skilled in the art.

By "increases the level of malate, or a derivative thereof," is meant an increase in at least one of malate, a derivative of malate, or a metabolite of any of these. For example, when the derivative is dimethyl malate, then the metabolite can be malate, monomethylhydrogen malate, or any other fragment of the metabolite (e.g., as determined by mass spectrometry). The increase may be an increase of at least 5%, 10%, 25%, 50%, 75%, 100%, 150%, 200%, 300%, 500%, 750%, 1000%, 2500%, 5000%, 10,000%, 50,000%, or 100,000%, as compared to a relevant control (e.g., a level of malate, or a derivative thereof, in a normal cell, in normal tissue, in a cell or tissue from a normal subject, or in a cell or tissue previously obtained from the same subject prior to treatment with a composition, where the level can be an extracellular and/or an intracellular level).

By "increased activity" or "increased activation" of ME2 is meant an increase in ME2 gene expression, protein expression, or enzymatic activity, as compared to a control from a normal cell or normal tissue (e.g., an increase of at least 2-fold, e.g., from about 2-fold to about 150-fold, e.g., from 5-fold to 150-fold, from 5-fold to 100-fold, from 10-fold to 150-fold, from 10-fold to 100-fold, from 50-fold to 150-fold, from 50-fold to 100-fold, from 75-fold to 150-fold, or from 75-fold to 100-fold, as compared to a control or a normal reference sample). Increased activity can be determined using any useful methods known in the art or described herein. For example, an increase in activity can be determined as an increase in ME2 gene expression or increased ME2 protein concentration (e.g., as determined by PCR or by gel electrophoresis), as compared to a control (e.g., a sample including normal cell or normal tissue from one or more healthy subjects) or a normal reference sample, as defined herein. In another example, an increase in activity can be determined as an increase in ME2 enzymatic activity, such as by measuring increased NADH formation (e.g., from 3-fold to 4-fold increased formation), increased NADPH formation (e.g., from 5-fold to 10-fold, e.g., about 7 fold, increased formation), decreased $NAD^+$/NADH ratio (e.g., from 1.5-fold to 3-fold, e.g., about 2-fold, decreased ratio), or decreased $NADP^+$/NADPH ratio (e.g., from 5-fold to 15-fold, e.g., about 9-fold, decreased ratio), as compared to a control or a normal reference sample. Increased activity can be measured directly (e.g., increased ME2 gene expression or increased ME2 enzymatic activity) or indirectly, such as by measuring levels of one or more analytes associated with increased ME2 activity (e.g., by measuring one or more of decreased ROS activity, increased ATP levels (e.g., from 2-fold to 4-fold, e.g., about 3-fold, increased levels), activation of phospho-ERK1/2, deactivation of phospho-AKT, decreased GATA-1 expression, increased vimentin expression, decreased apoptosis, increased proliferation, increased pyrimidine metabolism, increased inosine levels (e.g., from 5-fold to 10-fold, e.g., about 6-fold, increased levels), increased uridine levels (e.g., from 5-fold to 10-fold, e.g., about 6-fold, increased levels), or decreased orotate levels (e.g., from 50-fold to 150-fold, e.g., from 75-fold to 150-fold, e.g., about 90-fold, decreased levels), as compared to a control or a normal reference sample.

By "malic enzyme 2 inhibitor" or "ME2 inhibitor" is meant any agent or compound that decreases or reduces ME2 gene expression, protein expression, or enzymatic activity, as defined herein, compared to a control (e.g., a decrease by 5%, 10%, 15%, 20%, 25%, 30%, 35%, 40%, 45%, 50%, 55%, 60%, 65%, 70%, 75%, 80%, 85%, 90%, or 95%, as compared to a control or a normal reference sample). ME2 inhibitors can be identified and tested by any useful method (e.g., any described herein). ME2 includes *Homo sapiens* mRNA (NCBI RefSeq no. NM_002396.4 and Entrez Gene No. 4200), *Homo sapiens* DNA (NCBI RefSeq nos. NC_000018.9 and NT_010966.14), and *Homo sapiens* protein (UniProtKB reference no. P23368 and NCBI RefSeq nos. NP_001161807.1 and NP_002387.1).

By "microRNA" (miRNA) is meant a single-stranded RNA molecule that can be used to silence a gene product through RNA interference.

By "modulate" is meant that the expression of a gene, or level of an RNA molecule or equivalent RNA molecules encoding one or more proteins or protein subunits, or activity of one or more proteins or protein subunits is up-regulated or down-regulated, such that expression, level, or activity is greater than or less than that observed in the absence of the modulator. For example, the term modulate can include inhibition or gene silencing, and the level of expression of a gene or the level of an RNA molecule, or an equivalent thereof, is reduced by at least 10% (e.g., 15%, 20%, 25%, 30%, 35%, 40%, 50%, 60%, 70%, 80%, 85%, 90%, 95%, 97%, 98%, 99%, or 100%), as compared to a control.

By "pharmaceutical composition" is meant a composition containing a compound described herein formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

By "pharmaceutically acceptable excipient" is meant any ingredient other than the compounds described herein (for example, a vehicle capable of suspending or dissolving the active compound) and having the properties of being non-toxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

By "pharmaceutically acceptable salt" is meant those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharm. Sci.* 66(1):1, 1977 and in *Pharmaceutical Salts: Properties, Selection, and Use*, P. H. Stahl and C. G. Wermuth (eds.), Wiley-VCH, 2008. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, and the like.

By "reference sample" is meant any sample, standard, standard curve, or level that is used for comparison purposes. A "normal reference sample" can be, for example, a prior sample taken from the same subject; a sample from a normal healthy subject; a sample from a subject not having a disease associated with a decreased level of malate, or a derivative thereof, e.g., cancer; a sample from a subject that is diagnosed with a propensity to develop a disease associated with decreased levels of malate, or a derivative thereof, e.g., cancer, but does not yet show symptoms of the disorder; a sample from a subject that has been treated for a disease associated with decreased levels of malate, or a derivative thereof, e.g., cancer; or a sample of malate, or a derivative thereof, at a known normal concentration. By "reference standard or level" is meant a value or number derived from a reference sample. A normal reference standard or level can be a value or number derived from a normal subject who does not have a disease associated with decreased levels of malate, or a derivative thereof, e.g., cancer. In preferred embodiments, the reference sample, standard, or level is matched to the sample subject by at least one of the following criteria: age, weight, sex, disease stage, and overall health. A standard curve of levels of a malate, or a derivative thereof, within the normal reference range can also be used as a reference.

By "RNAi agent" is meant any agent or compound that exerts a gene silencing effect by hybridizing a target nucleic acid. RNAi agents include any nucleic acid molecules that are capable of mediating sequence-specific RNAi (e.g., under stringent conditions), for example, a short interfering RNA (siRNA), double-stranded RNA (dsRNA), microRNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and Dicer-substrate RNA (DsiRNA).

By "sense region" is meant a nucleotide sequence having sufficient complementarity to an antisense region of another nucleic acid. In addition, the sense region of a nucleic acid of the invention can include a nucleotide sequence having homology with a target gene nucleotide sequence. By "antisense region" is meant a nucleotide sequence having sufficient complementarity to a target gene nucleotide sequence.

By "short hairpin RNA" or "shRNA" is meant a sequence of RNA that makes a tight hairpin turn and is capable of gene silencing.

By "silencing" or "gene silencing" is meant that the expression of a gene or the level of an RNA molecule that encodes one or more proteins is reduced in the presence of an RNAi agent below that observed under control conditions (e.g., in the absence of the RNAi agent or in the presence of an inactive or attenuated molecule such as an RNAi molecule with a scrambled sequence or with mismatches). Gene silencing may decrease gene product expression by 1%, 2%, 3%, 4%, 5%, 6%, 7%, 8%, 9%, 10%, 15%, 20%, 25%, 30%, 35%, 40%, 50%, 60%, 70%, 80%, 85%, 90%, 95%, 97%, 98%, 99%, or 100% (i.e., complete inhibition).

By "small inhibitory RNA," "short interfering RNA," or "siRNA" is meant a class of 10-40 (e.g., 15-25, such as 21) nucleotide double-stranded molecules that are capable of gene silencing. Most notably, siRNA are typically involved in the RNA interference (RNAi) pathway by which the siRNA interferes with the expression of a specific gene product.

By "subject" is meant a mammal (e.g., a human).

By "substantial identity" or "substantially identical" is meant a polypeptide or polynucleotide sequence that has the same polypeptide or polynucleotide sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least 50%, 60%, 70%, 75%, 80%, 85%, 90%, 95%, 96%, 97%, 98%, 99%, or 100% identity to the reference amino acid sequence. For polypeptides, the length of comparison sequences will generally be at least 5, 6, 7, 8, 9, 10, 11, 12, 13, 14, 15, 16, 17, 18, 19, or 20 contiguous amino acids, more preferably at least 25, 50, 75, 90, 100, 150, 200, 250, 300, or 350 contiguous amino acids, and most preferably the full-length amino acid sequence. For nucleic acids, the length of comparison sequences will generally be at least 5 contiguous nucleotides, preferably at least 10, 11, 12, 13, 14, 15, 16, 17, 18, 19, 20, 21, 22, 23, 24, or 25 contiguous nucleotides, and most preferably the full length nucleotide sequence. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

By "sufficiently complementary" is meant a polynucleotide sequence that has the exact complementary polynucleotide sequence, as a target nucleic acid, or has a specified percentage or nucleotides that are the exact complement at the corresponding location within the target nucleic acid when the two sequences are optimally aligned. For example, a polynucleotide sequence that is "substantially complementary" to a target nucleic acid sequence has at least 50%, 60%, 70%, 75%, 80%, 85%, 90%, 95%, 96%, 97%, 98%, 99%, or 100% complementarity to the target nucleic acid sequence. For RNAi agents having a length between 10 to 40 nucleotides, sufficiently complementary sequences include those having one, two, three, four, or five non-complementary nucleotides.

By "target nucleic acid" is meant any nucleic acid sequence whose expression or activity is to be modulated. The target nucleic acid can be DNA or RNA.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilization (i.e., not worsening) of a state of disease, disorder, or condition; prevention of spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment. By "treating" or "inhibiting" cancer or a proliferative disorder is meant causing a reduction in the size of a tumor or the number of proliferating (e.g., cancerous) cells, slowing or inhibiting an increase in the size of a tumor or cell proliferation, increasing the disease-free survival time between the disappearance of a tumor or proliferative disorder (e.g., cancer) and its reappearance, reducing the likelihood of an initial or subsequent occurrence of a tumor or proliferative disorder (e.g., cancer), or reducing an adverse symptom associated with a tumor or proliferative disorder (e.g., cancer). In a desired embodiment, the percent of tumor or proliferating (e.g., cancerous) cells surviving the treatment is at least 20, 40, 60, 80, or 100% lower than the initial number of tumor or proliferating (e.g., cancerous) cells, as measured using any standard assay. Desirably, the decrease in the number of tumor or proliferating (e.g., cancerous) cells induced by administration of a compound of the invention is at least 2, 5, 10, 20, or 50-fold greater than the decrease in the number of non-tumor or non-cancerous cells. Desirably, the methods of the present invention result in a decrease of 20, 40, 60, 80, or 100% in the size of a tumor or number of proliferating (e.g., cancerous) cells, as determined using standard methods. Desirably, at least 20, 40, 60, 80, 90, or 95% of the treated subjects have a complete remission in which all evidence of the tumor or cancer disappears. Desirably, the tumor or cancer does not reappear or reappears after no less than 5, 10, 15, or 20 years. By "prophylactically treating" or "preventing" a disease or condition (e.g., cancer) in a subject is meant reducing the risk of developing (i.e., the incidence) of or reducing the severity of the disease or condition prior to the appearance of disease symptoms. The prophylactic treatment may completely prevent or reduce appears of the disease or a symptom thereof and/or may be therapeutic in terms of a partial or complete cure for a disease and/or adverse effect attributable to the disease. Prophylactic treatment may include reducing or preventing a disease or condition (e.g., preventing cancer) from occurring in an individual who may be predisposed to the disease but has not yet been diagnosed as having it.

The prefix "alk-" or the term "alkylene," as used herein, represent a saturated divalent hydrocarbon group derived from a straight or branched chain saturated hydrocarbon by the removal of two hydrogen atoms, and is exemplified by methylene, ethylene, isopropylene, and the like. The term "$C_{x-y}$ alkylene" and the prefix "$C_{x-y}$ alk-" represent alkylene groups having between x and y carbons. Exemplary values for x are 1, 2, 3, 4, 5, and 6, and exemplary values for y are 2, 3, 4, 5, 6, 7, 8, 9, or 10. In some embodiments, the alkylene can be further substituted with 1, 2, 3, or 4 substituent groups as defined herein for an alkyl group.

The term "alkaryl," as used herein, represents an aryl group, as defined herein, attached to the parent molecular group through an alkylene group, as defined herein.

The term "alkenyl," as used herein, represents monovalent straight or branched chain groups of, unless otherwise specified, from two to thirty carbons containing one or more carbon-carbon double bonds and is exemplified by ethenyl, 1-propenyl, 2-propenyl, 2-methyl-1-propenyl, 1-butenyl, 2-butenyl, and the like. In particular embodiments, alkenyl is $C_{2-10}$ alkenyl or $C_{2-6}$ alkenyl. Alkenyl groups may be optionally substituted with 1, 2, 3, or 4 substituent groups (e.g., any of the exemplary alkyl substituent groups described herein).

The term "alkheterocyclyl" represents a heterocyclyl group, as defined herein, attached to the parent molecular group through an alkylene group, as defined herein.

The term "alkoxy" represents a chemical substituent of formula —OR, where R is a $C_{1-30}$ alkyl group (e.g., $C_{1-10}$ alkyl or $C_{1-6}$ alkyl). In some embodiments, the alkyl group can be further substituted with 1, 2, 3, or 4 substituent groups as defined herein.

The term "alkyl," as used herein, is inclusive of both straight chain and branched chain saturated groups from 1 to 30 carbons, unless otherwise specified. In particular embodiments, alkyl is $C_{1-10}$ alkyl or $C_{1-6}$ alkyl. Alkyl groups are exemplified by methyl, ethyl, n- and isopropyl, n-, sec-, iso- and tert-butyl, neopentyl, and the like, and may be optionally substituted with one, two, three, or, in the case of alkyl groups of two carbons or more, four substituents independently selected from the group consisting of: (1) $C_{1-6}$ alkoxy; (2) $C_{1-6}$ alkylsulfinyl, which represents an alkyl group attached to the parent molecular group through an —S(O)— group; (3) amino, which represents —N($R^{N1}$)$_2$, wherein each $R^{N1}$ is, independently, H, an N-protecting group, $C_{1-6}$ alkyl, $C_{2-6}$ alkenyl, $C_{2-6}$ alkynyl, $C_{1-6}$ alkoxy, $C_{6-10}$ aryl, $C_{1-6}$ alk-$C_{6-10}$ aryl, $C_{3-8}$ cycloalkyl, $C_{1-6}$ alk-$C_{3-8}$ cycloalkyl, $C_{1-12}$ heterocyclyl (e.g., $C_{1-12}$ heteroaryl), $C_{1-6}$ alk-$C_{1-12}$ heterocyclyl (e.g., $C_{1-6}$ alk-$C_{1-12}$ heteroaryl), or two $R^{N1}$ combine to form a $C_{1-12}$ heterocyclyl or an N-protecting group, and wherein each $R^{N2}$ is, independently, H, $C_{1-6}$ alkyl, or $C_{6-10}$ aryl; (4) $C_{6-10}$ aryl-$C_{1-6}$ alkoxy; (5) azido; (6) halo; (7) ($C_{2-9}$ heterocyclyl)oxy; (8) hydroxy; (9) nitro; (10) oxo (e.g., carboxyaldehyde or acyl); (11) $C_{1-7}$ spirocyclyl; (12) $C_{1-6}$ thioalkoxy; (13) thiol; (14) —CO$_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (15) —C(O)NR$^{B'}$R$^{C'}$, where each of $R^{B'}$ and $R^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —SO$_2R^{D'}$, where $R^{D'}$ is selected from the group consisting of (a) $C_{1-6}$ alkyl, (b) $C_{6-10}$ aryl, and (c) $C_{1-6}$ alk-$C_{6-10}$ aryl; and (17) —SO$_2$NR$^{E'}$R$^{F'}$, where each of $R^{E'}$ and $R^{F'}$ is, independently, selected from the group consisting of (a)

hydrogen, (b) $C_{1-6}$ alkyl, (c) $C_{6-10}$ aryl and (d) $C_{1-6}$ alk-$C_{6-10}$ aryl. In some embodiments, each of these groups can be further substituted as described herein. For example, the alkylene group of a $C_1$-alkaryl can be further substituted with an oxo group (i.e., =O) to afford the respective aryloyl substituent.

The term "alkynyl," as used herein, represents monovalent straight or branched chain groups from two to thirty carbon atoms containing a carbon-carbon triple bond and is exemplified by ethynyl, 1-propynyl, and the like. In particular embodiments, alkynyl is $C_{2-10}$ alkynyl or $C_{2-6}$ alkynyl. Alkynyl groups may be optionally substituted with 1, 2, 3, or 4 substituent groups (e.g., any of the exemplary alkyl substituent groups described herein).

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, fluorenyl, indanyl, indenyl, and the like. Aryls can be optionally substituted with one, two, three, four, five, or more substituents (e.g., as described herein for alkyl).

The term "halo," as used herein, represents a halogen selected from bromine, chlorine, iodine, or fluorine.

The term "haloalkoxy," as used herein, represents an alkoxy group, as defined herein, substituted by a halogen group (i.e., F, Cl, Br, or I). A haloalkoxy may be substituted with one, two, three, or, in the case of alkyl groups of two carbons or more, four halogens. Haloalkoxy groups include perfluoroalkoxys (e.g., —OCF$_3$), —OCHF$_2$, —OCH$_2$F, —OCCl$_3$, —OCH$_2$CH$_2$Br, —OCH$_2$CH(CH$_2$CH$_2$Br)CH$_3$, and —OCHICH$_3$. In some embodiments, the haloalkoxy group can be further substituted with 1, 2, 3, or 4 substituent groups as described herein for alkyl groups.

The term "haloalkyl," as used herein, represents an alkyl group, as defined herein, substituted by a halogen group (i.e., F, Cl, Br, or I). A haloalkyl may be substituted with one, two, three, or, in the case of alkyl groups of two carbons or more, four halogens. Haloalkyl groups include perfluoroalkyls (e.g., —CF$_3$), —CHF$_2$, —CH$_2$F, —CCl$_3$, —CH$_2$CH$_2$Br, —CH$_2$CH(CH$_2$CH$_2$Br)CH$_3$, and —CHICH$_3$. In some embodiments, the haloalkyl group can be further substituted with 1, 2, 3, or 4 substituent groups as described herein for alkyl groups.

The term "heterocyclyl," as used herein represents a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazinyl, benzimidazolyl, benzothiazolyl, benzoxazolyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2,3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, benzothienyl, and the like, including dihydro and tetrahydro forms thereof, where one or more double bonds are reduced and replaced with hydrogens. Heterocyclyls can be optionally substituted with one, two, three, four, five, or more substituents (e.g., as described herein for alkyl).

The term "hydroxy," as used herein, represents an —OH group.

The term "hydroxyalkyl," as used herein, represents an alkyl group, as defined herein, substituted by one to three hydroxy groups, with the proviso that no more than one hydroxy group may be attached to a single carbon atom of the alkyl group, and is exemplified by hydroxymethyl, dihydroxypropyl, and the like.

The term "isomer," as used herein, means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "thio," as used herein, represents S.

The term "thioalkoxy," as used herein, represents a chemical substituent of formula —SR, where R is an alkyl group, as defined herein. In some embodiments, the alkyl group can be further substituted with 1, 2, 3, or 4 substituent groups as described herein.

The term "thiol" represents an —SH group.

Other features and advantages of the invention will be apparent from the following Detailed Description and the claims.

DETAILED DESCRIPTION

Figure 1:
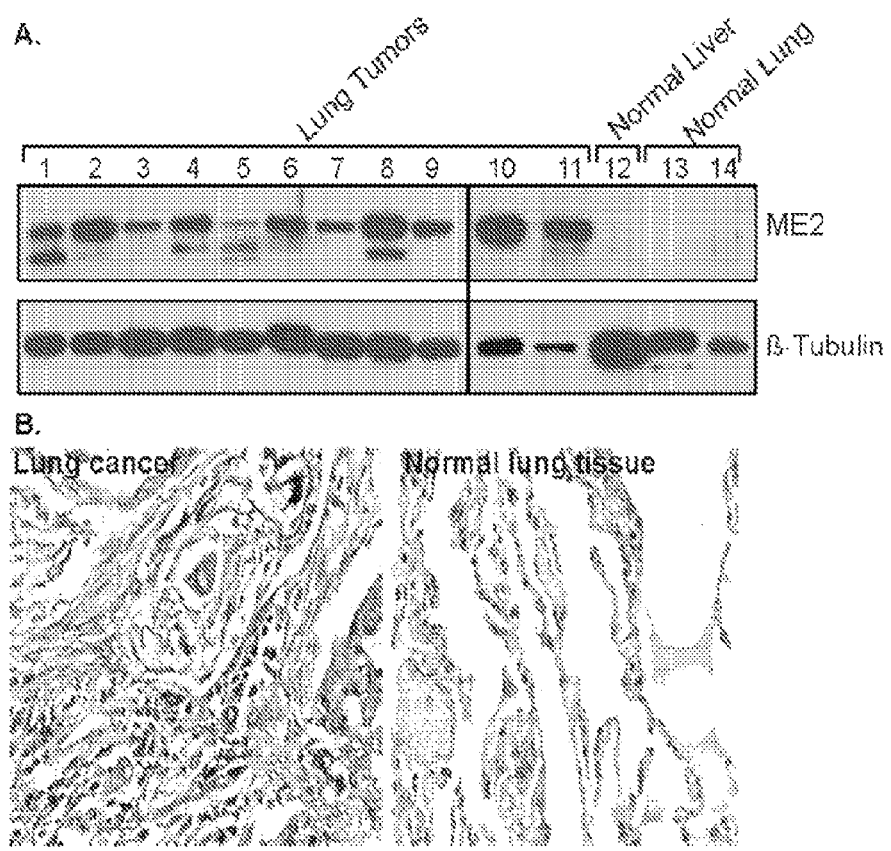
FIG. 1 shows malic enzyme 2 (ME2) expression in lung cancer. A: Human lung cancer tissues lysed in RIPA buffer were purchased from Protein Biotechnologies and analyzed for ME2 and β-tubulin expression by Western blotting. Controls are provided for normal liver tissue and normal lung tissue. B: Representative images are provided from tissue array stained with ME2 antibody.

We have discovered that administration of malate, or a derivative thereof, leads to inhibition of ME2, diminished proliferation of tumor cells, and increased apoptosis. In particular, higher expression of ME2 is associated with various types of cancer cells, such as those for leukemia cells (K562), breast cancer cells (MCF-7), melanoma cells (WM983-B), and lung cancer cells (A549 and H1650). Accordingly, the compositions and methods described herein can be useful for treating a disease, e.g., cancer, associated with decreased levels of malate, or a derivative thereof, and/or increased activity of ME2. Examples of compositions include of malate, or a derivative thereof, in combination with one or more ME2 inhibitors, one or more antineoplastic agents, and/or one or more glycolysis inhibitors. Examples of compositions and diseases are described in detail below.

Malate and Derivatives Thereof.

Malate and derivatives thereof include compounds that have a malate backbone, including malate (i.e., malic acid) itself. Exemplary compounds include malate, dimethyl malate, monomethyl hydrogen malate, diethyl malate, monoethyl hydrogen malate, diisopropyl malate, and others having Formula (I), or a pharmaceutically acceptable salt or isomer thereof.

Commercially available malate and derivatives thereof include, for example, malate, such as D-malate (R-malate), L-malate (S-malate), and DL-malate (from ABI Chem, Germany); dimethyl malate, such as dimethyl L-malate and dimethyl D-malate (Sigma-Aldrich Co., St. Louis, Mo.); diethyl malate, such as diethyl DL-malate (Sigma-Aldrich Co.); and diisopropyl malate, such as diisopropyl S-malate (Sigma-Aldrich Co.).

Malate derivatives can be identified by any useful assay, such as by contacting a cell or malic enzyme 2 in solution with a candidate compound, determining the level of malate, or derivative thereof, in the cell, and comparing the level of malate, or derivative thereof, with a normal reference sample, where the presence of an increased level of malate, or derivative thereof, in the cell or in the solution (e.g., an increased level of malate, or a derivative thereof, of at least 2-fold, e.g., from about 2-fold to about 150-fold, or an increase of at least 5%, e.g., from 5% to 1000%, and useful ranges in between, e.g., as described herein) as compared to the normal reference sample, results in identifying the candidate compound as a malate derivative (e.g., useful for treating a proliferative disorder).

Diseases

The methods and compositions of the invention include administration of one or more of malate, or a derivative thereof, to subject having a disease or at risk of developing a disease (e.g., an increased risk of at least 10%, 20%, 30%, 40%, 50%, 60%, 70%, 80%, 90%, or 100%) associated with a decreased level of malate, or a derivative thereof (e.g., a decreased level of at least 2-fold, or any useful range described herein, as compared to a control or a normal reference sample).

As malate, or a derivative thereof, can be used to decrease expression of ME2, the compositions and methods of the invention could be useful to treat diseases in various types of tissues and/or to target various types of tissues. Increased expression of ME2 protein is observed in different types of tumor tissues, including bladder, breast, esophagus, liver, lung, ovary, prostate, and skin. ME2 is also expressed in other tissues, including the brain (in neurons) and in the heart (in myocytes). Accordingly, malate, or derivatives thereof, can be used to treat diseases (e.g., a proliferative disorder, such as cancer) in any of these tissues.

Any useful methods can be used to determine one or more diseases having a decreased level of malate, or a derivative thereof. For example, levels of malate, or a derivative thereof, can be determined by mass spectrometry (e.g., MS and LC-MS) and/or by an enzymatic assay (e.g., with ME2 or modified versions thereof, such as described herein; with malate dehydrogenase, which oxidizes malate to oxaloacetate; or with a commercially available assay kit). Commercially available assay kits include Malate Assay Kit (ab83391) from Abcam® (Cambridge, Mass., USA).

Proliferative diseases include, e.g., cancer (e.g., benign and malignant, or any described herein), benign prostatic hyperplasia, psoriasis, Reiter's syndrome, pityriasis rubra pilaris, an abnormal keratinization disorder (e.g., actinic keratosis and senile keratosis), scleroderma, a lymphoproliferative disorder (e.g., a disorder in which there is abnormal proliferation of cells of the lymphatic system), chronic rheumatoid arthritis, arteriosclerosis, atherosclerosis, restenosis, and diabetic retinopathy. Proliferative diseases are described in U.S. Pat. Nos. 5,639,600 and 7,087,648, hereby incorporated by reference.

In particular embodiments, the disease is cancer. Exemplary cancers include non-solid cancers and solid cancers, such as leukemia (e.g., chronic myeloid leukemia, acute myeloid leukemia, acute lymphoblastic leukemia, and chronic lymphocytic leukemia), brain cancer (e.g., ependymoma, glioma, medulloblastoma, meningioma, teratoid rhabdoid tumor, and teratoma), bladder cancer (e.g., adenocarcinoma, sarcoma, small cell carcinoma, squamous cell carcinoma, and transitional cell carcinoma), breast cancer (e.g., breast ductal carcinoma), cervical cancer, colorectal cancer, endometrial cancer, esophageal cancer (e.g., adenocarcinoma and squamous cell carcinoma), head and neck cancer, liver cancer (e.g., hepatocellular carcinoma, cholangiocarcinoma, and hemangioendothelioma), lung cancer (e.g., non-small cell lung cancer, small-cell lung cancer, carcinoid, sarcoma, squamous cell cancer, adenocarcinoma (e.g., papillary adenocarcinoma), adenosquamous cell cancer, spindle cell carcinoma, and large cell carcinoma), lymphoma (e.g., malignant lymphoma), ovarian cancer (e.g., ovarian epithelial carcinoma and teratoma), pancreatic cancer, prostate cancer (e.g., adenocarcinoma and prostatic intraepithelial neoplasia), renal cancer, skin cancer (e.g., basal cell carcinoma, squamous cell carcinoma, and malignant melanoma), stomach cancer, testis cancer, thyroid cancer, and urothelial cancer.

The methods and compositions described herein can also be used to treat cancers having one or more particular mutations that confer resistance to first-line antineoplastic agents. Exemplary cancers having mutations include non-small cell lung cancer having a T790M or a L747S mutation in EGFR kinase, a somatic activating mutation in the tyrosine-kinase pocket of EGFR (e.g., a deletion in exon 19 or a substitution in exon 21, e.g., L858R), or a mutation present in tyrosine kinase inhibitor-resistant cell line H1975; and brain cancer, breast cancer, colorectal cancer, lung cancer, and stomach cancer having a E542K, E545K, H1047R, P539R, or H1047L mutation in the PIK3CA gene (encoding a p110α of class IA of PI3K) (e.g., lung cancer having a H1047R mutation in PIK3CA).

Combination Therapy

The methods and compositions include combinations of malate, or a derivative thereof, with a therapeutic agent, such as an ME2 inhibitor, an antineoplastic agent, or a glycolysis inhibitor. Exemplary ME2 inhibitors, antineoplastic agents, and glycolysis inhibitors are described herein.

ME2 Inhibitors

ME2 inhibitors include one or more compounds that directly or indirectly inhibit ME2 gene expression, protein expression, or enzymatic activity. Exemplary ME2 inhibitors include an RNAi agent (e.g., a shRNA for ME2, as described herein), an anti-ME2 antibody, S-oxalylglutathione and derivatives thereof, lanthanides (e.g., lutetium, lanthanum, cerium, erbium, terbium, ytterbium, and holmium, as well as complexes thereof, such as lanthanide-labeled polyaminophosphonates, lanthanide-labeled antibodies, and lanthanide-labeled peptides), steroids (e.g., pregnenolone), and inhibitors of one or more proteins selected from the group of PI3K, RTK (e.g., EGFR, Her2, PDGFR, or IGFR), PDK1, AKT, mTOR (e.g., mTOR1 or mTOR2), and dual inhibitors of any of these proteins. Additional ME2 inhibitors can be identified by any useful method, such as by inhibiting or activating one or more proteins upstream of ME2 in the PI3/AKT pathway that results in ME2 inhibition.

ME2 inhibitors can be identified by any useful assay, such as by contacting a cell or malic enzyme 2 in solution with a candidate compound, determining the level of malic enzyme 2 activity in the cell, and comparing the level of malic enzyme 2 activity with a normal reference sample, where the presence of a decreased level of malic enzyme 2 activity in the cell (e.g., a decreased level of malic enzyme 2 activity of at least 2-fold, e.g., from about 2-fold to about 150-fold, e.g., from 5-fold to 150-fold, from 5-fold to 100-fold, from 10-fold to 150-fold, from 10-fold to 100-fold, from 50-fold to 150-fold, from 50-fold to 100-fold, from 75-fold to 150-fold, or from 75-fold to 100-fold, as compared to a control or a normal reference sample), as compared to the normal reference sample, results in identifying the candidate compound as a malic enzyme 2 inhibitor.

In any of the methods described herein, the level of malic enzyme 2 activity is one or more (e.g., two, three, four, five, six, seven, eight, nine, ten, or more) of levels of ME2, AKT1/2, AKT1, AKT2, ERK1/2, ERK1, GATA-1, PI3K, PDK1, mTOR1/2, mTOR2, EGFR, Her2, PDGFR, IGFR, vimentin, NADH, NADPH, NAD$^+$/NADH ratio, NADP$^+$/NADPH ratio, ROS, ATP, inosine, uridine, or orotate (e.g., as defined herein). In other embodiments, the level of malic enzyme 2 activity is one or more of a cellular parameter (e.g., apoptosis, proliferation, and pyrimidine metabolism).

ME2 inhibitors include one or more RNAi agents that inhibit ME2 gene expression in a cell in vitro or in vivo (e.g., in a subject). The RNAi agents can include different types of double-stranded molecules that include either RNA:RNA or RNA:DNA strands. These agents can be introduced to cells in a variety of structures, including a duplex (e.g., with or without overhangs on the 3'-terminus), a hairpin loop, or an expression vector that express one or more polynucleotides capable of forming a double-stranded polynucleotide alone or in combination with another polynucleotide.

Exemplary RNAi agents include siRNA, shRNA, DsiRNA, and miRNA agents. Generally, these agents are about 10 to about 40 nucleotides in length, and preferred lengths for particular RNAi agents include siRNA that are double-stranded RNA molecules of 16 to 30 nucleotides in length (e.g., 18 to 25 nucleotides, e.g., 21 nucleotides); shRNA that are single-stranded RNA molecules in which a hairpin loop structure is present and a stem length is between 19 to 29 nucleotides in length (e.g., 19 to 21 nucleotides or 25 to 29 nucleotides) or a loop size is between 4 to 23 nucleotides in length; DsiRNA that are double-stranded RNA agents of 25 to 35 nucleotides in length; and miRNA that are single-stranded RNA molecules of 17 to 25 nucleotides (e.g., 21 to 23 nucleotides) in length. The RNAi agent can have any useful nucleic acid sequence, including a nucleic acid sequence having one or more DNA molecules, RNA molecules, or modified forms (e.g., a modified backbone composition or 2'-deoxy- or 2'-O-methyl modifications) or combinations thereof.

ME2 inhibitors include one or more RNAi agents. Exemplary RNAi agents include shRNA agents, such as CGGCATATTAGTGACAGTGTT (shME2-1 sense, SEQ ID NO:7), CCCAGTATGGACACATCTTTA (shME2-2 sense, SEQ ID NO:8), GCACGGCTGAAGA AGCATATA (shME2-3 sense, SEQ ID NO:9), TTAGATCAATTGTG-GATAACTGGCC AGAA (sense, SEQ ID NO:10), GAAGACTTTGGAAATCATAATGCATTCAG (sense, SEQ ID NO:11), GCGAGTCTTTACACCAGGT-CAAGGAAACA (sense, SEQ ID NO:12), CCAGG TGTG-GCTTTAGCTGTTATTCTCTG (sense, SEQ ID NO:13). TGCTGTTGACAGTGAGCGCGCCACTTATGCTGAAC-CCAAGTAGTGAAGCCACAGAT GTACTTGGGTTCA-GCATAAGTGGCTTGCCTACTGCCTCGGA (V2HS_151676, SEQ ID NO:14), TGCTGTTGACAGT-GAGCGACAAGATGACATTGAGAGTTTATAGT GAAGCCACAGATGTATAAACTCTCAATGTCATCTT-GCTGCCTACTGCCTCGGA (V2HS_151677, SEQ ID NO:15), TGCTGTTGACAGTGAGCGCGGT-CAAGGAAACAA TGTTTATTAGTGAAGCCACAGAT-GTAATAAACATTGTTTCCTTGACCTTGCCTACTGC CTCGGA (V2HS_151680, SEQ ID NO:16), TGCTGTT-GACAGTGAGCGATAGGAA AACTTTGTTTG-TATATAGTGAAGCCACAGATGTATATA-CAAACAAAGTTTTCCTACT GCCTACTGCCTCGGA (V3LHS_392891, SEQ ID NO:17), TGCTGTTGACAGT-GAG CGACAGAAACGAGATCGCACACAATAGT-GAAGCCACAGATGTATTGTGTGCGATCT CGTTTCTGGTGCCTACTGCCTCGGA (V3LHS_392894, SEQ ID NO:18), TGCTGTTGACAGTGAGCGACT-GAAGAAGCATATACACTTATAGTGAAGCCACAGAT GTATAAGTGTATATGCTTCTTCAGCTGCCTACTGC-CTCGGA (V3LHS_392895, SEQ ID NO:19), CCGGCG-CATATTAGTGACAGTGTTCTCGAGAACACTGT-CACT AATATGCCGTTTTTG (TRCN0000064738, SEQ ID NO:20), CCGGGAAAGCTATTACTGACAGATACTC-GAGTATCTGTCAGTAATAGCTTTCTTTTT G (TRCN0000064740, SEQ ID NO:21), CCGGCCCAG-TATGGACACATC TTTACTCGAGTAAAGATGTGTC-CATACTGGGTTTTTG (TRCN0000064741, SEQ ID NO:22), CCGGGCACGGCTGAAGAAGCATATACT CGAGTATATGCTTCTTCA GCCGTGCTTTTTG (TRCN0000064742, SEQ ID NO:23), CCGGTACTTTG-GCATGTC GACATTTCTCGAGAAATGTCGACATGC-CAAAGTATTTTTG (TRCN0000294005, SEQ ID NO:24), and CCGGAGTTCTTACAGAGCTACTAAACTC-GAGTTTAGTAGCT CTGTAAGAACTTTTTTG (TRCN0000294007, SEQ ID NO:25); and siRNA agents, such as CCACTTATGCTGAACCCAA (mature sense for V2HS_151676, SEQ ID NO:26) and 3'-TTGGGTTCAG-CATAAGTGG-5' (mature antisense for V2HS_151676, SEQ ID NO:27), GTCAAGGAAACAATGTTTA (mature sense for V2HS_151680, SEQ ID NO:28) and 3'-TAAACATTGTTTCCTTGAC-5' (mature antisense for V2HS_151680, SEQ ID NO:29), AAGATGACATT-GAGAGTTT (mature sense for V2HS_151677, SEQ ID NO:30) and 3'-AAACTCTCAATGTCATCTT-5' (mature antisense for V2HS_151677, SEQ ID NO:31), TGAAGAAGCATATACACTT (mature sense for V3LHS_392895, SEQ ID NO:32) and 3'-AAGTGTATAT-GCTTCTTCA-5' (mature antisense for V3LHS_392895, SEQ ID NO:33), AGGAAAACTTTGTTTGTAT (mature sense for V3LHS_392891, SEQ ID NO:34) and 3'-ATA-CAAACAAAGTTTTCCT-5' (mature antisense for V3LHS_392891, SEQ ID NO:35), AGAAACGAGATCG-CACACA (mature sense for V3LHS_392894, SEQ ID NO:36) and 3'-TGTGTGCGATCTCGTTTCT-5' (mature antisense for V3LHS_392894, SEQ ID NO:37), CGGCAT-ATTAGTGACAGTGTT (sense for TRCN0000064738, SEQ ID NO:7) and 3'-AACACTGTCACTAATATGCCG-5' (antisense for TRCN0000064738, SEQ ID NO:38), GAAAGCTATTACTGACAGATA (mature sense for TRCN0000064740, SEQ ID NO:39) and 3'-TATCTGTCA-GTAATAGCT TTC-5' (mature antisense for TRCN0000064740, SEQ ID NO:40), CCCAGTATGGA CACATCTTTA (mature sense for TRCN0000064741, SEQ ID NO:8) and 3'-TAAAG ATGTGTCCATACTGGG-5' (mature antisense for TRCN0000064741, SEQ ID NO:41), and GCACGGCTGAAGAAGCATATA (mature sense for TRCN0000064742, SEQ ID NO:9) and 3'-TATATGCTTCT-TCAGCCGTGC-5' (mature antisense for TRCN0000064742, SEQ ID NO:42), where sequences are provided in the 5' to 3' direction, unless otherwise specified. RNAi agents also include commercially available agents, such as those available from OriGene Technologies (Rockville, Md.) and Santa Cruz Biotechnologies, Inc. (Santa Cruz, Calif.).

ME2 inhibitors also include one or more anti-ME2 antibodies. Exemplary antibodies include HPA008247 (Ab2, anti-ME antibody produced in rabbit, where the immunogen is the NAD-dependent malic enzyme, mitochondrial precursor recombinant protein epitope signature tag DGRVFT-PGQGNNVYIFPGVALAVILCNTRHISDSVFLEAAKA-LTSQLTD EELAQGRLYPPLANIQEVSINIAIKVTEYLYANKMA-FRYPEPEDKAKYVKERTWRSEYD SLLPDVYEWPE-SASSPPV (SEQ ID NO:43)) and HPA008880 (anti-ME antibody produced in rabbit, where the immunogen is the NAD-dependent malic enzyme, mitochondrial precursor recombinant protein epitope signature tag KVISKPISEH-KILFLG AGEAALGIANLIVMSMVENGLSEQEAQKKI-WMFDKYGLLVKGRK AKIDSYQEPFTHSA PESIP-DTFEDAVNILKPSTIIGVAGAGRLFTPDVIRAMASINE RPVIFALSNPTA (SEQ ID NO:44)). RNAi agents also include commercially available antibodies, such as those available from Abcam (Cambridge, Mass.), Atlas Antibodies AB (Stockholm, Sweden), Novus Biologicals (Littleton, Colo.), LifeSpan Biosciences (Seattle, Wash.), and Santa Cruz Biotechnology (Santa Cruz, Calif.).

ME2 inhibitors include agents that inhibiting one or more proteins upstream of ME2 in the PI3/AKT pathway, such as a PI3K inhibitor, an RTK inhibitor (e.g., an EGFR inhibitor, an Her2 inhibitor, a PDGFR inhibitor, or an IGFR inhibitor), a PDK1 inhibitor, an AKT inhibitor, an mTOR inhibitor (e.g., an mTOR1 inhibitor or an mTOR2 inhibitor), and dual inhibitors of any of these proteins (e.g., a dual PI3K/mTOR inhibitor or a dual AKT/PDK1 inhibitor). Exemplary ME2 inhibitors further include PI3K inhibitors, such as wortmannin, demethoxyviridin, LY294002 (2-morpholin-4-yl-8-phenylchromen-4-one), quercetin, myricetin, staurosporine, GDC-0941 (4-[2-(1H-indazol-4-yl)-6-[(4-methylsulfonylpiperazin-1-yl)methyl]thieno[3,2-d]pyrimidin-4-yl]morpholine), NVP-BEZ235 (2-methyl-2-[4-(3-methyl-2-oxo-8-quinolin-3-ylimidazo[4,5-c]quinolin-1-yl)phenyl] propanenitrile), ZSTK474 (4-[4-[2-(difluoromethyl) benzimidazol-1-yl]-6-morpholin-4-yl-1,3,5-triazin-2-yl] morpholine), PX-866 ([(3 aR,6E,9S,9aR,10R,11aS)-6-[[bis (prop-2-enyl)amino]methylidene]-5-hydroxy-9-(methoxymethyl)-9a,11a-dimethyl-1,4,7-trioxo-2,3,3a,9,10, 11-hexahydroindeno[4,5-h]isochromen-10-yl]acetate), and XL-147 (N-[3-(2,1,3-benzothiadiazol-4-ylamino)quinoxalin-2-yl]-4-methylbenzenesulfonamide); RTK inhibitors, such as erlotinib, gefitinib, vandetanib, afatinib, axitinib, cediranib, cetuximab, lapatinib, lestaurtinib, neratinib, panitumumab, pazopanib, regorafenib, semaxanib, sorafenib, sunitinib, toceranib, and trastuzumab; non-specific PDK1 inhibitors, such as OSU-03012 (2-amino-N-[4-[5-phenanthren-2-yl-3-(trifluoromethyl)pyrazol-1-yl]phenyl]acetamide) and celecoxib; AKT inhibitors, such as A-443654 ((2S)-1-(1H-indol-3-yl)-3-[5-(3-methyl-2H-indazol-5-yl) pyridin-3-yl]oxypropan-2-amine), GSK690693 (4-[2-(4-amino-1,2,5-oxadiazol-3-yl)-1-ethyl-7-[[(3S)-piperidin-3-yl]methoxy]imidazo[4,5-c]pyridin-4-yl]-2-methylbut-3-yn-2-ol), VQD-002 (triciribine), and perifosine; dual AKT/PDK1 inhibitors, such as 6H-indeno[1,2-e]tetrazolo[1,5-b] [1,2,4]triazin-6-one, 10H-indeno[2,1-e]tetrazolo[1,5-b][1,2, 4]triazin-10-one, and PHT-427 (4-dodecyl-N-(1,3,4-thiadiazol-2-yl)benzenesulfonamide); mTOR inhibitors, such as rapamycin (sirolimus) and modified rapamycins (rapalogs), such as CCI-779 (temsirolimus), and RAD001 (everolimus)); and dual PI3K/mTOR inhibitors, such as NVP-BEZ235 (2-methyl-2-[4-(3-methyl-2-oxo-8-quinolin-3-ylimidazo[4,5-c]quinolin-1-yl)phenyl]propanenitrile) and PI-103 (3-[4-(4-morpholinyl)pyrido[3',':4,5]furo[3,2-d]pyrimidin-2-yl]-phenol).

Antineoplastic Agents

Exemplary antineoplastic agents include chemotherapeutic agents (e.g., arsenic trioxide, cisplatin, carboplatin, chlorambucil, melphalan, nedaplatin, oxaliplatin, triplatin tetranitrate, satraplatin, imatinib, nilotinib, dasatinib, and radicicol), immunomodulatory agents (e.g., methotrexate, leflunomide, cyclophosphamide, cyclosporine A, minocycline, azathioprine, antibiotics (e.g., tacrolimus), methylprednisolone, corticosteroids, steroids, mycophenolate mofetil, rapamycin, mizoribine, deoxyspergualin, brequinar, T cell receptor modulators, and cytokine receptor modulators), antiangiogenic agents (e.g., alitretinoin, beloranib, bevacizumab, cetuximab, endostatin (e.g., recombinant forms thereof), erlotinib, etrathiomolybdate, everolimus, imiquimod, interferon alfa (e.g., recombinant forms thereof), itraconazole, lenalidomide, pazopanib, sorafenib, sunitinib, suramin, temsirolimus, thalidomide, tivozanib, vandetanib, and vatalanib), mitotic inhibitors (e.g., paclitaxel, vinorelbine, docetaxel, abazitaxel, ixabepilone, larotaxel, ortataxel, tesetaxel, vinblastine, vincristine, vinflunine, and vindesine), nucleoside analogs (e.g., gemcitabine, azacitidine, capecitabine, carmofur, cladribine, clofarabine, cytarabine, decitabine, floxuridine, fludarabine, fluorouracil, mercaptopurine, pentostatin, tegafur, and thioguanine), DNA intercalating agents (e.g., doxorubicin, actinomycin, bleomycin, mitomycin, and plicamycin), topoisomerase inhibitors (e.g., irinotecan, aclarubicin, amrubicin, belotecan, camptothecin, daunorubicin, epirubicin, etoposide, idarubicin, mitoxantrone, pirarubicin, pixantrone, rubitecan, teniposide, topotecan, valrubicin, and zorubicin), antibodies (e.g., monoclonal antibodies, such as alemtuzumab, bevacizumab, brentuximab vedotin, catumaxomab, cetuximab, denosumab, edrecolomab, ertumaxomab, gemtuzumab ozogamicin, ibritumomab, ibritumomab tiuxetan, ipilimumab, ofatumumab, panitumumab, rituximab, tositumomab, trastuzumab, and anti-IGF1R antibodies (e.g., MK-0646, BIIIB011, and AVE1642), as well as radiolabeled forms thereof (e.g., with $^{131}$I or $^{90}$Y); human monoclonal antibodies (e.g., adecatumumab, belimumab, cixutumumab, conatumumab, daratumumab, drozitumab, figitumumab, flanvotumab, ganitumab, glembatumumab vedotin, intetumumab, iratumumab, lexatumumab, lucatumumab, mapatumumab, narnatumab, necitumumab, ofatumumab, olaratumab, panitumumab, pritumumab, radretumab, rilotumumab, robatumumab, teprotumumab, votumumab, and zalutumumab); humanized monoclonal antibodies (e.g., afutuzumab, alemtuzumab, bevacizumab, bivatuzumab mertansine, cantuzumab (e.g., cantuzumab mertansine or ravtansine), citatuzumab bogatox, clivatuzumab tetraxetan, dacetuzumab, dalotuzumab, elotuzumab, etaracizumab, farletuzumab, ficlatuzumab, gemtuzumab ozogamicin, inotuzumab ozogamicin, labetuzumab, lintuzumab, lorvotuzumab mertansine, matuzumab, milatuzumab, nimotuzumab, onartuzumab, oportuzumab monatox, pertuzumab, sibrotuzumab, tacatuzumab tetraxetan, tigatuzumab, trastuzumab, tucotuzumab celmoleukin, and veltuzumab); chimeric monoclonal antibodies (e.g., amatuximab, bavituximab, brentuximab vedotin, cetuximab, ecromeximab, ensituximab, girentuximab, indatuximab ravtansine, rituximab, siltuximab, and ublituximab); and mouse monoclonal antibodies (e.g., abagovomab, altumomab pentetate, anatumomab mafenatox, arcitumomab, bectumomab, blinatumomab, capromab pendetide, CC49, detumomab, edrecolomab, ibritumomab tiuxetan, igovomab, minretumomab, mitumomab, moxetumomab pasudotox, naptumomab estafenatox, nofetumomab merpentan, oregovomab, pemtumomab, pintumomab, racotumomab, satumomab pendetide, taplitumomab paptox, tenatumomab, tositumomab, and 3F8), cytokines (e.g., recombinant interferon alpha (e.g., interferon alfa-2a, interferon alfa-2b, interferon alfa-n1, interferon alpha-n3, interferon alfacon-1, albinterferon, and pegylated forms thereof), interferon beta (e.g., interferon beta-1a and interferon beta-1b), interferon gamma, interleukin 2 (Aldesleukin), interleukin 11 (Oprelvekin), granulocyte colony-stimulating factor (G-CSF, e.g., recombinant G-CSF (Filgrastim and Lenograstim) and pegylated forms thereof (e.g., Pegfilgrastim)), granulocyte macrophage colony-stimulating factor (GM-CSF, e.g., recombinant GM-CSF (Molgramostim and Sargramostim)), and methionyl human stem cell factor (SCF, e.g., recombinant SCF (Ancestim)), folate antimetabolites (e.g., pemetrexed, aminopterin, methotrexate, pralatrexate, and raltitrexed), and other targeting agents (e.g., agents that target particular enzymes or proteins involved in cancer or agents that target particular organs or types of cancers), and combinations thereof.

Glycolysis Inhibitors

Glycolysis inhibitors can be useful in treating proliferative disorders. Accordingly, the present invention encompasses methods and compositions that include malate, or a derivative thereof, with one or more glycolysis inhibitors. Exemplary glycolysis inhibitors include hexokinase inhibitors, including hexokinase 2 (HK2) inhibitors (e.g., 2-deoxyglucose, halogenated derivatives of 2-deoxyglucose (e.g., 2-fluorodeoxy-glucose), 5-thioglucose, 3-bromopyruvate (3-BrPA), 3-bromo-2-oxopropionate-1-propylester (3-BrOP), lonidamine, imatinib, meclofenoxate, O,O-diethyl O-3,5,6-trichloro-2-pyridyl phosphate, 7,8-dihydro-7,8-dihydroxybenzo(a)pyrene 9,10-oxide, antisense RNA, N-terminal oligopeptide of hexokinase II (e.g., MIASHLLAYFFTELN-amide (hexokinase II VDAC binding domain peptide; HXK2VBD (SEQ ID NO:1)) and RQIKIWFQNRRMKWKKMIASHLLAYFFTELN-amide (SEQ ID NO:2)), antifungal derivatives (e.g., clotrimazole and bifonazole), and D-mannoheptulose); lactate dehydrogenase inhibitors, including lactate dehydrogenase A (LDH-A) inhibitors and lactate dehydrogenase 5 (LDH-5) inhibitors (e.g., oxamate, gossypol, 3-hydroxyisoxazole-4-carboxylic acid (HICA), 4-hydroxy-1,2,5-thiadiazole-3-carboxylic acid (HTCA), 3-dihydroxy-6-methyl-7-(phenylmethyl)-4-propylnaphthalene-1-carboxylic acid (FX11), 7,8-dihydro-7,8-dihydroxybenzo(a)pyrene 9,10-oxide, cyclosporine, lindane, antisense RNA (e.g., shRNA, nt 204-232 (L1, gattaca gttgttgggg ttggtgctgt tg (SEQ ID NO:3)), nt 737-765 (L2, tgtg gagtggtgtg aatgttgccg gcgtc (SEQ ID NO:4)), and nt 1161-1188 (L3, tcactgtcca ggctgcagca gggcttct (SEQ ID NO:5)) of NCBI Reference Sequence: NM_010699)), 1-hydroxy-5-phenyl-1H-indole-2-carboxylic acid, 1-hydroxy-6-phenyl-1H-indole-2-carboxylic acid, and 1-hydroxy-6-phenyl-4-trifluoromethyl-1H-indole-2-carboxylic acid); phosphofructokinase 2 or phosphofructo-2-kinase/fructose-2,6-bisphosphatase (PFK2/PFKFB3) inhibitors (e.g., 3-(3-pyridinyl)-1-(4-pyridinyl)-2-propen-1-one); pyruvatekinase M2 (PKM2) inhibitors (e.g., 4R,7S,10R,13S,16R)-7-(4-aminobutyl)-N-[(3R)-1-amino-3-hydroxy-1-oxobutan-2-yl]-16-[[(2R)-2-amino-3-phenylpropanoyl]amino]-13-[(4-hydroxyphenyl)methyl]-10-(1H-indol-3-ylmethyl)-6,9,12,15-tetraoxo-1,2-dithia-5,8,11,14-tetrazacycloheptadecane-4-carboxamide (TLN-232/CAP-232), shikonin, and alkannin); transketolase inhibitors, including transketolase-like enzyme 1 (TKTL1) inhibitors (e.g., oxythiamine and furazolidone); pyruvate dehydrogenase (PDH) inhibitors (e.g., oxythiamine); pyruvate dehydrogenase kinase (PDK) inhibitors (e.g., dichloroacetate); glucose-6-phosphate dehydrogenase (G6PG) inhibitors (e.g., 6-aminonicotinamide, imatinib, 2,2'-azobis(2-amidinopropane), 2,5-dihydroxybenzoic acid, aluminum phosphide, arjunolic acid, benzo(a)pyrene, benzoyl peroxide, calphostin C, cycloartenol, dactinomycin, dexamethasone, diethylnitrosamine, endosulfan, fenvalerate, ferric nitrilotriacetate, ferrous sulfate, glyoxylic acid, furantoin, phenobarbitol, quercetin, isotretinoin, and streptozocin); GLUT inhibitors (e.g., fluorodeoxyglucose, including radiolabelled forms ([18F]-fluorodeoxyglucose), 2-deoxyglucose, phloretin, and silybin/silibinin); proton transport inhibitors, such as carbonic anhydrase-9 (CA9) inhibitors, membrane-bound V-ATPase inhibitors, and sodium-proton exchanger 1 (NHE1) inhibitors (e.g., paclitaxel, acetazolamide, cariporide, indisulam, girentuximab, esomeprazole, amiloride and derivatives thereof (5-(N-ethyl-Nisopropyl)amiloride (EIPA)); monocarboxylate transporter (MCT) inhibitors, such as MCT1, MCT2, MCT3, or MCT4 inhibitors (e.g., α-cyano-4-hydroxycinnamate (CHC), AZD3965, or AR-C117977); hypoxia-inducible factor 1 alpha (HIF-1 alpha) inhibitors (e.g., BAY87-2243, acriflavine, PX-478, tirapazamine, and an antisense oligonucleotide targeting HIF-1α (EZN-2968, 5'-TG-GcaagcatccTGTa-3', where upper case indicates LNA residues and lower case indicates DNA residues (SEQ ID NO:45))); a c-Myc inhibitor (e.g., (5E)-5-[(4-ethylphenyl)methylidene]-2-sulfanylidene-1,3-thiazolidin-4-one (10058-F4) and quarfloxin/CX-3453); AMPK inhibitors (e.g., metformin); glutamine inhibitors (e.g., phenylacetate); asparagine inhibitors (e.g., asparaginase and pegasparaginase); arginine inhibitors (e.g., arginine deaminase); fatty acid synthase (FASN) inhibitors (e.g., orlistat, GSK837149A, and C75); and ATP-citrate lyase (ACLY) inhibitors (e.g., 2-[(3S,5R)-5-[6-(2,4-dichlorophenyl)hexyl]-3-hydroxy-2-oxooxolan-3-yl]acetic acid (SB-204990), quercetin, and rutin).

Administration and Dosage

The present invention also relates to pharmaceutical compositions that contain one or more of malate, or a derivative thereof, or a combination of malate, or a derivative thereof, and a therapeutic agent (e.g., a ME2 inhibitor, an antineoplastic agent, and/or a glycolysis inhibitor). The composition can be formulated for use in a variety of drug delivery systems. One or more physiologically acceptable excipients or carriers can also be included in the composition for proper formulation. Suitable formulations for use in the present invention are found in *Remington's Pharmaceutical Sciences*, Mack Publishing Company, Philadelphia, Pa., 17th ed., 1985. For a brief review of methods for drug delivery, see, e.g., Langer, *Science* 249:1527-1533, 1990.

The pharmaceutical compositions are intended for parenteral, intranasal, topical, oral, or local administration, such as by a transdermal means, for prophylactic and/or therapeutic treatment. The pharmaceutical compositions can be administered parenterally (e.g., by intravenous, intramuscular, or subcutaneous injection), or by oral ingestion, or by topical application or intraarticular injection at areas affected by the proliferative disorder. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration. Sustained release administration is also specifically included in the invention, by such means as depot injections or erodible implants or components. Thus, the invention provides compositions for parenteral administration that comprise the above mention agents dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like. The invention also provides compositions for oral delivery, which may contain inert ingredients such as binders or fillers for the formulation of a tablet, a capsule, and the like. Furthermore, this invention provides compositions for local administration, which may contain inert ingredients such as solvents or emulsifiers for the formulation of a cream, an ointment, and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above mentioned agent or agents, such as in a sealed package of tablets or capsules. The composition in solid form can also be packaged in a container for a flexible quantity, such as in a squeezable tube designed for a topically applicable cream or ointment.

The compositions containing an effective amount can be administered for prophylactic or therapeutic treatments. In prophylactic applications, compositions can be administered to a patient with a clinically determined predisposition or increased susceptibility to development of a tumor or a proliferative disorder (e.g., cancer). Compositions of the invention can be administered to the patient (e.g., a human) in an amount sufficient to delay, reduce, or preferably prevent the onset of clinical disease or tumorigenesis. In therapeutic applications, compositions are administered to a patient (e.g., a human) already suffering from a cancer in an amount sufficient to cure or at least partially arrest the symptoms of the condition and its complications. An amount adequate to accomplish this purpose is defined as a "therapeutically effective dose," an amount of a compound sufficient to substantially improve some symptom associated with a disease or a medical condition. For example, in the treatment of cancer, an agent or compound which decreases, prevents, delays, suppresses, or arrests any symptom of the disease or condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual.

Amounts effective for this use may depend on the severity of the disease or condition and the weight and general state of the patient, but generally range from about 0.5 mg to about 3000 mg of the agent or agents per dose per patient. Suitable regimes for initial administration and booster administrations are typified by an initial administration followed by repeated doses at one or more hourly, daily, weekly, or monthly intervals by a subsequent administration. The total effective amount of an agent present in the compositions of the invention can be administered to a mammal as a single dose, either as a bolus or by infusion over a relatively short period of time, or can be administered using a fractionated treatment protocol, in which multiple doses are administered over a more prolonged period of time (e.g., a dose every 4-6, 8-12, 14-16, or 18-24 hours, or every 2-4 days, 1-2 weeks, once a month). Alternatively, continuous intravenous infusion sufficient to maintain therapeutically effective concentrations in the blood are contemplated.

The therapeutically effective amount of one or more agents present within the compositions of the invention and used in the methods of this invention applied to mammals (e.g., humans) can be determined by the ordinarily-skilled artisan with consideration of individual differences in age, weight, and the condition of the mammal. The agents of the invention are administered to a subject (e.g. a mammal, such as a human) in an effective amount, which is an amount that produces a desirable result in a treated subject (e.g. the slowing or remission of a proliferative disorder, such as cancer). Such therapeutically effective amounts can be determined empirically by those of skill in the art.

The patient may also receive an agent in the range of about 0.1 to 3,000 mg per dose one or more times per week (e.g., 2, 3, 4, 5, 6, or 7 or more times per week), 0.1 to 2,500 (e.g., 2,000, 1,500, 1,000, 500, 100, 10, 1, 0.5, or 0.1) mg dose per week. A patient may also receive an agent of the composition in the range of 0.1 to 3,000 mg per dose once every two or three weeks.

Single or multiple administrations of the compositions of the invention comprising an effective amount can be carried out with dose levels and pattern being selected by the treating physician. The dose and administration schedule can be determined and adjusted based on the severity of the disease or condition in the patient, which may be monitored throughout the course of treatment according to the methods commonly practiced by clinicians or those described herein.

The compounds and formulations of the present invention may be used in combination with either conventional methods of treatment or therapy or may be used separately from conventional methods of treatment or therapy. When the compounds and formulations of this invention are administered in combination therapies with other agents, they may be administered sequentially or concurrently to an individual. Alternatively, pharmaceutical compositions according to the present invention include a combination of a compound or formulation of the present invention in association with a pharmaceutically acceptable excipient, as described herein, and another therapeutic or prophylactic agent known in the art.

The formulated agents can be packaged together as a kit. Non-limiting examples include kits that contain, e.g., two pills, a pill and a powder, a suppository and a liquid in a vial, two topical creams, etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

Diagnostic Methods and Screening Assays

Levels of malate, or a derivative thereof, can also be used for the diagnosis of a disease, such as proliferative disorder (e.g., cancer, such as leukemia or non-small cell lung cancer), or a risk of developing a disease. The level of malate, or a derivative thereof, can also be used to monitor the therapeutic efficacy of one or more compounds, including compounds and compositions of the invention, used to treat a disease, such as a proliferative disorder.

Standard methods may be used to measure analyte levels or cellular parameters in any bodily fluid, including, but not limited to, urine, blood, serum, plasma, saliva, or cerebrospinal fluid. Such methods include use of mass spectrometry, UV absorption spectroscopy, fluorescence spectroscopy, and quantitative enzyme kinetics techniques.

Diagnostic methods can include measurement of absolute levels of malate, or a derivative thereof. In any of the diagnostic methods, the level of malate, or a derivative thereof, can be measured at least two different times from the same subject and an alteration in the levels (e.g., by 10%, 20%, 30%, 40%, 50%, 60%, 70%, 80%, 90%, or more) over time is used as an indicator of a disease associated with decreased levels of malate, or a derivative thereof, e.g., a proliferative disorder, or the propensity to develop the same. It will be understood by the skilled artisan that for diagnostic methods that include comparing of the level of malate, or a derivative thereof, to a reference level, particularly a prior sample taken from the same subject, a change over time with respect to the baseline level can be used as a diagnostic indicator of a proliferative disorder, or a predisposition to develop the same. The diagnostic methods described herein can be used individually or in combination with any other diagnostic method described herein for a more accurate diagnosis of the presence of, severity of, or predisposition to a disease associated with decreased levels of malate, or a derivative thereof, e.g., a proliferative disorder, or a predisposition to the same.

As discussed above, we have discovered that a decreased level of malate, or a derivative thereof, is correlated with cancer. Based on this discovery, additional compounds can be identified that increase levels of malate, or a derivative thereof, for use in treating a proliferative disorder, such as cancer. High-throughput low-cost screening of candidate compounds can be used to identify those that increase (e.g., by at least 10%, 20%, 30%, 40%, 50%, 60%, 70%, 80%, 90%, 95%, or more) levels of malate, or a derivative thereof.

In general, candidate compounds are identified from large libraries of both natural product or synthetic (or semi-synthetic) extracts, chemical libraries, or from polypeptide or nucleic acid libraries, according to methods known in the art. Those skilled in the field of drug discovery and development will understand that the precise source of test extracts or compounds is not critical to the screening procedure(s) of the invention.

EXAMPLES

Materials and Methods

Materials

Dichlorodihydrofluorescein diacetate (CM-$H_2$DCF-DA), MitoSOX™, and nonyl acridine orange (NAO) were purchased from Invitrogen/Molecular Probes (Carlsbad, Calif.). The malate assay kit was obtained from ABCAM (Cambridge, Mass.), and cell migration kits were obtained from Millipore (Merck KGaA, Darmstadt, Germany). Lipofectamine 2000 and tissue culture reagents were purchased from Invitrogen. The pLKO constructs containing short hairpins RNAi (shRNA) targeted to ME2 and ATP citrate lyase (ACL), and its control vector were purchased from OPEN Biosystems. All restriction enzymes were obtained from New England Biolabs. The QIAprep kit was from QIAGEN. Fetal bovine serum (FBS) was obtained from GIBCO. Puromycin, anti-ME2 polyclonal antibody and anti-β-tubulin monoclonal antibody were purchased from Sigma. The anti-vimentin monoclonal antibody was from Santa Cruz Biotechnology. The anti-GATA-1, phospho-ERK1/2, phospho-AKT308, phospho-AKT473 and AKT1/2 polyclonal antibodies were purchased from Cell Signaling Technology. The ERK1/2 monoclonal antibody was from Zymed. The CD235a-FITC and CD10-FITC monoclonal antibodies were obtained from DAKO. Secondary antibodies for enhanced chemiluminescence (ECL) detection were from Amersham Biosciences. All other reagents were of standard analytical grade.

Cell Culture:

The human lung cancer cell line A549 was obtained from American Type Culture Collection and grown in Hams/F12 Medium. All media were supplemented with 10% (v/v) fetal calf serum, 100 units penicillin and 100 μg/ml streptomycin, and grown at 37° C. and 5% $CO_2$. Cells infected with shRNA virus were selected with 1.0 μg/ml puromycin and stable knock-down of ME2 were used for analysis.

Tissue Array:

The tissue micro arrays used for this study were the human multiple organ cancer tissue micro array, BCN961, from US Biomax, Inc. (Rockville, Md.). BCN961 contains 16 types of common organ cancer tissues with matched or unmatched cancer adjacent normal tissue. They are bladder, brain, breast, colon, esophagus, kidney, liver, lung, lymph node, ovary, pancreas, prostate, rectum, skin, stomach and uterine cervix cancer. The array format is 3 cases per type in single core per case. The tissue samples were formalin fixed, paraffin embedded. Array sections were mounted on the positive charged super plus glass slide. The tissue micro array sections were cut at 5 micron in thickness. Individual cores were 1.0 mm in diameter, spaced 0.25 mm. Rabbit anti-ME2 primary antibody was used for ME2 staining. Manual scoring of intensity, negative (0), weak (1+), moderate (2+), or strong (3+), location and cell types of staining were completed by an independent pathologist from US Biomax, Inc. The scores were then converted to numbers in a 0 to 3 scale. The total positive cell numbers and intensity of anti-ME2 staining were computed and measured by ImageScope from Aperio Scanning System.

Generation of ME2 Deficiency Cell Lines:

A549 cells were transduced separately with empty shRNA vector control and three different ME2 shRNA lentiviral particles, as previously described in Root et al., *Nat. Methods* 3: 715-719 (2006). The three ME2 shRNA sequence (sense) used in this study are: shME2-1,5'-CG-GCATATTAGTGACAGTGTT-3' (SEQ ID NO:7); shME2-2,5'-CCCAGTATGGACACATCTTT A-3' (SEQ ID NO:8); and shME2-3,5'-GCACGGCTGAAGAA GCATAT A-3' (SEQ ID NO:9). The shACL sequence is: 5'-GCCTCT-TCAATTTCTACGAGGACTT-3' (SEQ ID NO:46). To produce recombinant lentiviral particles, subconfluent 293FT cells were cotransfected with 3 µg of a shRNA plasmid, and 9 µg virapower packaging mix (Invitrogen) using Lipofectamine 2000 (Invitrogen). After 16 hours, culture medium was switched to regular growth medium and cells were allowed to incubate for additional 48 hours. Conditioned cell culture media containing recombinant lentiviral particles were harvested and frozen. A549 cells were transduced with above cell culture supernatant containing lentiviral particles for 24 hours. These cells were then selected in puromycin (Sigma Aldrich) to generate stable cell lines encoding empty vector shRNA or ME2 shRNA. Hereafter, we named those pools pLKO, shME2-1, shME2-2, and shME2-3, respectively. In order to generate single ME2 knockdown clone, cells from the stable knockdown pools were seeded in a 10 cm plate with 1:500 dilution, and individual clones were selected by cloning disc. The single clone corresponding to its parental pools were named pLKO-s, shME2-1s, shME2-2s, and shME2-3 s, respectively.

Western Blotting:

A549 cells with and without ME2 knockdown were lysed with RIPA buffer (50 mM Tris-HCl, pH 7.4, 150 mM NaCl, 1% NP-40, 0.1% SDS and 0.5% sodium deoxycholate), and equal amount of proteins were resolved by 4%-12% Bis-Tris gels (Invitrogen), as previously described in Ren et al., *Proc. Natl Acad. Sci. USA* 104: 10465-10469 (2007). Briefly, the proteins were transferred to a PVDF membrane, and membranes were blocked with BLOTTO (5% nonfat dry milk and 0.1% Tween 20 in PBS), and incubated with antisera generated against ME2, phospho-AKT380, phosphor-473, AKT1/2, phosphor-ERK1/2, ERK1, vimentin, GATA-1 or β-tubulin antibodies, respectively. Membranes were washed in PBS plus 0.1% Tween 20 and probed with anti-rabbit or anti-mouse HRP-conjugated secondary antibody (both at 1:10,000 dilution), and proteins were detected using the ECL Plus chemiluminescence detection reagent (Amersham Biosciences).

Proliferation Assay:

Control and ME2 deficient cell lines were plated in 6-well plate at a density of $1\times10^5$ cells/well and maintained at 37° C. in a 5% $CO_2$ incubator. After 24, 72, 120 and 168 hours of initial plating, 0.5 ml cells were diluted into 10 ml of Hanks' buffer and counted by Coulter counter. All samples were assayed in triplicate to generate proliferation curves, as described in Benson et al., *Nature* 441: 451-456 (2006). For the clonogenic assay, A549 with stably expression ME2 knockdown and control shRNA cells were seeded in a 6-well plate at a density of 200 cells per well. Colonies were fixed with 10% formaldehyde for 5 min and stained with 0.5% crystal violet for 30 min and counted with NIH image software.

Annexin-V Apoptosis Assay:

Apoptosis was measured by staining with the Nexin reagent using a Nexin kit and counting on the Guava PCA-96 system (Guava Technologies) as per the manufacture's protocol. Briefly, cells were harvested and re-suspended in 100 µl of 1× Nexin buffer, and then mixed with 100 µl of Annexin-V-PE, and Nexin 7-AAD. The cells were allowed to incubate for 20 minutes at room temperature and analyzed in the Guava flow cytometer.

Determination of Cellular Reactive Oxygen Species (ROS):

Intracellular ROS production was measured by staining with $CM-H_2DCFDA$. $CM-H_2DCFDA$ is a cell-permeant indicator for ROS that is nonfluorescent until removal of the acetate groups by intracellular esterases and oxidation occurs within the cell. The procedure for measuring ROS was carried out as described in Trachootham et al., in *Cancer Cell*. 10: 241-252 (2006), with minor modifications. Briefly, A549 cells transduced with shRNA lentiviral particles or control vector were selected with puromycin for 2 weeks, and then incubated with 5 µM $CM-H_2DCF-DA$ for 3 hours, followed by flow cytometry using a FACSCalibur equipped with CellQuest Pro software. Superoxide radicals ($O_2^-$) were measured separately using the MitoSOX™ reagent according to the manufacturer's protocol (Invitrogen). In brief, cells with or without ME2 knockdown were incubated with 5 µM MitoSOX™ reagent for 10 minutes at 37° C., then washed three times and observed under a fluorescence microscope using the Rhodamine filter and Axiovision software for capturing images (Zeiss, Germany).

Determination of Oxidative Damage to Mitochondrial Membranes:

Mitochondrial membrane lipid peroxidation was detected as described in Trachootham et al., in *Cancer Cell*. 10: 241-252 (2006). A549 cells transduced with shRNA lentiviral particles or control vector were selected with puromycin for 2 weeks, and then labeled with 50 nM NAO for 20 min and analyzed by flow cytometry using FL2 or 3 filters and Cell Quest software analysis data (Becton Dickson).

Xenograft Model in Nude Mice:

Animal experiments were performed under federal guidelines and approved by the Institutional Animal Care and Use Committee (IACUC) of the Beth Israel Deaconess Medical Center (Approval number 0342007). A549 xenografts in nude mice were generated by following the description of Verrax et al., in *Biochem. Pharmacol*. 72: 671-680 (2006). Briefly, approximately $10^7$ ME2 deficient or control A549 cells resuspended in 200 µl of a serum-free culture medium/Matrigel mixture (1:1) were subcutaneously injected into the right and left flanks of male nude/nu/nu athymic mice, respectively. Tumor-bearing mice were sacrificed after 6-8 weeks and tumor masses were measured or imaged before excision. Tumor lysates were prepared by homogenization of tumor tissues in RIPA lysis buffer and were resolved by SDS-PAGE and transferred onto PDVF membranes and immunoblotted with anti-ME2 antibody and normalized by β-tubulin as a loading control.

Intracellular ATP Measurements:

Intracellular ATP levels in control and ME2 deficient cells were measured by ATP Bioluminescence Assay Kit CLS II (Roche, Germany), according to manufacturer's instructions. Briefly, cells were diluted to a concentration of $10^7$ cells/ml, then add 9 volumes of boiling lysis buffer (100 mM Tris, 4 mM EDTA, pH 7.75) and incubated for another 2 minutes at 100° C. Cell lysates were collected by centrifugation and pelleting at 1000×g for 1 minute, and 50 µl of samples were transferred into a MTP-well, and mixed with 50 µl luciferase reagent. Luminescence was measured using a luminescence reader (Molecular Devices) and normalized for protein concentration.

Cell Adhesion and Migration Assay:

To study the effect of ME2 depletion on cell adhesion ability, ME2 knockdown or control cells were seeded in 6-well plate and the non-adherent cells in medium were counted. Cell migration assay were performed using a Chemotaxis Cell Migration Assay kit, as described by manual. In brief, A549 cells with or without ME2 knockdown were harvested and resuspended to 1×106 cells per ml, then 500 µL of cells were placed per well. Cells were incubated for 6 hours in a $CO_2$ incubator. After removing non-migrating cells from coated chambers with a swab, cells were stained, and migratory cells were solubilized with extraction buffer and read at an OD of 540-570 nm.

Metabolite Profiling:

To determine differences in metabolite profiles between ME2-depleted and control cells, metabolite extracts were prepared and then analyzed using liquid chromatography tandem mass spectrometry (LC-MS) as described in Ren et al., *PLoS One* 5:e12520 (2010).

$^{13}$C-Glucose Labeling and $^{13}$C Metabolite Isotopologue Distributions Analysis:

Two separate tracer experiments were performed, each with duplicate samples. For the first experiment, A549 cells were cultured in 10 cm plates for 24 hr in Gln-minus Hams/F12 medium (Sigma) supplemented with 0.2% $^{13}C_6$-Glc (resulting in 50% of glucose as $^{13}C_6$-Glc) or 1 mM $^{13}C_5,^{15}N_2$-Gln (Sigma) and 10% dialyzed FBS (10 kD MWCO, Atlanta Biological). The second experiment was performed similarly with a custom Hams/F12 medium without glucose and Gln (Cellgro, Mediatech) but supplemented with 0.2% $^{13}C_6$-Glc+1 mM unlabeled Gln (100% of glucose as $^{13}C_6$-Glc) or with 1 mM $^{13}C_5,^{15}N_2$-Gln+0.2% unlabeled Glc. Medium samples were taken for $^1$H NMR analysis at 0, 3, 6, 12, and 24 h. At the end of the incubation, cell plates were washed 3 times quickly with cold PBS to remove medium component, vacuum drained, cell metabolism was quenched with cold acetonitrile (−20° C.) and both polar and lipid metabolites were extracted in acetonitrile:$H_2O$:chloroform (2:1.5:1, v/v) as described previously in Fan et al., *Handbook of Metabolomics*: in press, 2012 and Le et al., *Cell Metabolism* 15:110-121 (2012). Metabolites were analyzed by NMR, their MTBSTFA derivatives by gas chromatography-mass spectrometry (GC-MS), and by direct-infusion Fourier transform-ion cyclotron resonance-MS (FT-MR-MS) as described previously in Fan et al., *Metabolomics* 1:325-339 (2005), Lane et al., *Analytica Chimica Acta* 651:201-208, (2009), and Lorkiewicz et al., *Metabolomics: Office Journal of the Metabolomic Society* 8:930-939 (2012). Medium metabolites were extracted in cold 10% trichloroacetic acid to precipitate proteins and lyophilized before MTBSTFA derivatization, followed by 1D $^1$H NMR analysis as described in Fan et al., *Metabolomics* 6:265-179 (2010). The metabolites were identified and quantified using XCalibur software (ThermoFinnigan) for the MS data and MestReNova software (Mestrelab Research) for the NMR data. Results from both NMR and GC-MS measurements were normalized to the total protein weight determined by the BCA method (Pierce).

Example 1: ME2 Expression in Clinical Tumor Samples

We investigated ME2 expression in clinical tumor samples (from Protein Biotechnologies) by Western blotting. Eighty tumor specimen representing 13 types of solid tumors were probed by Western blotting with ME2 antibody (Sigma). ME2 overexpression was present in the majority of analyzed tumors, including lung (Table I and FIG. 1A), bladder, breast, esophagus, liver, ovary, prostate and skin. About 90% of the lung tumors overexpressed ME2 as compared to normal lung tissue (Table I and FIG. 1A). Moreover, we also investigated ME2 expression in a human tumor tissue array from US Biomax (anti-ME2 antibody from Sigma) and this data provided overall corroboration of the Western blot data. Increased ME2 expression was observed in lung cancer tissue, as compared to normal adjacent lung tissue (FIG. 1B). Depletion of ME2 can also markedly inhibit cell proliferation of K562 (erythroleukemia) cells, MCF-7 (breast) cells, and WM983-B (melanoma) cells. These data suggest that ME2 may play an important role in various cancers, such as any described herein.

TABLE I

| Samples | Diagnosis | Grade | Stage | TNM | Sex | Age |
|---|---|---|---|---|---|---|
| 1 | Papillary Adenocarcinoma | 2 | IIIA | T3N0M0 | M | 42 |
| 2 | Adeno-Squamous Cell Carcinoma | 2 | I | T2N0M0 | M | 62 |
| 3 | Large Cell Carcinoma | 3 | III | T3NxM0 | M | 26 |
| 4 | Small Cell Carcinoma | 3 | IIB | T2N1M0 | M | 73 |
| 5 | Squamous Cell Carcinoma | 2 | I | T2N0M0 | M | 45 |
| 6 | Squamous Cell Carcinoma | 3 | n/a | n/a | M | 37 |
| 7 | Squamous Cell Carcinoma | 2 | I | T1N0M0 | M | 58 |
| 8 | Adenocarcinoma | 2 | II | T2N0Mx | F | 51 |
| 9 | Small Cell Carcinoma | n/a | II | n/a | F | 56 |
| 10 | Spindle Cell Carcinoma | n/a | I | T2N0M0 | F | 25 |
| 11 | Lung Tumor Lysate | n/a | n/a | n/a | n/a | n/a |
| 12 | Normal Liver | n/a | n/a | n/a | M | 50 |
| 13 | Normal Lung | n/a | n/a | n/a | n/a | n/a |
| 14 | Normal lung | n/a | n/a | n/a | M | n/a |

Example 2: Effect of Dimethyl Malate in Lung Cancer Cells

Figure 8:
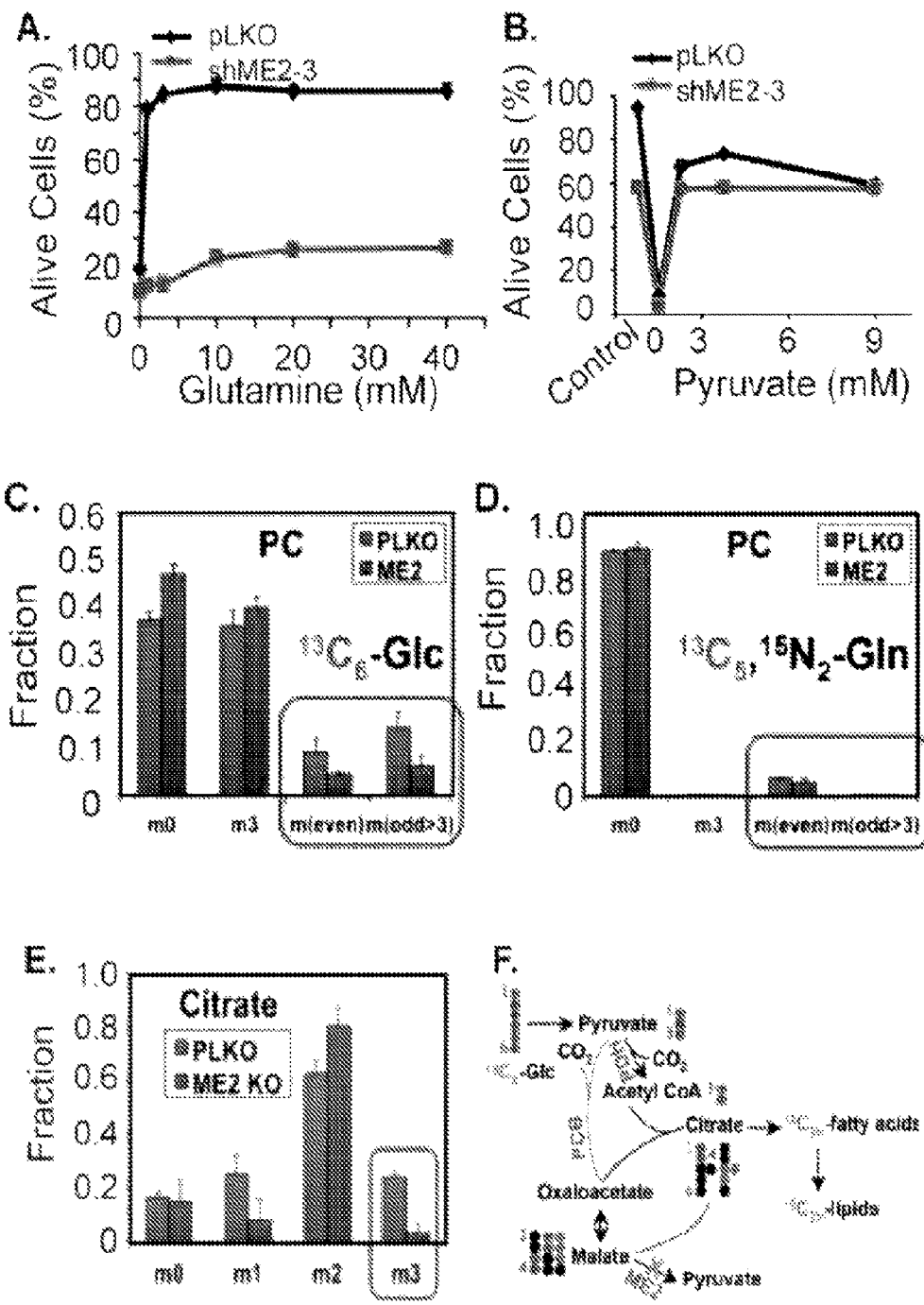
FIG. 8 shows that survival of A549 cells with ME2 knockdown was dependent on glucose. A: Exogenous supplementation of glutamine failed to rescue ME2 depletion induced cell death. A549 control or ME2 knockdown cells were grown in Hams/F12 based medium without glucose, pyruvate and glutamine. Different concentrations of glutamine were supplemented as indicated. The alive cells were stained with Nexin/7-ADD and analyzed by FACS. B: Exogenous supplementation of pyruvate can rescue ME2 depletion induced cell death. A549 control or ME2 knockdown cells were grown in Hams/F12 based medium without glucose, pyruvate and glutamine. Different concentrations of pyruvate were supplemented as indicated. The alive cells were stained with Nexin/7-ADD and analyzed by FACS. C and D: The effect of ME2 knockdown on de novo synthesis of PC is greater with $^{13}C_6$-Glc than with $^{13}C_5$, $^{15}N_2$-Gln as tracer, as analyzed by FT-ICR-MS. E: Inhibition of $^{13}C_3$-citrate synthesis from $^{13}C_6$-Glc by ME2 knockdown, as determined by GC-MS. F: $^{13}C$ atom-resolved tracing from $^{13}C_6$-Glc through glycolysis, the Krebs cycle without or with input of pyruvate carboxylation, and biosynthesis of fatty acyl chains with even number of $^{13}C$ ($^{13}C_{2n}$) in lipids via citrate; $^{13}C$ atoms from the first turn of Krebs cycle without or with pyruvate carboxylation; solid and dashed arrows: single and multiple-step reactions; single and double-headed arrows: irreversible and reversible reactions; PDH: pyruvate dehydrogenase; PCB: pyruvate carboxylase: ME2: malic enzyme 2. G and H: Effects of ME2 knockdown on the levels and fractional distribution of $^{13}C$ isotopologues of malate, as analyzed by GC-MS; rectangles depict $^{13}C_2$- (m2) and $^{13}C_3$-malate (m3) species as markers of the first turn of the Krebs cycle without and with pyruvate carboxylation input, respectively. Metabolite data were averages of duplicate samples and shown with SEM as error bars. For C, D, E, G, and H, data are shown for PLKO (left bars) and ME2 KO (right bars).
Figure 8:
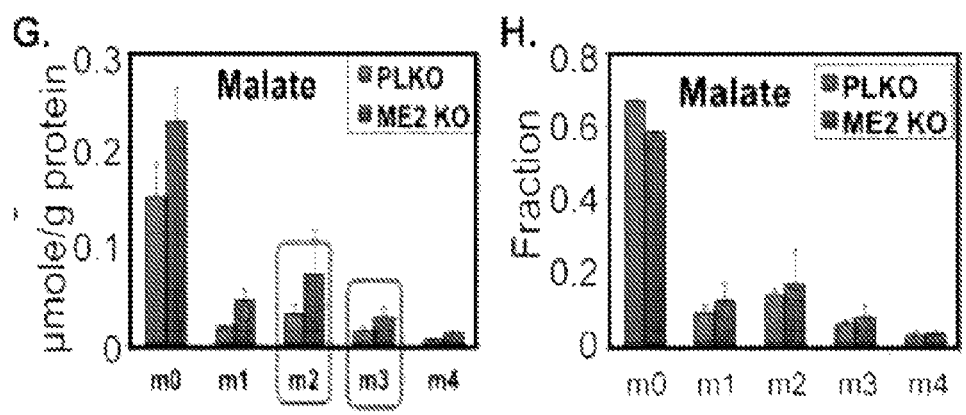

Depletion of ME2 inhibited cell proliferation and induced apoptosis and differentiation in the A549 non small cell lung cancer (NSCLC) cell line. As described herein, ME2 is expressed in this cell line, and the function of ME2 is to convert mitochondrial malate into pyruvate. Thus, we observed that knockdown of ME2 led to malate accumulation in mitochondria (FIGS. 2A-2B) as analyzed by two different methods. This accumulation was mediated through reduced ME2 activity, as evidenced by the accumulation of $^{13}C_2$- and $^{13}C_3$-malate (m2 and m3 in FIG. 8G) without changes in their fractional enrichment, which is consistent with a block in malate catabolism via ME2. $^{13}C_2$- and $^{13}C_3$-malate is presumably derived from $^{13}C_6$-Glc via the sequence of glycolysis and the first turn of the Krebs cycle without or with input of pyruvate carboxylation, respectively (FIG. 8F).

To test whether malate accumulation may damage mitochondrial function and further inhibit cell growth, an exogenous form of malate was delivered in vitro. Exogenous malate may mimic the phenotype-induced by ME2 knockdown. Therefore, we supplemented exogenous cell-permeable malate (Heart et al., *Am. J. Physiol.* 296: E1354-1362 (2009)) in A549 cell growth media and compared the phenotype with ME2 knockdown cells. DMM, being cell permeable, was used as an exogenous substitute for malate.

ME2 knockdown cells were prepared by using various constructs containing ME2 short hairpin RNAs (shRNA). We produced recombinant lentiviral particles by expressing constructs containing ME2 shRNA and establishing stable clones of A549 cells. Three independent constructs, shME2-1, shME2-2 and shME2-3, were used to generate stable cell lines; all showed marked decrease in ME2 expression, as compare to a control lentivector (pLKO).

Figure 2:
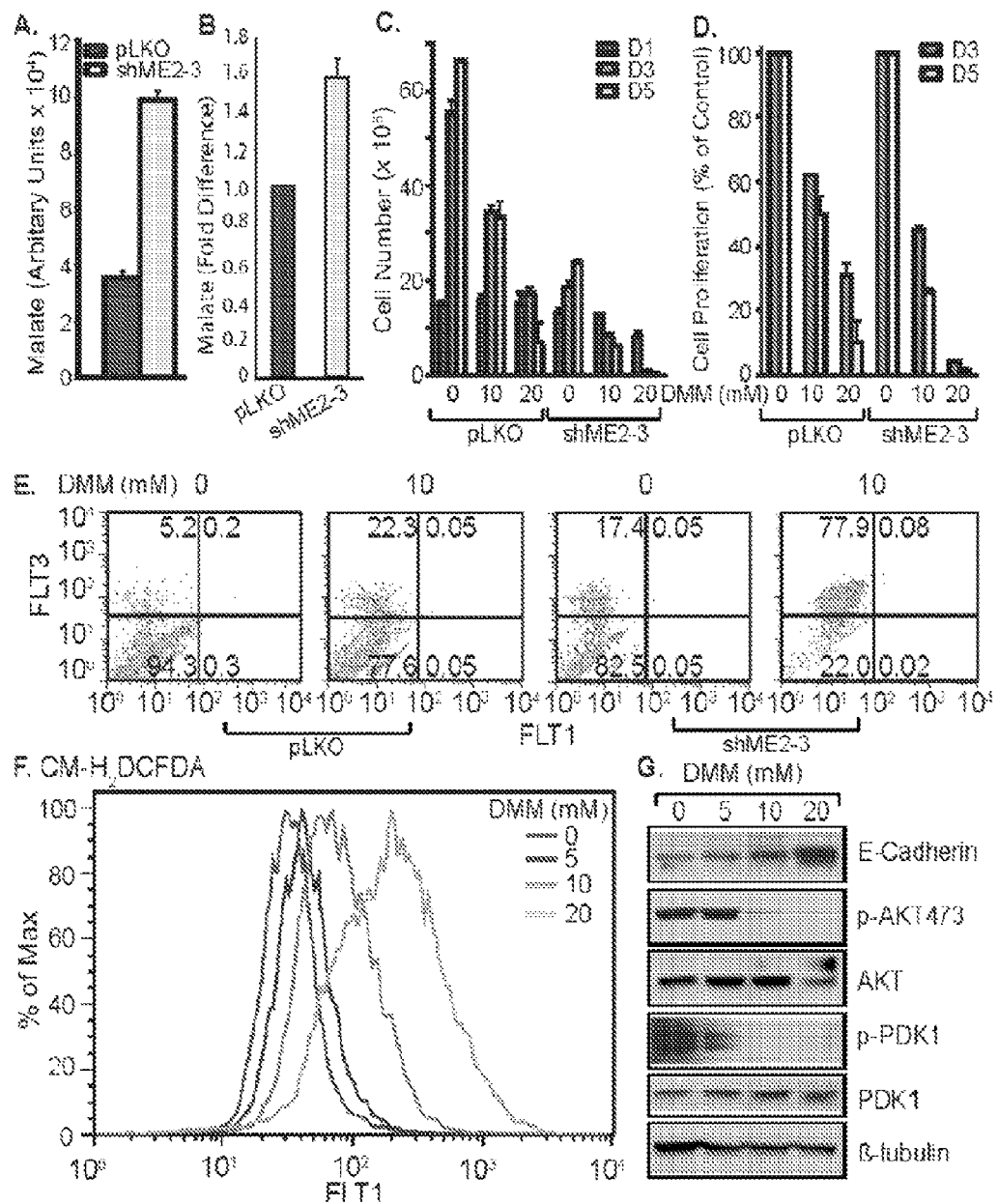
FIG. 2 shows that supplementation of exogenous cell-permeable dimethyl malate (DMM) mimics the malic enzyme 2 (ME2) deficient phenotype in A549 lung cancer cells. A: Depletion of ME2 in A549 cells (shME2-3) caused malate accumulation, as compared to A549 control having an empty vector shRNA (pLKO). Concentrations of malate [arbitrary units] were analyzed by LC-MS. B: Malate in ME2 knockdown cells (shME2-3) and control (pLKO) cells were analyzed by a malate assay kit. C: Treatment of ME2 knockdown cells (shME2-3) and control (pLKO) cells with DMM inhibited cell proliferation. Data are provided for administration of 0, 10 mM, or 20 mM of DMM and for cells on day 1, 3, and 5 (D1, D3, and D5, respectively) after plating. D: ME2 knockdown cells (shME2-3) showed higher sensitivity to exogenous DMM treatment, as compared to pLKO cells. Data are provided as a percentage of control with 0 mM DMM. E: Exogenous DMM treatment induced necrosis in control (pLKO) and ME2 knockdown cells (shME2-3). F: Exogenous DMM treatment enhanced ROS production, as determined by the CM-$H_2$DCFDA indicator. Different concentrations of DMM were analyzed (from 0, 5 mM, 10 mM, to 20 mM data are provided from left to right). G: Exogenous DMM treatment induced differentiation of A549 cells, as well as inhibition of Akt and PDK1 phosphorylation (p-AKT473 and p-PDK1, respectively).

As shown in FIGS. 2C-2D, the proliferation of A549 cells was significantly inhibited when treated with 10 and 20 mM DMM. Inhibition was observed in both control A549 cells (pLKO) and ME2 knockdown A549 cells (shME2-3). Moreover, ME2 knockdown cells were more sensitive to treatment with DMM treatment, as compared to control cancer cells (FIGS. 2C-2D).

To understand this increased sensitivity, we also studied cell death using an annexin V assay. As shown in FIG. 2E, treatment with DMM induced necrosis in A549 cells rather than apoptosis. Cells depleted of ME2 were more sensitive to DMM treatment consistent with enhanced ROS production in ME2 knockdown A549 cells (FIG. 11E), exogenous DMM enhanced production of ROS, as measured with CM-H$_2$DCFDA (FIG. 2F). Just as depletion of ME2 in A549 cells can inhibit basal Akt and PDK1 activity, exogenous DMM also inhibited basal Akt and PDK1 activity in vitro and increased E-cadherin expression in vitro (FIG. 2G). These data suggest that supplementation with exogenous cell-permeable malate can mimic the phenotype-induced by ME2 knockdown, though there may be some difference in the modality of cell death (e.g., necrosis, apoptosis). These data also suggest that cell death-induced by DMM treatment may be due to increased ROS. Accordingly, these data show that knockdown of ME2, e.g., by using malate, or a derivative thereof, as described herein, could be implemented to treat a proliferative disorder, e.g., any cancer described herein.

Example 3: Effect of ROS on Treatment with DMM

Both knockdown of ME2 and treatment with exogenous DMM can enhance ROS production in A549 cells. Further, treating ME2 depleted cells with n-acetyl-cysteine (NAC) failed to rescue cell death induced by ME2 knockdown. To test the role of ROS in treatment with DMM, we inhibited ROS in DMM-treated cells and determined whether the phenotype in A549 cells could be rescued. In particular, ROS was inhibited by using antioxidants of NAC and glutathione (GSH).

Figure 3:
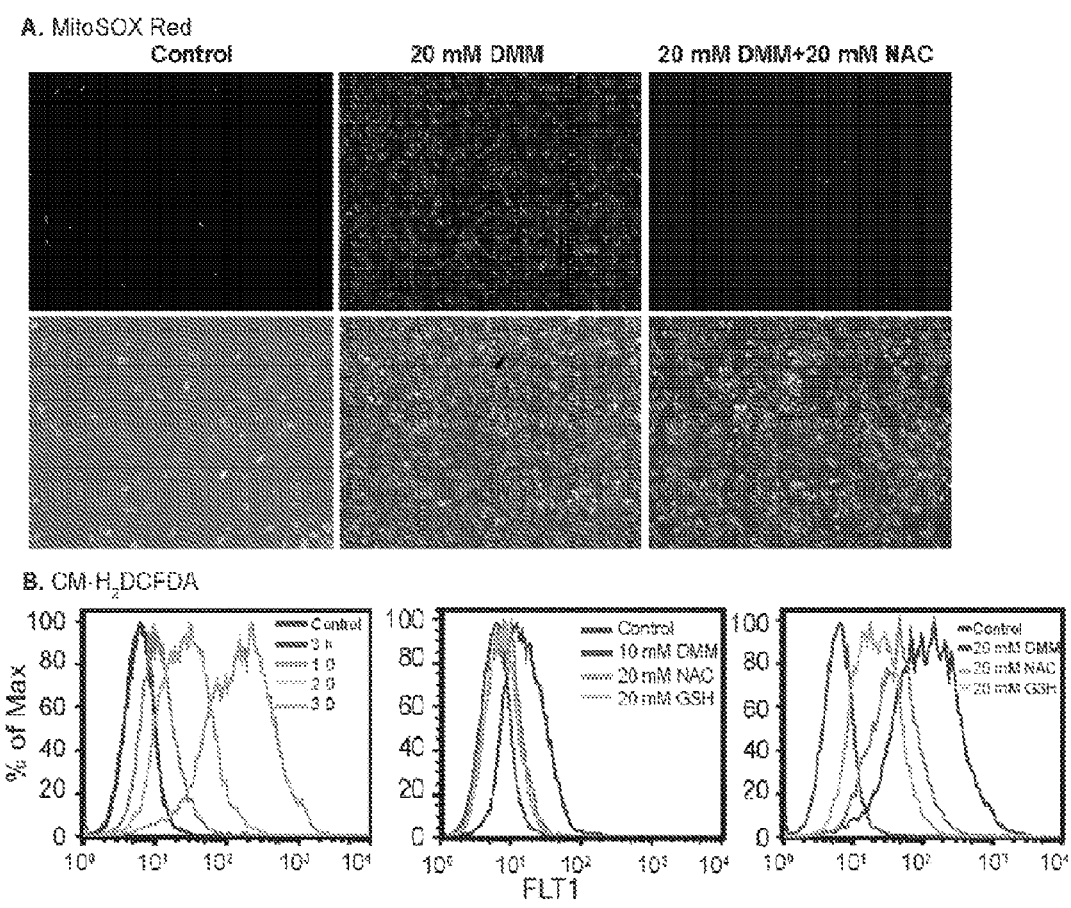
FIG. 3 shows that antioxidants N-acetyl-cysteine (NAC) and reduced glutathione (GSH) rescued exogenous DMM-induced phenotype in A549 lung cancer cells. A: Accumulation of mitochondrially generated superoxide in A549 cells were detected by indicator MitoSOX™ (top: MitoSOX™-stained cells; bottom: phase contrast). Data are representative of two independent experiments. B: NAC and GSH inhibited the production of ROS, which in turn was induced by exogenous DMM. ROS were detected by flow cytometry using indicator CM-$H_2$DCFDA. Each histogram represents three experiments. Left: ROS production is provided as a function of time, where data are provided for cells treated with DMM and for the following curves (from left to right): control, after 3 hours (3 h), one day (1 D), two days (2 D), and three days (3 D). Center: Cells were treated with 10 mM DMM, either with or without 20 mM NAC or 20 mM GSH. Data are provided for the following curves (from left to right): control, GSH, NAC, and DMM. Right: Cells were treated with 20 mM DMM, either with or without 20 mM NAC or 20 mM GSH. Data are provided for the following curves (from left to right): control, GSH, NAC, and DMM. C: Administration of NAC or GSH inhibited DMM-induced cell death. D: Administration of NAC or GSH inhibited DMM-induced cell differentiation and rescued the Akt inhibition (as determined by phosphorylation of Akt, p-AKT473).
Figure 3:
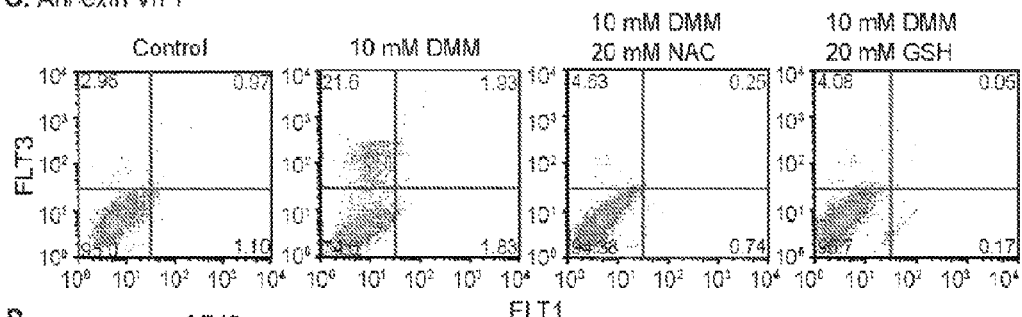
Figure 3:
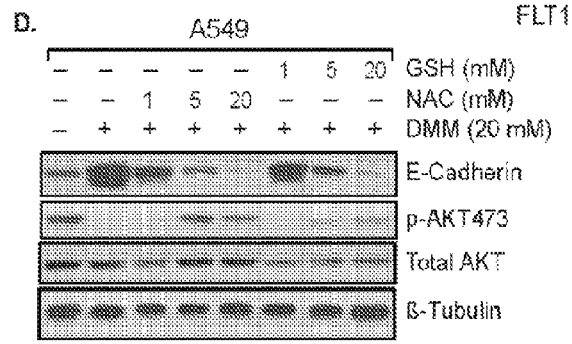

We measured the ROS source using MitoSOX™ Red, a reagent that selectively targeted to the mitochondria. Once in the mitochondria, MitoSOX™ Red is oxidized (e.g., by superoxide) and exhibits red fluorescence. A549 cells were treated with 20 mM DMM for four days, and these cells showed increased presence of superoxide (FIG. 3A, center column). In contrast, when the cells were incubated with both DMM and 20 mM NAC, decreased levels of superoxide production was observed (FIG. 3A, right column). These data indicate that at least one ROS source induced by DMM is mitochondrial.

DMM-induced ROS production in A549 cells was time-dependent, as detected by CM-H$_2$DCFDA (FIG. 3B, left). Exogenous addition of NAC or GSH inhibited DMM-induced ROS production (FIG. 3B, middle and right). As NAC and GSH can scavenge ROS, we speculated that NAC and GSH may rescue the phenotype-induced by DMM treatment. As expected, NAC and GSH almost completely inhibited DMM-induced cell death (FIG. 3C).

Furthermore, DMM can beneficially induce differentiation, such as by inhibiting phosphorylation of Akt. However, when cells were incubated with DMM in combination with NAC or GSH, both NAC and GSH reversed the DMM-induced differentiation and rescued basal Akt activity in A549 cells (FIG. 3D). Without wishing to be limited by mechanism, these data suggest that ROS plays a role in mediating the anti-proliferative effects observed when intercellular levels of malate, or a derivative thereof, are increased. Accordingly, these data show that malate, or a derivative thereof, as described herein, could be implemented to treat a proliferative disorder, e.g., any cancer described herein.

Example 4: Targeting of Cancer Cells with DMM

Both ME2 knockdown and DMM treatment enhance ROS production, and various chemotherapeutic agents enhance ROS in vivo to provide a targeted, therapeutic effect. Accordingly, we tested whether DMM could selectively induce ROS and promote apoptosis in cancer cells.

Figure 4:
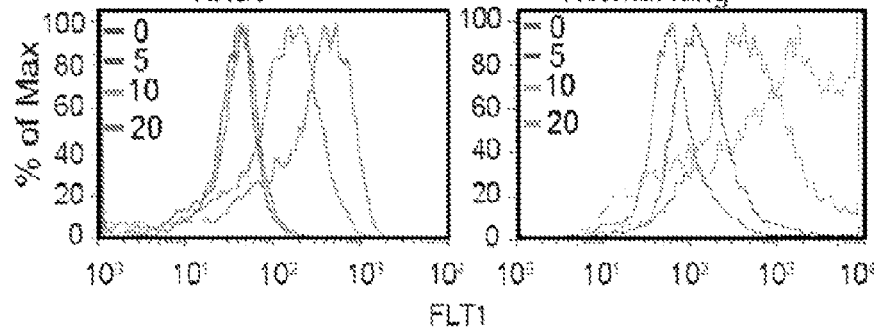
FIG. 4 shows that DMM selectively targeted tumor cells. A: Treatment with DMM induced ROS production in both normal human derived fibroblast (NHDF) and normal lung epithelial cells (Normal lung). ROS was detected by flow cytometry using indicator CM-$H_2$DCFDA. Data are provided for the following curves (from left to right): 0, 5 mM, 10 mM, or 20 mM DMM. B: DMM selectively induced cell death in lung tumor cells (A549), as compared with normal human derived fibroblast (NHDF) and normal lung epithelial cells (Normal lung). Cell death was analyzed by Annexin V reagent. Each histogram is representative of three experiments
Figure 4:
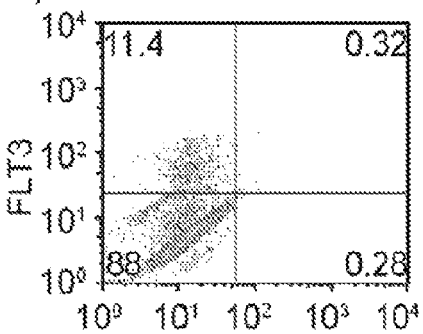
Figure 4:
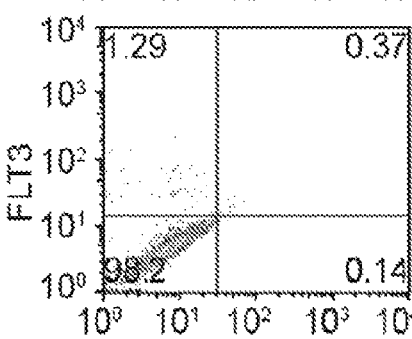
Figure 4:
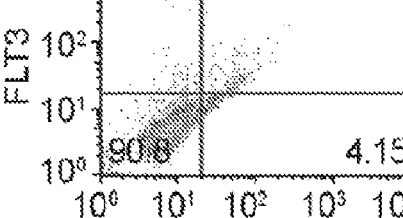

ROS production was measured in both normal and tumor cells. As shown in FIG. 4A, various concentrations of DMM enhanced ROS production in two normal cell lines for fibroblast and epithelial cells. As described herein in FIG. 2F, ROS production was also observed in A549 cells. Interestingly, DMM selectively induced cell death in the A549 cancer cell but not in the normal cell lines (FIG. 4B). Without wishing to be limited by mechanism, targeted therapy may arise due to increased resistance of normal cells to ROS-induced cell death. Accordingly, these data show that increased levels of malate or a derivative thereof, e.g., by using any malate or derivative described herein, could be implemented to treat a proliferative disorder, e.g., any cancer described herein.

Example 5: Combination Therapy to Suppress In Vivo Tumor Growth

The above observations suggest that knockdown of ME2 in tumor cells could significantly inhibit cell proliferation and differentiation, as well as increase apoptosis. To study the effects of stable ME2 gene knockdown on the in vivo tumorigenicity of A549 cells, we injected vector control and ME2 knockdown clones (shME2-2 and shME2-3) subcutaneously into nude mice and examined tumor formation and progression. ME2 knockdown cells significantly inhibited tumor growth in vivo and possessed increased sensitivity to the chemotherapeutic effects of cisplatin.

Figure 5:
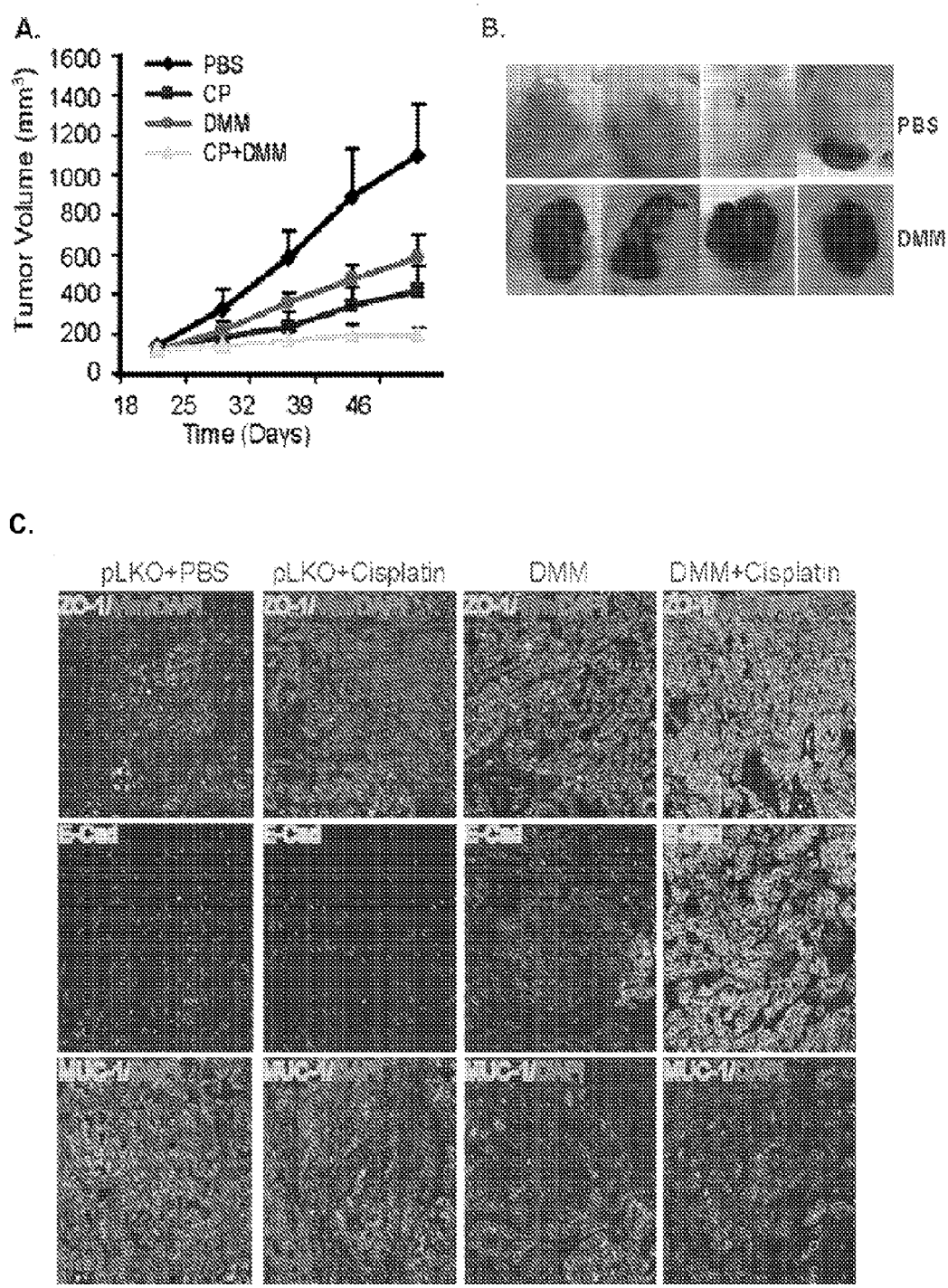
FIG. 5 shows that DMM synergistically inhibited cisplatin-treated tumor growth. A: The combination of cisplatin (CP) and DMM synergistically inhibited tumor growth in A549 cells. Approximately $5 \times 10^6$ control pLKO cells were subcutaneously implanted into female athymic nude mice. Mice were treated with DMM, cisplatin (CP), a combination of cisplatin with DMM (CP+DMM), or control (PBS), as described herein. Tumor size was measured and calculated. B: Direct injection of DMM into xenograft tumors caused shrinkage and ulceration of tumors, as compared to control with PBS. C: The combination of cisplatin with DMM inhibited in vivo expression of Mucin-1 (bottom row, MUC-1) and increased expression of differentiation markers E-cadherin (middle row, E-Cad) and ZO-1 (top row).

Further studies were conducted to study a combination therapy including a malate derivative with cisplatin. As shown in FIG. 5A, administration of 0.5 g/kg of DMM significantly inhibited A549 tumor growth in vivo. Furthermore, the combination of DMM and cisplatin displayed synergistic effects on tumor growth. DMM also displayed anti-proliferative effects when directly injection into A549 xenograft tumors. As shown in FIG. 5B, we observed decreases in tumor size, as well as ulceration of the tumor tissue.

This combination therapy also induced tumor cell differentiation in vivo, as observed by several markers. E-cadherin and ZO-1 are two important markers of epithelial cell differentiation, where increased mucin production is observed in various adenocarcinomas. The combination of DMM and cisplatin induced tumor cell differentiation in vivo, where this treatment increased expression of differentiation markers E-cadherin and ZO-1, as well as inhibited expression of mucin-1 (FIG. 5C). Collectively, these data suggest that ME2 plays crucial role in the tumorigenicity of lung cancer, and that ME2 is a potential target for cancer therapy. Accordingly, these data show that a combination of malate, or a derivative thereof, with an ME2 inhibitor, an antineoplastic agent, e.g., cisplatin, and/or a glycolysis inhibitor can be used to increase the effectiveness of cancer treatment.

Example 6: Inhibition of Modified ME2 with DMM

Figure 6:
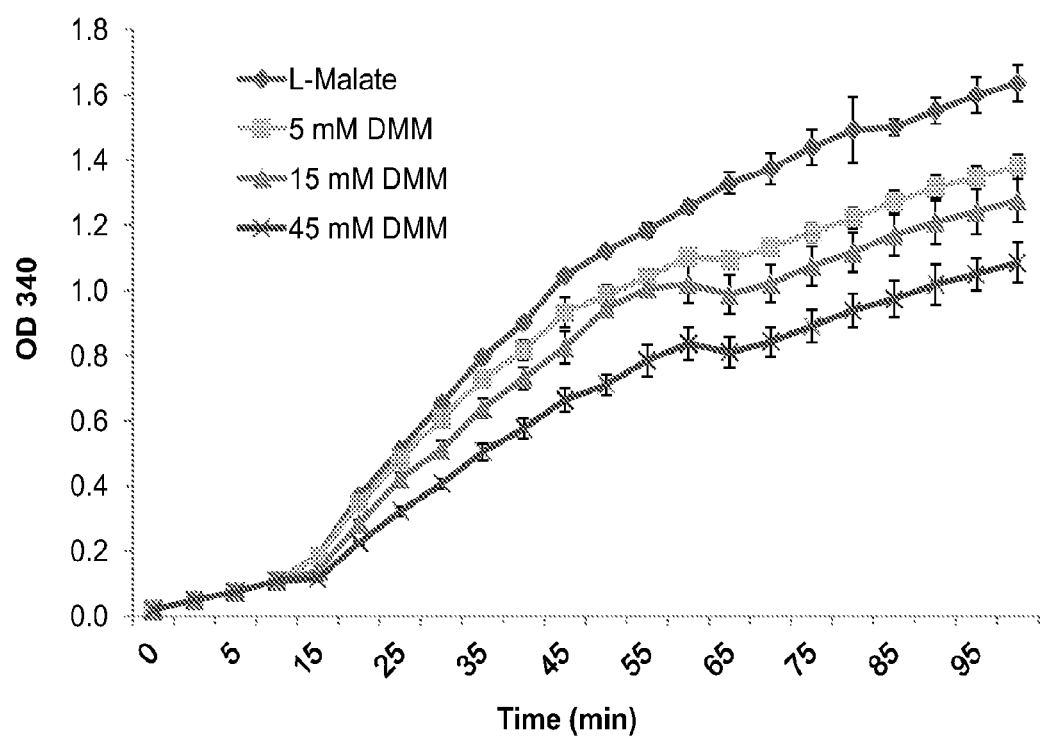
FIG. 6 shows the inhibitory effect of DMM on the in vitro activity of modified ME2. Modified ME2 is a recombinant ME2 protein having a C-terminus His tag and lacking the mitochondrial targeting sequence (ME2-C) was prepared, as described in Loeber et al., J. Biol. Chem. 266:3016-3021 (1991). The 200 µl assay mixture contained 30 mM of Tris-HCl (pH 7.4), 15 mM of L-malate (pH 7.4), 1 mM of NAD$^+$, 2 mM of MnCl$_2$, and 60 nM of ME2-C. Different concentrations of DMM (pH 7.4) were tested, namely 5, 15 and 45 mM. The absorbance of the solution at 340 nm was monitored continuously with a Beckman Coulter DTX 880 multimode spectrophotometer at 37° C.

To further determine compounds that can be used to inhibit ME2 and/or increase intracellular malate, or a derivative thereof, an ME2 assay was established. Accordingly, a modified ME2 protein was constructed using a human ME2 expression vector and a bacterial expression system (*E. coli* BL21(DE3)) with a cleavable FLAG tag. Both N- and C-terminal constructs were assessed for protein production, and the mitochondrial targeting sequence was deleted in the constructs, as described in Loeber et al., J. Biol. Chem. 266:3016-3021 (1991), which is incorporated herein by reference. Kinetic experiments were performed with C-terminal tagged ME2 (ME2-C) and with an assay mixture containing 30 mM of Tris-HCl (pH 7.4), 15 mM of L-malate (pH 7.4), 1 mM of NAD+, 2 mM of $MnCl_2$, and 60 nM of ME2-C. The specific activity of the ME2 preparation was about 20.11 µmol/min/mg at 37° C., which is similar to published values for human liver ME2 (21.9 mmol/min/mg), and about 12.54 mmol/min/mg at 25° C. Addition of DMM decreased the activity of ME2-C, as show in FIG. 6. Accordingly, these data show that ME2 can be used to identify additional malate derivatives that are useful for treating a proliferative disorder, such as any cancer described herein.

Example 7: Knockdown of ME2 Levels Impaired Proliferation of Cancer Cells

Knockdown of ME2 using shRNA was effective in reducing ME2 protein levels and decreased cell proliferation in several cells lines including the A549 non small cell lung cancer (NSCLC) cell line, H1650 lung cancer cell line resistant to TKI inhibition, and MCF-7 breast cancer cell line.

Figure 7:
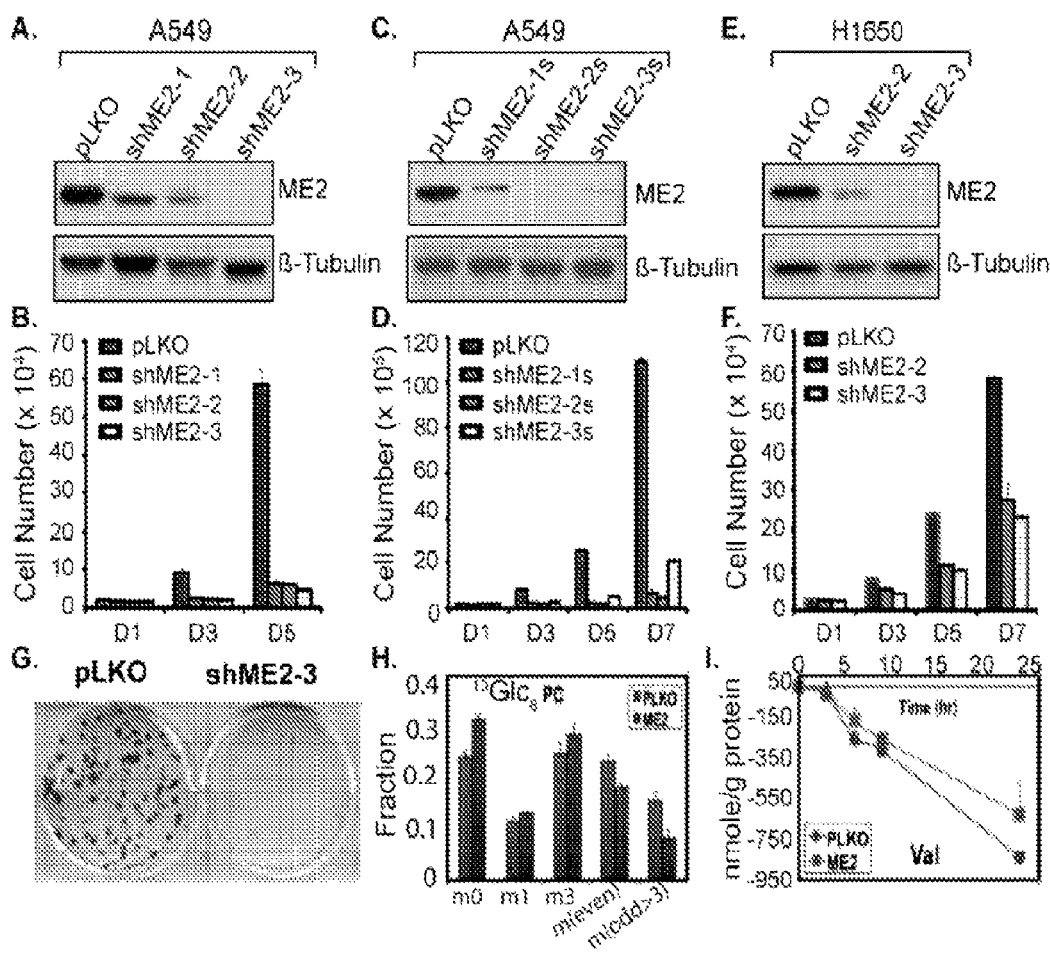
FIG. 7 shows the effects of independent shRNAs targeting ME2 on lung cancer proliferation. A: Western blot analysis using an ME2 antibody (Sigma) of lysate from respective pools of A549 cells transduced with three independent ME2 shRNA lentiviruses, following selection of puromycin for 10 days. Data are representative of at least three independent experiments. All three pools showed marked ME2 silencing. B: Cell proliferation in A549 cells transduced with the indicated shRNA lentiviral constructs as described in "A". Data are representative of three independent experiments. C: Western blot analysis of cellular extracts in single clones of A549 cells demonstrating effective knockdown of ME2 levels. Data are representative of at least three independent experiments. D: Cell proliferation of A549 single cell clones with ME2 knockdown derived from the corresponding pools as described in "C". Data are representative of three independent experiments. E: Western blot analysis of cellular extracts in H1650 cells demonstrating effective knockdown of ME2 levels. F: Cell proliferation in H1650 cells transduced with the indicated shRNA lentiviral constructs as described in "E". G: Knockdown of ME2 in A549 cells inhibited colony formation. H: Fractional changes in $^{13}$C mass isotopologues (differing in the number of $^{13}$C atoms) of phosphatidylcholines (PC) in ME2 knockdown cells; m0: all $^{12}$C, m3: $^{13}C_3$-PC ($^{13}$C labeling in glycerol backbone only, m(even): $^{13}C_{even\#}$-PC ($^{13}$C labeling in fatty acyl chains only), m(odd>3): $^{13}C_{odd\#>3}$-PC ($^{13}$C labeling in fatty acyl chains plus glycerol backbone). Data are provided for PKO (left bars) and ME2 (right bars). I: Time courses of valine consumption in ME2 knockdown cell medium, as determined from $^1$H NMR data. Metabolite data were averages of duplicate samples and shown with SEM as error bars.
Figure 15:
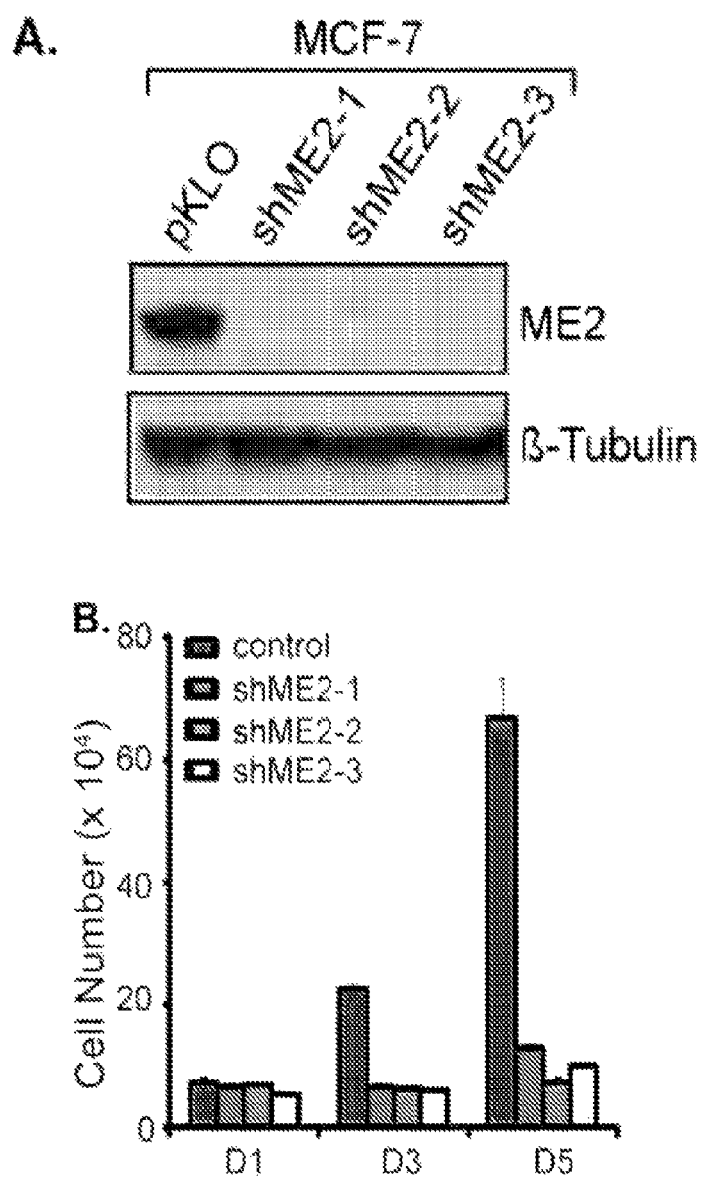
FIG. 15 shows effects on breast cancer cell proliferation of independent shRNAs targeting ME2. A: Western blot analysis using an ME2 antibody of lysate from pools of MCF-7 cells transduced with three independent ME2 shRNA lentiviruses, following selection of puromycin for 10 days. Data, are representative of at least three independent experiments. All three pools showed marked ME2 silencing. B: Cell proliferation in MCF-7 cells transduced with the indicated shRNA lentiviral constructs as described in "A". Data are representative of three independent experiments.

To investigate the effects of ME2 inhibition on tumor cells growth, we produced recombinant lentiviral particles expressing constructs containing ME2 short hairpin RNAs (shRNA) and established stable clones of A549 cells with shRNA-mediated suppression of ME2 as briefly described in Example 2 and further described herein. Three independent constructs, shME2-1, shME2-2 and shME2-3, were used to generate stable cell lines; all showed marked ME2 knockdown as compared to a control lenti-vector (FIG. 7A). The three pools (shME2-1, shME2-2 and shME2-3) with stable knockdown of ME2 were used to examine the role of ME2 in tumor proliferation. As shown in FIG. 7B, A549 cells with reduced ME2 protein levels proliferated much slower than their wild-type counterparts. Three single clones from the three independent ME2 shRNA pools were established, expanded, and renamed shME2-1s, shME2-2s, and shME2-3s. These clones displayed significant decrease in ME2 protein levels (FIG. 7C), and cell proliferation was markedly decreased (FIG. 7D). Depletion of ME2 also inhibited growth of other tumor cells; ME2 expression in H1650 (a lung cancer line resistant to TKI inhibition) and MCF-7 (a breast cancer line) were significantly reduced by shME2 RNA (FIG. 7E and FIG. 15A), which was accompanied by a dramatic inhibition of tumor cell proliferation (FIG. 7F and FIG. 15B). Depletion of endogenous ME2 also inhibited colony formation in vitro (FIG. 7G) (in A549).

To assess the effects of ME2 knockdown on tumor cell metabolism, we performed stable isotope-resolved metabolomics (SIRM) studies by incubating ME2 knockdown or control cells in uniformly $^{13}C$ labeled glucose ($^{13}C_6$-Glc or $^{13}Glc_6$) or $^{13}C/^{15}N$ labeled glutamine ($^{13}C_5,^{15}N_2$-Gln). A549 cells with ME2 KD showed a decrease in the $^{13}C_6$-Glc-derived fatty acyl chains (m(even) and m(odd>3), FIG. 7H) in the most abundant phosphatidylcholine (PC) lipids, and attenuated protein biosynthesis (as evidenced by decreased Val consumption from the medium, FIG. 7I), consistent with diminished cell proliferation. Accordingly, these data show that knockdown of ME2, e.g., by using an ME2 inhibitor, e.g., an RNAi agent, as described herein, could be implemented to treat a proliferative disorder, e.g., any cancer described herein.

Example 8: Survival of Cancer Cells with ME2 Knockdown and Dependence on Glucose Without wishing to be bound by theory, the knockdown of ME2 could reduce the ability of A549 cells to use glutamine and thereby impact cell survival/proliferation. We therefore excluded pyruvate, glucose, and glutamine from Hams/F12 medium and studied the dependence of ME2 knockdown cells on glutamine for their survival. As shown in FIG. 8A, both control and ME2 knockdown cells could not survive in Hams/F12 medium in the absence of pyruvate, glucose, and glutamine. Supplementation with glutamine rescued control cells more than ME2 knockdown cells. Pyruvate supplementation rescued both ME2 knockdown and control cells (FIG. 8B), suggesting that pyruvate produced by ME2 from malate plays a pro-survival role in A549 cells.

SIRM studies showed that glucose is the preferred substrate for supporting PC synthesis over glutamine, therefore could be the basis for the sensitivity of ME2 knockdown cells to glucose. In addition, the attenuating effect of ME2 knockdown on PC synthesis appeared to be greater with $^{13}C_6$-Glc than with $^{13}C_5,^{15}N_2$-Gln as tracer (FIGS. 8C and 8D). Moreover, the glucose-mediated anaplerotic input into the Krebs cycle via pyruvate carboxylation was attenuated in ME2 knockdown cells, as evidenced by the reduced fractional distribution of triply $^{13}C$ labeled citrate ($^{13}C_3$-citrate or m3 in FIG. 8E), which is a unique marker of pyruvate carboxylation (FIG. 8F). Citrate is regularly diverted for fatty acid synthesis, which is in turn incorporated into new phospholipids (PLs) (FIG. 8F) required for cell proliferation and maintenance. Since citrate replenishment from glucose is already reduced in ME2 knockdown cells, withholding glucose would further compromise their ability to maintaining PL homeostasis, thereby curtailing cell growth and survival.

Figure 9:
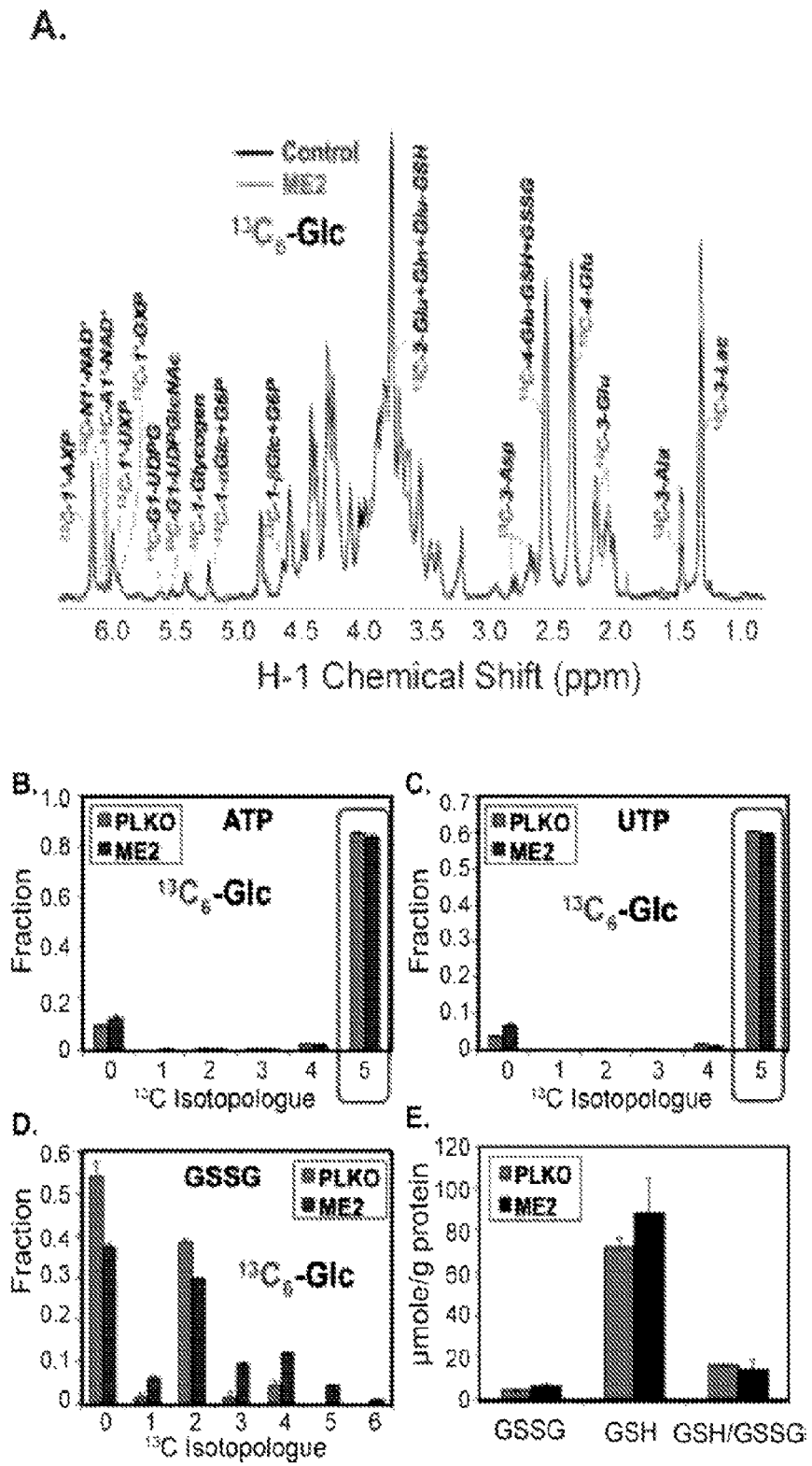
FIG. 9 shows the effect of ME2 suppression on incorporation of $^{13}C$ atom from $^{13}C_6$-Glc or $50^{13}C_5$,$^{15}N_2$-Gln into nucleotides and glutathiones in A549 cells. A549 cells with or without ME2 knockdown were grown in $^{13}C_6$-Glc (100%) or $^{13}C_5$,$^{15}N_2$-Gln medium for 24 h. Cells were harvested by acetonitrile quenching, extracted and analyzed for $^{13}C$ labeling patterns of nucleotides and glutathiones (reduced form GSH and oxidized form GSSG) by 1D HSQC NMR and FT-ICR-MS, as described in Methods. A and F: 1D HSQC analysis of the abundance of $^{13}C$ labels at different positions of various metabolites, including the C1' ribosyl residue in adenine (AXP), uracil (UXP), and guanine nucleotides (GXP); Lac: lactate; G6P: glucose-6-phosphate; UDP-GlcNAc: UDP-N-acetylglucosamine; UDPG: UDP-glucose. B and C: $^{13}C$ mass isotopologue distribution of ATP and UTP in control and ME2 knockdown A549 cells, respectively, grown in 100% $^{13}C_6$-Glc; $^{13}C_5$-isotopologues (5) represent fully $^{13}C$ labeled ribosyl moiety. D and G: $^{13}C$ mass isotopologue distribution of GSSG in control and ME2 knockdown A549 cells with $^{13}C_6$-Glc and $^{13}C_5$,$^{15}N_2$-Gln as tracers, respectively. E: Total levels of GSH and GSSG in the $^{13}C^6$-Glc experiment were quantified from $^1H$ NMR data using 30 nmoles of DSS as calibration standard. Each value was an average of duplicate samples shown with error bars as SEM.
Figure 9:
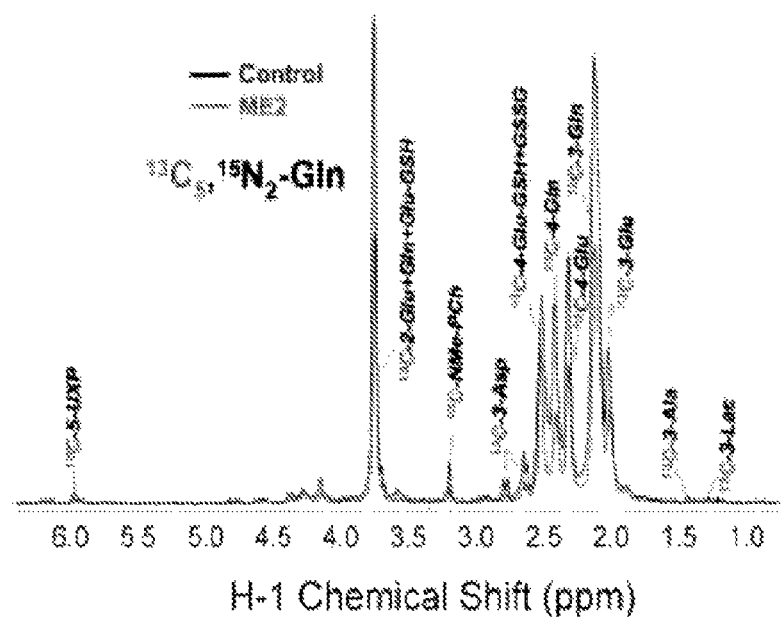
Figure 9:
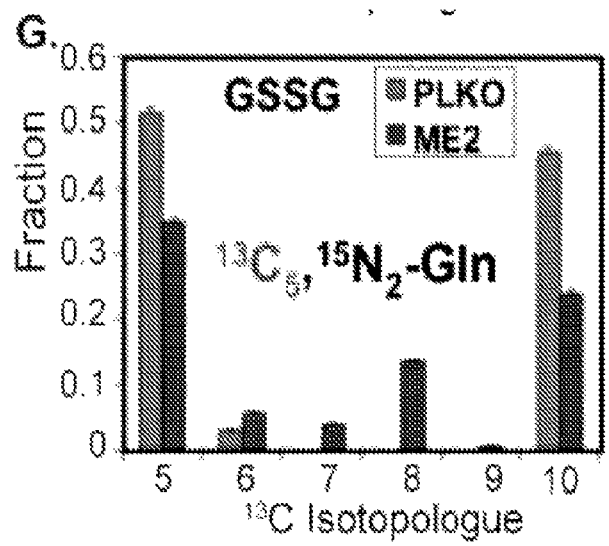

In order to obtain energy and the essential precursors for the synthesis of macromolecules, tumor mitochondria adapt by overexpressing glutaminase facilitating the use of glutamate as a fuel. As noted above, high levels of ME2 in tumor cells can then allow pyruvate to be produced from malate within the mitochondria. ME2 is one of the few progression-linked enzymes in Morris hepatoma series, as is a phosphate-dependent glutaminase, suggesting an important role of ME2 in glutamine metabolism in tumors. The oxidation of glutamate by tumor mitochondria is accompanied by metabolic interactions with cytosolic malate and/or pyruvate, and extrusion of citrate and alanine into the cytoplasm. These two major products play an important role in tumor metabolism. Therefore, depletion of ME2 severely affected cellular ATP production (FIG. 9A).

Another possibility is that with ME2 knockdown, glucose flux through the pentose pathway pathway (PPP) may become more important for NADPH production to sustain GSSG reduction to GSH. Relative to the control cells, the ME knockdown cells exhibited comparable PPP capacity, as evidenced by the similar capacity for synthesizing ribosyl moiety of nucleotides (5 isotopologues of ATP and UTP, FIGS. 9B and 9C; $^{13}$C-1'-AXP, -UXP, and -GXP, FIG. 9A) from $^{13}$C$_6$-Glc. This in turn could be related to the comparable GSH/GSSG ratio in the ME2 knockdown and control cells (FIG. 9E). However, total GSH and GSSG levels were somewhat higher in ME knockdown cells than in control cells (FIG. 9D). Without wishing to be limited by theory, this may be a result of increased synthesis of glutathione from $^{13}$C$_6$-Glc since the fractional distribution of $^{13}$C-labeled GSSG isotopologues was higher in ME knockdown cells than in control cells (FIG. 9D). In contrast, ME2 knockdown cells derived less glutathione from glutamine (FIGS. 9F and 9G), making them rely more on glucose for glutathione-mediated anti-oxidation.

When deprived of glucose, ME2 knockdown cells become more vulnerable to cell death. Our data indicates that knockdown ME2 inhibits ATP, PC (fatty acyl chain), and protein (as evidenced by decreased Val consumption) biosynthesis, which may block A549 cell proliferation. This effect on PC appears to be greater with glucose than with Gln as tracer. These effects could be mediated via inhibition of the anaplerotic input from Gln into the Krebs cycle but not in terms of the glucose-driven Krebs cycle activity. This may in part account for the sensitivity of ME2 KO to glucose deprivation. ME2 KO also perturbs glutathione metabolism, particularly in terms of GSH oxidation to GSSG. There is an opposite trend for glucose and Gln as the tracer in terms of the fractional distribution of GSSH isotopologues. ME2 KO cells appear to rely more on glucose than on Gln for GSH turnover. This could also contribute to the sensitivity of ME2 KO to glucose deprivation. Accordingly, these data show that using an ME2 inhibitor and a glycolysis inhibitor e.g., those described herein, is an effective treatment for proliferative disorders, e.g., any cancer described herein.

Example 9: Stable Knockdown of ME2 Induced Apoptosis and Differentiation

Figure 10:
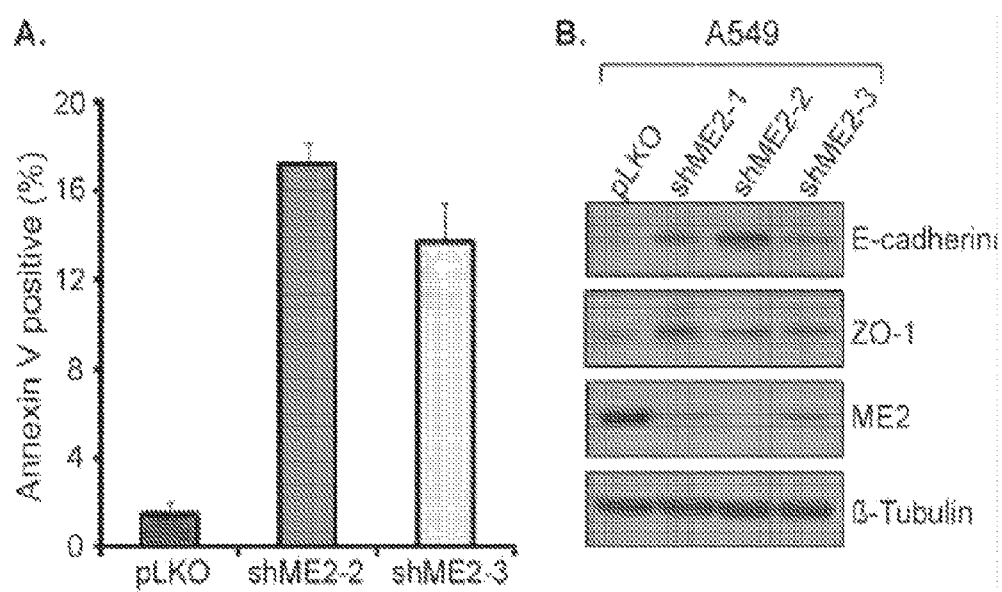
FIG. 10 shows stable knockdown of endogenous ME2 levels induces A549 lung cancer cell lines apoptosis and differentiation and inhibits adhesion and migration. A: Depletion of ME2 increases A549 basal apoptosis. Cell death in A549 cells with or without ME2 knockdown were analyzed by Annexin V reagent. B: A549 cells with or without ME2 knockdown were lysed with RIPA lysis buffer, and equal amount of protein lysate were resolved by Western blotting. Western blots were probed with anti-E-cadherin, ZO-1, ME2 and anti-β-tubulin antibodies. Data are representative of two independent experiments.

Since ME2 deficient cells proliferate much slower than control A549 cells (FIGS. 7B and 7D), we assessed whether they were more apoptotic. Annexin-V assays indicated that ME2 deficient cells had higher rates of apoptosis than control cells (FIG. 10A). Apoptosis induced by ME2 knockdown increased 9.4 to 11.7-fold as compared with the control vector group. Cell cycle analysis showed that ME2 deficiency caused only a modest increase in the number of cells in the G1 phase of the cell cycle.

Next, we examined differentiation caused by ME2 depletion in A549 cells. E-cadherin and ZO-1, both markers of epithelial cell differentiation, were analyzed. As shown in FIG. 10B, ME2 knockdown increased E-cadherin and ZO-1 expression in three independent pools. Thus, our data point to two major effects of ME2 deficiency: increased differentiation as exemplified by increases in E-cadherin and ZO-1 expression and a decreased growth rate with apoptosis as the likely underlying mechanism.

Figure 11:
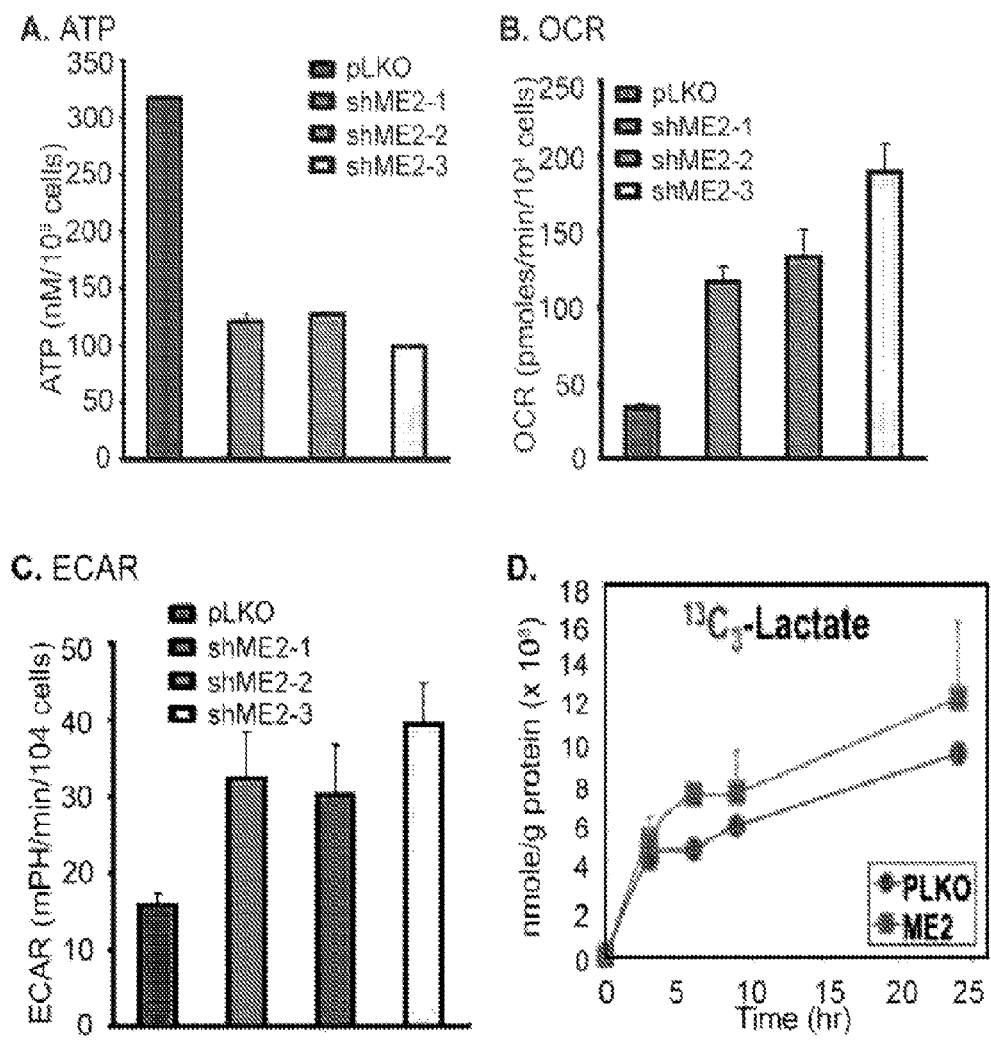
FIG. 11 shows ME2 depletion inhibits ATP and NADPH production, while enhancing A549 cells oxygen consumption and ROS production. A: Depletion of ME2 inhibits ATP production in A549 cells. Data are expressed as mean±SD, n=3. B: Knockdown of ME2 in A549 cells increase $O_2$ consumption. C: Knockdown of ME2 in A549 cells increases [H+] excretion. D: Increased $^{13}C_3$-lactate excretion induced by ME2 knockdown in A549 cells, as determined by $^1H$ NMR; data are expressed as mean±SEM, n=2. E: Increased ROS in A549 ME2 knockdown cells detected by flow cytometry using CM-$H_2$DCFDA as probe. Each histogram is representative of three experiments. F: Depletion of ME2 increases NADP/NADPH ratio. Data are expressed as mean±SD, n=3.
Figure 11:
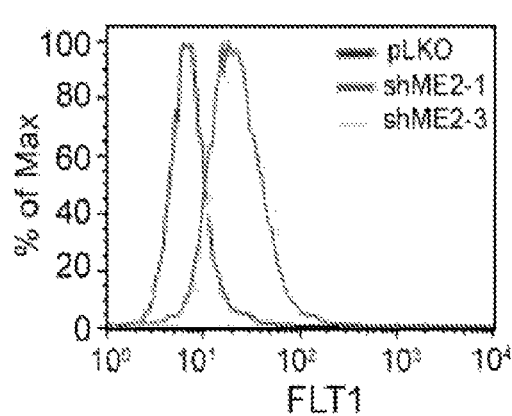
Figure 11:
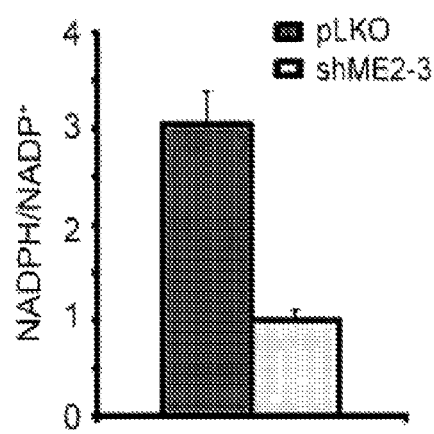

Example 10: Depletion of ME2 Inhibits ATP Production, Increased Oxygen Consumption and Enhanced ROS Production Without wishing to be bound by theory, decreased proliferation and increased apoptosis in ME2 deficient A549 cells may reflect a decrease in ATP levels since ME2 plays a crucial role in glutamine oxidation via the Krebs cycle. As illustrated in FIG. 11A, in A549 cells, knockdown of ME2 led to an approximately 50% decrease in ATP level, as compared to control. These data were corroborated by results from stable isotope tracer experiments, where the total $^{13}$C fractional enrichment in ATP from 50% $^{13}$C$_6$-Glc, as determined by FT-ICR-MS, was lower (42.6%±0.4%) for ME2 deficient cells than for control cells (48.9%±10.8%).

Next, we asked whether this decrease reflects decreased ATP generation perhaps via a shift from mitochondrial oxidative phosphorylation to fermentative glycolysis. We assessed O$_2$ consumption and extracellular acidification changes using a Seahorse machine. Knockdown of ME2 led to a 3-4 fold increase in oxygen consumption (FIG. 11B), suggesting that ME2 depletion could lead to uncoupling of ATP production from oxygen consumption or to the activation of ATP-consuming "futile" cycles with heat production. Moreover, we also observed increased proton extrusion with ME2 knockdown (FIG. 11C), which is consistent with an increased rate of $^{13}$C$_3$-lactate production and released into the medium using $^{13}$C$_6$-Glc as tracer (FIG. 11D). Accordingly, ME2 depletion led to dramatic reprogramming of intermediary metabolism.

The ME2 catalyzed reaction could lead to a concomitant reduction of dinucleotide cofactor NAD$^+$/NADH ratio (and of NADP$^+$/NADPH ratio). NADH (and more classically NADPH) are important antioxidants, which play an important role in maintaining redox balance. It is generally well-recognized that increased generation of ROS in mitochondria resulting from redox imbalance can kill cancer cells. Therefore, ME2 knockdown could diminish anti-oxidant defense and lead to increased ROS. Compared to empty vector control, we observed significant increases in basal ROS content in two independent A549 ME2 knockdown cells, as quantified by flow cytometry using CD-H$_2$DCFDA as a fluorescent probe (FIG. 11E). The NADPH/NADP$^+$ ratio also decreased in A549 ME2 knockdown cells (FIG. 11F). There was no change in NADH/NAD$^+$ ratio. These data suggest that anti-oxidant defenses were compromised in ME2 depleted cells. Indeed, we did not observe the expected decrease in GSH or GSH/GSSG ratio in ME2 KD cells (FIGS. 9A and 9E), which should occur if GSH is oxidized to GSSH to detoxify ROS.

Example 11: AKT Signaling was Down Regulated in the ME2 Deficient State

Metabolic pathway can "sense signal" to canonical molecular signaling pathway. The increased apoptosis and differentiation in ME2 depleted A549 cells suggested that the PI3K/AKT or Ras/Raf/MEK/ERK pathway might be inhibited by ME2 knockdown.

A549 cells bear a point activating mutation in K-ras. AKT activation is a multistep process involving both membrane translocation and phosphorylation. The pleckstrin homology domain of the AKT kinases has affinity for the 3'-phosphorylated phosphoinositides 3,4,5-triphosphate (PI 3,4,5-P3)

produced by PI3K. Phospholipid binding triggers the translocation of AKT kinases to the plasma membrane. Upon membrane localization, AKT molecules are phosphorylated at Thr-308 in the kinase activation loop and Ser-473 in the carboxyl-terminal tail. Thr-308 phosphorylation is necessary for AKT activation, and Ser-473 phosphorylation is required for maximal activity. Phosphorylation on these residues is induced by growth factor stimulation and inhibited by the PI3K inhibitor, LY294002. Indeed, the kinase responsible for Thr-308 phosphorylation PDK1 (3-phosphoinositide-dependent kinase) is activated by the PI3K lipid product PI-3,4,5-P3 and phosphorylates Thr-308 of AKT upon PI3 kinase activation by recognizing PI-3,4,5-P3. The identity of PDK2, the kinase(s) responsible for Ser-473 phosphorylation, is controversial. mTOR complex-2 (mTORC2) was identified as the physiological PDK2 kinase, and this fact is generally accepted in the field. AKT promotes nuclear entry of Mdm2, thus inhibiting the p53 pathway. AKT also induces cytoplasmic localization of p21 and p27, promoting cell growth. Moreover, AKT stabilizes cyclin D1. These functions of AKT lead to insensitivity to anti-growth signals. AKT inhibits apoptosis by inactivating the pro-apoptotic factor BAD and (pro) caspase-9. IKB kinase is activated by AKT, resulting in NF-kB transcription of anti-apoptotic genes. Also AKT inactivates forkhead transcription factors, thereby inhibiting expression of Fas ligand. Thus, AKT serves anti-apoptotic (i.e. pro-survival) functions and it also promotes tumor cell growth. ME2 knockdown dramatically inhibits AKT activity, which may further reduce the tumorigenic potential of ME2 deficiency cells in vivo.

Cellular redox status change may also be contribute to AKT activity. The experiments of Pelicano et al., *J. Cell Biol.* 175:913-923 (2006) suggest that mitochondrial respiration defects can lead to activation of the AKT pathway, an effect mediated by NADH. Their data indicates that respiration-deficient cells exhibit dependency on glycolysis, increased NADH, and activation of AKT. Furthermore, they found that the increase in NADH inactivates PTEN through a redox modification mechanism, leading to AKT activation. Our studies indicate that silencing of ME2 in A549 cells is accompanied by enhanced ROS generation and increased $NAD^+/NADH$ and $NADP^+/NADPH$ ratios. The manipulation of cellular levels of ROS (smaller increases in ROS than what are needed to cause cell death) can induce cancer cell differentiation. It is conceivable that the reducing power of NADH may lead to diminished capacity to maintain a high enough ratio of $NADPH/NADP^+$, thus inhibiting AKT activity. Indeed this sequence of events may account for the increase in ROS that result from depletion of ME2. Other evidence indicates that AKT can be activated by the direct physical association of PDK1 with AKT1, which is independent of membrane localization and phosphatidylinositol 3 kinase. Consistent with this finding, we found that in A549 cells with ME2 depletion, PDK1 activity was dramatically inhibited. Antioxidant NAC and GSH could rescue the AKT and PDK1 activity inhibition by scavenging of ROS. Further, the effect of ME2 on AKT activity regulation may vary with cell type. In leukemia cells, we have previously found that knockdown of ME2 can increase AKT activity, perhaps due to an effect on hemoglobin synthesis during leukemia cell differentiation. Hemoglobin synthesis may stimulate AKT.

Figure 12:
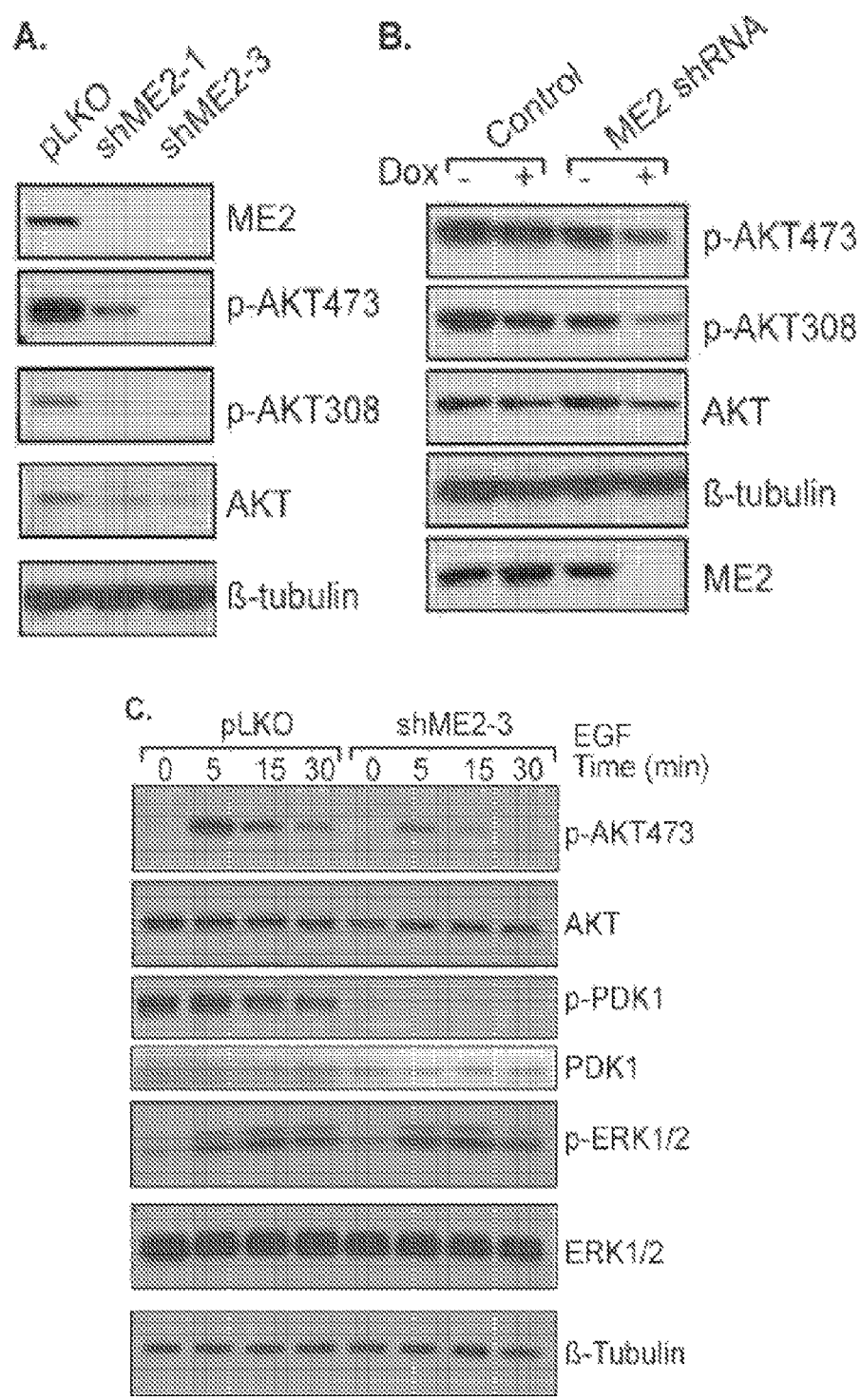
FIG. 12 shows knockdown of ME2 inhibits AKT activity in A549 cells. A: Basal AKT activity in stable ME2 knockdown cells. B: Inducible shRNA induces ME2 knockdown and inhibits basal AKT activity in A549 cells. C: ME2 knockdown and control cells were plated at approximately 60% confluence, starved for 24 h, and stimulated with 100 ng/ml EGF. The cells were lysed with RIPA buffer. Equal amounts of protein were analyzed for p-AKT473, p-AKT308 (with pAKT S473 and pAKT T308 specific antibodies respectively), AKT, p-PDK1, PDK1, p-ERK1/2, ERK1/2, and β-tubulin by Western blotting.

We first looked at the effects on basal AKT phosphorylation using pAKT T308 and pAKT 5473 specific antibodies. Relative to A549 control cells, phosphorylation at both T308 and S473 were markedly diminished in the ME2 deficient cells (FIG. 12A). To further confirm the inhibition of AKT activity, we established an inducible shRNA knockdown system. As shown in FIG. 12B, doxycycline-induced ME2 depletion significantly inhibited AKT activity in A549 cells. Additionally, we investigated AKT activity in response to EGF stimulation in ME2 knockdown cells. Serum starved A549 cells with or without ME2 depletion were stimulated with EGF for 0-30 min as indicated in FIG. 12C. ME2 deficiency down regulated phospho-AKT levels in response to EGF stimulation, suggesting again that the ME2 deficient condition inhibits AKT signaling. Moreover, we also found that depletion of ME2 dramatically down regulated p-PDK1 activity (FIG. 12C), suggesting that ME2 regulates AKT activity via modulation of PDK1 activation or acts at a step proximate to it. Importantly, we found no change in pERK, supporting the notion that ME2 inhibition was unlikely to be inhibiting Ras activity, since Ras activation is known to increase both ERK phosphorylation and AKT activity.

Example 12: Knockdown of Endogenous ME2 Suppressed Tumor Growth In Vivo

Figure 13:
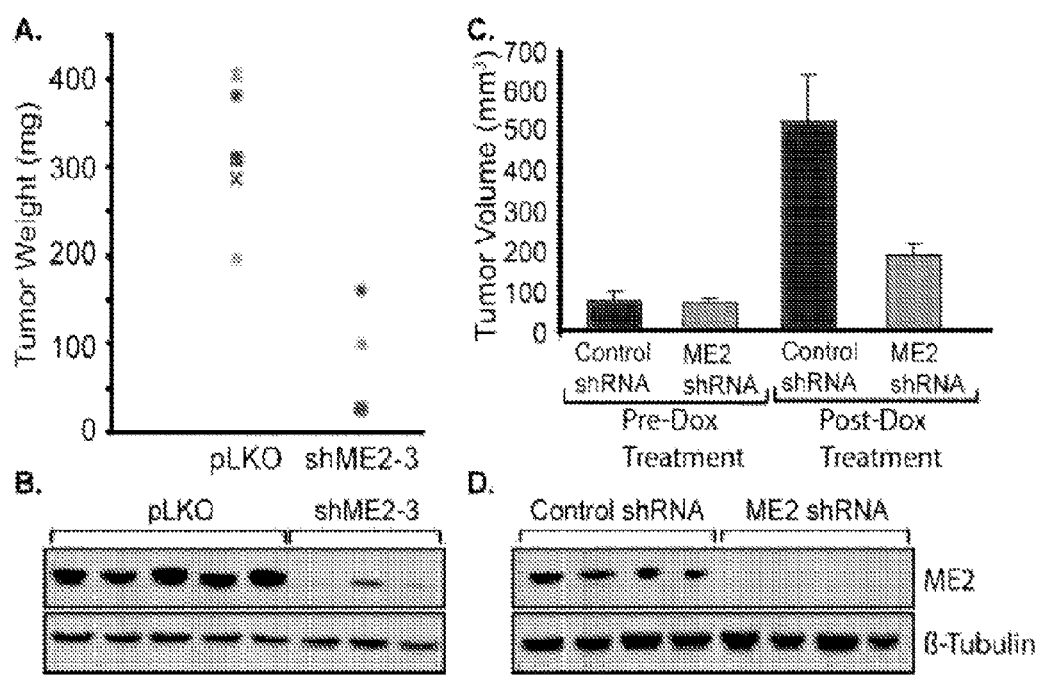
FIG. 13 shows stable knockdown of endogenous ME2 levels in A549 cells suppresses tumor formation. Stable knockdown of ME2 in A549 cells led to reduced tumor size in nude mice. A: Approximately 5×10⁶ ME2 deficient cells from ME2 specific shRNA or control pLKO cells were subcutaneously implanted into female athymic nude mice. Tumor-bearing mice were sacrificed after 6 weeks and the tumors were dissected and weighed. B: ME2 expression levels from tumor samples were analyzed by Western blotting. C: Approximately 5×10⁶ A549 cells containing DOX inducible-ME2 specific shRNA or control shRNA cells were subcutaneously implanted into female athymic nude mice. 10 days later, Dox (2 mg/ml) were fed and tumor-bearing mice were sacrificed after 6 weeks and the tumors volume were measured. The tumor volume was calculated using the formula: V=0.4 AB² (A: Long diameter; B: short diameter). D: ME2 expression levels from tumor samples were analyzed by Western blotting.

The experiments described herein show that knockdown of ME2 in tumor cells inhibited cell survival and induced cell differentiation. To study the effects of ME2 knockdown on in vivo tumorigenicity of A549 cells, we injected vector control and ME2 knockdown clones (shME2-2 and shME2-3) subcutaneously into nude mice and examined tumor formation and progression. ME2 knockdown cells grew much slower than wild type cells (FIG. 13A). Western blot confirmed knockdown of ME2 in vivo (FIG. 13B). We also constructed an shRNA inducible system. In one group (4 mice), each mouse received a control-shRNA inoculation in one flank and an ME2 shRNA clone in the other. After 10 days, both control and ME2 shRNA tumors grew similarly. We then fed the mice 2 mg/ml Dox plus 15% sugar. After 5 weeks, tumor sizes were measured. Similar to data obtained from the constitutive shRNA knockdown in the inducible system, knockdown of ME2 also inhibited tumor growth as compared with control shRNA (FIG. 13C). Western blot confirmed ME2 knockdown in the inducible system (FIG. 13D).

Example 13: Combination Therapy to Suppress Xenograft Tumor Growth

Figure 14:
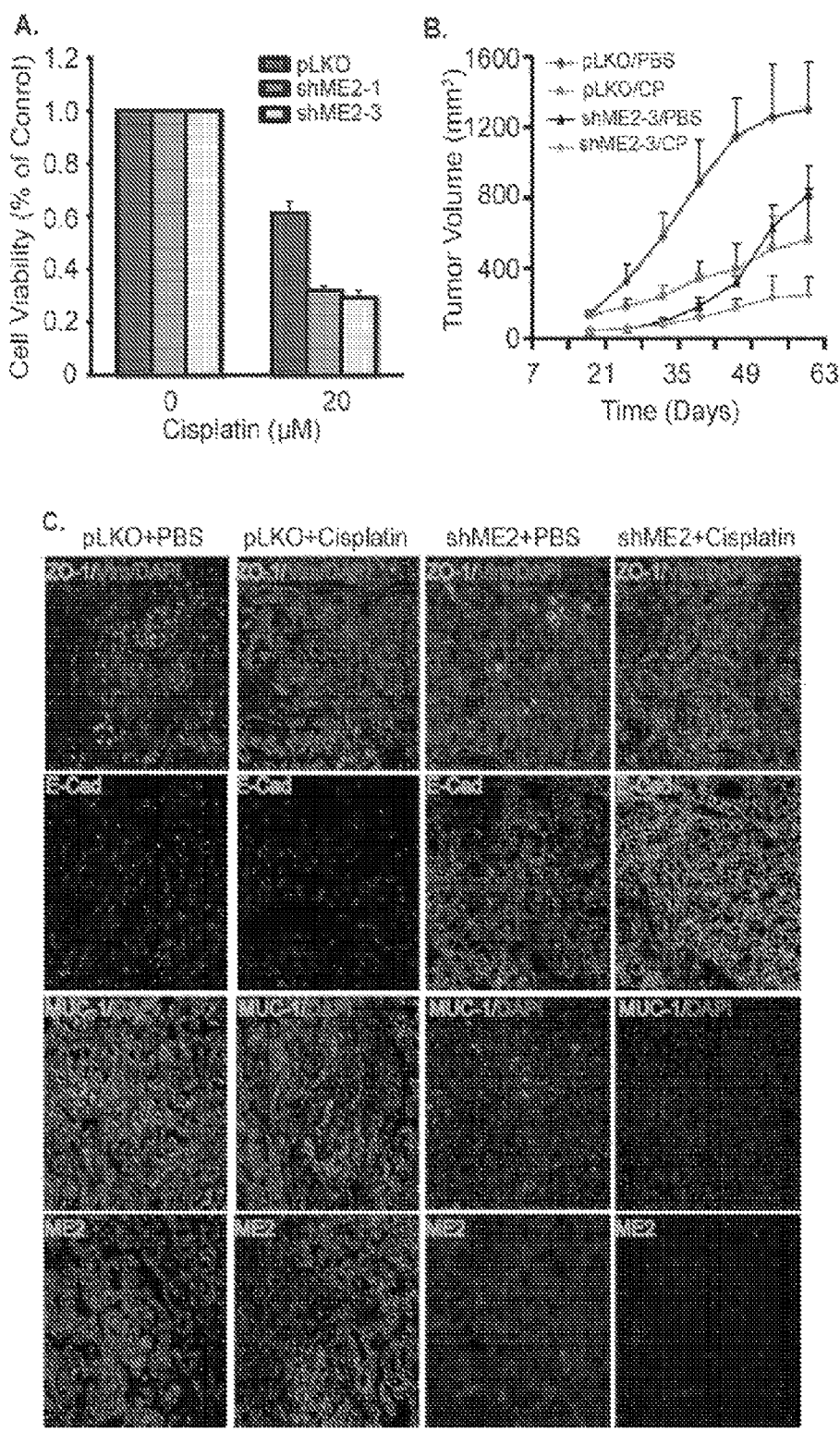
FIG. 14 shows cisplatin synergistically inhibits tumor growth in ME2 knockdown cells. A: Depletion of ME2 renders cells more sensitive to cisplatin treatment. ME2 knockdown and control cells were plated in 6-well plates, and 24 h later, the cell were treated with 20 μM cisplatin. After 72 h, cells were stained with trypan blue and live cells were counted. B: Stable knockdown of ME2 combine cisplatin treatment in A549 cells synergistically inhibits tumor size in nude mice. Approximately 5×10⁶ ME2 deficient cells from ME2 specific shRNA or control pLKO cells were subcutaneously implanted into female athymic nude mice as described in Materials and Methods. Tumor size was measured and calculated. C: Depletion of ME2 inhibits mucin-1 and vimentin expression and increase differentiation marker E-cadherin and ZO-1 expression in vivo.

Cisplatin is commonly used to treat NSCLC. It also promotes ROS production. To explore whether knockdown of ME2 may benefit tumor therapy in the context of cisplatin treatment, we investigated the effect of cisplatin on A549 cells with or without ME2 depletion. Deficiency of ME2 in vitro increased the sensitivity of A549 cells in vitro to cisplatin treatment (FIG. 14A). We therefore treated A549 xenograft tumors formed from wild type and ME2 knockdown cells with cisplatin. As shown in FIG. 14B, ME2 depletion significantly inhibited A549 tumor cell growth in vivo; however, the growth of ME2 knockdown tumors resumed when the tumor size reached about 350 $mm^3$. Cisplatin treatment could prevent this later tumor growth. ME2 depletion inhibited mucin-1 and vimentin expression, and increased tumor cell expression of E-cadherin and ZO-1 in vivo (FIG. 14C). The combination of ME2 depletion and cisplatin also affected E-cadherin and mucin-1 expression. Accordingly, these data show that combination therapy, e.g., using an ME2 inhibitor and an antineoplastic agent, e.g., a chemotherapeutic agent as described herein, could be administered to treat a proliferative disorder, e.g., any cancer described herein.

Example 14: Depletion of ME2 Induced Cell Death and Differentiation Via Malate Accumulation and ROS Production Our data showed that depletion of ME2 impacted growth of A549 lung cancer cells by inducing apoptosis and differentiation. Without wishing to be limited by theory, since the function of ME2 is to convert malate to pyruvate, it is conceivable that mitochondrial malate may be increased in the ME2 knockdown cells and that this may be playing a mechanistic role in the ME2 knockdown phenotype. Our study indicated that depletion of ME2 led to malate accumulation (FIGS. 11A and 11B) and supplementation of exogenous malate inhibited A549 cell growth and induced cell death in vitro. Our published data also indicated that malic enzyme family member ME2 plays important role in regulating leukemia cell proliferation and differentiation (Ren et al., *PLoS One* 5 (2010)). ROS has been reported to induce tumor cell differentiation in hepatoma (Ren et al., *Cell Biol. Int.* 22:41-49 (1998)) and leukemia (Nagy et al., *Leuk. Res.* 19:203-212 (1995)). Without wishing to be limited by theory, an appropriate amount of ROS may be important for tumor cell differentiation and death. Since ME2 depletion caused malate accumulation in A549 cells, the accumulation of malate may enhance ROS production in the mitochondria. In our published data described in Ren et al., *PLoS One* 5 (2010), supplementation of sodium malate failed to induce K562 cell differentiation. It is possible that sodium malate cannot pass through the cell membrane and get into the mitochondria. In the current study, a cell permeable faint of malate was used to treated A549 cells. We observed cell proliferation inhibition and cell death with concomitant increase in ROS by exogenous DMM treatment, similar to the effects observed with ME2 depletion. ROS play a crucial role in regulating cells growth, differentiation and apoptosis. ROS concentration is important for its function. Cellular ROS level is tightly controlled by both the rate of single electron reduction of $O_2$ to superoxide ($O_2.^-$) by the electron transport chain and the rate of scavenging by intracellular antioxidant pathways. Under physiological conditions, the ROS production and scavenge is balanced. High levels of ROS can cause cell death, whereas low levels of ROS can function as a second messenger. Our data have shown that the ROS production in ME2 knockdown cells increased. Increased ROS production may be the mechanism of ME2 knockdown induced apoptosis and differentiation even though anti-oxidant such as NAC does not rescue the phenotype.

Two ways to accumulate ROS in cells is through increased ROS production and inhibition of antioxidant defenses. Mitochondrial ROS generation is the major source of oxidative stress in the cell, and complex I site plays important role in controlling ROS generation. Malate is the substrate of complex I. Without wishing to be bound by theory, a possible mechanism is that malate accumulation in mitochondria may enhance the TCA cycle, accelerating ROS production. The other way to increase ROS level is to inhibit antioxidant defenses. $NADH/NAD^+$, $NADPH/NADP^+$, GSH/GSSG, thioredoxin ($Trx(SH)_2/TrxSS$), and glutaredoxin ($Grx(SH)_2/GrxSS$) are the principal redox couples involved in intracellular ROS balance. Our data showed that depletion of ME2 also decreased $NADPH/NADP^+$ ratio (FIG. 10E) and increased oxidized glutathione, which indicated that knockdown of ME2 impacted the ROS scavenging system.

ME2 knockdown depleted a source of pyruvate production and this inhibition may also partly contribute to cell growth inhibition. Our experiments showed that ME2 knockdown cells lose the ability to use glutamine (FIG. 7E), since glutamine supplementation did not rescue the phenotype. On the contrary, supplementation by exogenous pyruvate rescued cell death to control levels (FIG. 7F). These data indicated that pyruvate production from the action of ME2 is important for cell growth, and in A549 cells.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents and patent applications are herein incorporated by reference in their entirety to the same extent as if each individual publication, patent or patent application was specifically and individually indicated to be incorporated by reference in its entirety.

What is claimed is:

1. A method of treating lung cancer in a subject, the method comprising administering to a subject in need thereof a therapeutically effective amount of a composition comprising a single active agent, wherein the single active agent consists of dimethyl malate.

2. The method of claim 1, wherein said composition is administered parenterally.

3. The method of claim 1, wherein said method further comprises administering to said subject a second composition comprising a malic enzyme 2 inhibitor and wherein said dimethyl malate, and said malic enzyme 2 inhibitor are together in an amount sufficient to treat lung cancer.

4. The method of claim 3, wherein said malic enzyme 2 inhibitor is an RNAi agent, S-oxalylglutathione or a derivative thereof, a lanthanide, a steroid, an anti-ME2 antibody, a PI3K inhibitor, an RTK inhibitor, a PDK1 inhibitor, an AKT inhibitor, or an mTOR inhibitor.

5. The method of claim 4, wherein said RNAi agent comprises a nucleic acid sequence substantially identical to the sequence of any one of SEQ ID NOs:7-42.

6. The method of claim 1, wherein said method further comprises administering to said subject a second composition comprising an antineoplastic agent and wherein said dimethyl malate, and said antineoplastic agent are administered together in an amount sufficient to treat lung cancer.

7. The method of claim 6, wherein said antineoplastic agent is one or more of a chemotherapeutic agent, an immunomodulatory agent, an antiangiogenic agent, a mitotic inhibitor, a nucleoside analog, a DNA intercalating agent, a topoisomerase analog, an antibody, a cytokine, or a folate antimetabolite.

8. The method of claim 7, wherein said antineoplastic agent is said chemotherapeutic agent selected from the group consisting of cisplatin, carboplatin, chlorambucil, melphalan, nedaplatin, oxaliplatin, triplatin tetranitrate, satraplatin, imatinib, nilotinib, dasatinib, and radicicol.

9. The method of claim 1, wherein said method further comprises administering to said subject a second composition comprising a glycolysis inhibitor and wherein said dimethyl malate, and said glycolysis inhibitor are together in an amount sufficient to treat lung cancer.

10. The method of claim 9, wherein said glycolysis inhibitor is a hexokinase inhibitor, a lactate dehydrogenase inhibitor, a phosphofructokinase 2 or phosphofructo-2-kinase/fructose-2,6-bisphosphatase inhibitor, a pyruvate kinase M2 inhibitor, a transketolase inhibitor, a pyruvate dehydrogenase inhibitor, a pyruvate dehydrogenase kinase inhibitor, a glucose-6-phosphate dehydrogenase inhibitor, a GLUT inhibitor, a proton transport inhibitor, a monocarboxylate transporter inhibitor, a hypoxia-inducible factor 1 alpha inhibitor, an AMP-activated protein kinase inhibitor, a glutamine inhibitor, an asparagine inhibitor, an arginine inhibitor, a fatty acid synthase inhibitor, or an ATP-citrate lyase inhibitor.

11. The method of claim 10, wherein said hexokinase inhibitor is a hexokinase 2 inhibitor and said lactate dehydrogenase inhibitor is a lactate dehydrogenase A inhibitor.

12. The method of claim 1, wherein said lung cancer is non-small cell lung cancer.

* * * * *

UNITED STATES PATENT AND TRADEMARK OFFICE
CERTIFICATE OF CORRECTION

PATENT NO. : 9,931,313 B2  
APPLICATION NO. : 14/390155  
DATED : April 3, 2018  
INVENTOR(S) : Vikas P. Sukhatme and Jian-Guo Ren It is certified that error appears in the above-identified patent and that said Letters Patent is hereby corrected as shown below:

On the Title Page

Column 2 (Abstract), Line 3, delete "cancel-," and insert -- cancer, --

Signed and Sealed this  
Seventh Day of January, 2020

Andrei Iancu  
*Director of the United States Patent and Trademark Office*